US012577611B2

(12) United States Patent
Glezer et al.

(10) Patent No.: US 12,577,611 B2
(45) **Date of Patent: *Mar. 17, 2026**

(54) METHODS FOR IN SITU TRANSCRIPTOMICS AND PROTEOMICS

(71) Applicant: Singular Genomics Systems, Inc., San Diego, CA (US)

(72) Inventors: Eli N. Glezer, Del Mar, CA (US); Hu Cang, San Diego, CA (US); Zhenmin Hong, San Diego, CA (US)

(73) Assignee: Singular Genomics Systems, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/978,794

(22) Filed: Dec. 12, 2024

(65) Prior Publication Data

US 2025/0109430 A1 Apr. 3, 2025

Related U.S. Application Data

(60) Division of application No. 18/443,079, filed on Feb. 15, 2024, now Pat. No. 12,286,666, which is a continuation of application No. 17/938,329, filed on Oct. 5, 2022, which is a continuation of application No. 17/816,841, filed on Aug. 2, 2022, now Pat. No. 12,180,542, which is a continuation of application No. 17/840,473, filed on Jun. 14, 2022, now Pat. No. 11,891,656, which is a continuation of application No. 17/840,469, filed on Jun. 14, 2022, now Pat. No. 11,643,679, which is a continuation of application No. 17/396,575, filed on Aug. 6, 2021, now Pat. No. 11,492,662.

(60) Provisional application No. 63/209,886, filed on Jun. 11, 2021, provisional application No. 63/140,700, filed on Jan. 22, 2021, provisional application No. 63/062,054, filed on Aug. 6, 2020.

(51) Int. Cl.

| | |
|---|---|
| ***C12Q 1/6841*** | (2018.01) |
| ***C12Q 1/6804*** | (2018.01) |
| ***G01N 33/53*** | (2006.01) |

(52) U.S. Cl.

CPC ......... *C12Q 1/6841* (2013.01); *C12Q 1/6804* (2013.01); *G01N 33/5308* (2013.01); *G01N 33/53* (2013.01)

(58) Field of Classification Search

CPC .. C12Q 1/68; C12Q 1/6841; C12Q 2525/357; C12Q 2531/125; G01N 33/53; C07H 21/00

See application file for complete search history.

(56) References Cited

U.S. PATENT DOCUMENTS

| | | | |
|---|---|---|---|
| 4,792,520 | A | 12/1988 | Stambrook et al. |
| 5,034,506 | A | 7/1991 | Summerton et al. |
| 5,235,033 | A | 8/1993 | Summerton et al. |
| 5,599,675 | A | 2/1997 | Brenner et al. |
| 5,750,341 | A | 5/1998 | Macevicz |
| 5,763,594 | A | 6/1998 | Hiatt et al. |
| 5,808,045 | A | 9/1998 | Hiatt et al. |
| 5,872,244 | A | 2/1999 | Hiatt et al. |
| 6,210,891 | B1 | 4/2001 | Nyren et al. |
| 6,218,122 | B1 | 4/2001 | Friend et al. |
| 6,232,465 | B1 | 5/2001 | Hiatt et al. |
| 6,258,568 | B1 | 7/2001 | Nyren |
| 6,271,022 | B1 | 8/2001 | Bochner |
| 6,274,320 | B1 | 8/2001 | Rothberg et al. |
| 6,365,367 | B1 | 4/2002 | Friedman et al. |
| 6,664,079 | B2 | 12/2003 | Ju et al. |
| 7,057,026 | B2 | 6/2006 | Barnes et al. |
| 7,271,952 | B2 | 9/2007 | Suzuki et al. |
| 7,390,463 | B2 | 6/2008 | He et al. |
| 7,541,444 | B2 | 6/2009 | Milton et al. |
| RE41,780 | E | 9/2010 | Brian et al. |
| 8,551,710 | B2 | 10/2013 | Bernitz et al. |
| 8,703,461 | B2 | 4/2014 | Peris et al. |
| 9,371,598 | B2 | 6/2016 | Chee |
| 9,556,473 | B2 | 1/2017 | Bernitz et al. |
| 9,593,365 | B2 | 3/2017 | Frisen et al. |
| 9,598,723 | B2 | 3/2017 | Ammann et al. |
| 10,059,990 | B2 | 8/2018 | Boyden et al. |
| 10,114,015 | B2 | 10/2018 | Glezer et al. |
| 10,138,509 | B2 | 11/2018 | Church et al. |
| 10,266,888 | B2 | 4/2019 | Daugharthy et al. |
| 10,323,272 | B1 | 6/2019 | Rabbani et al. |
| 10,495,554 | B2 | 12/2019 | Deisseroth et al. |
| 10,738,072 | B1 | 8/2020 | Graham et al. |
| 10,774,374 | B2 | 9/2020 | Frisen et al. |
| 10,841,507 | B2 | 11/2020 | Schürf et al. |

(Continued)

FOREIGN PATENT DOCUMENTS

| | | |
|---|---|---|
| JP | 2005/265627 A | 9/2005 |
| JP | 5970959 B2 | 8/2016 |

(Continued)

OTHER PUBLICATIONS

Gusev et al., Rolling Circle Amplification : A New Approach to Increase Sensitivity for Immunohistochemistry and Flow Cytometry. Am. J. of Pathology 159(1) : 63 (Year: 2001).*
Lev et al., On the Use of Eosin as a Fluorescent Dye to Demonstrate Mucous Cells and Other Structures in Tissue Sections. Histochemie 20:363 (Year: 1969).*
Liu et al., High Specific and Ultrasensitive Isothermal Detection of MicroRNA by Padlock Probe-Based Exponential Rolling Circle Amplification. Analytical Chemistry 85:7941 (Year: 2013).*
Payne, Anderew C., Towards Sequencing by synthesis in situ MIT Masters Thesis Jun. 2017.*

(Continued)

*Primary Examiner* — Ethan C Whisenant
(74) *Attorney, Agent, or Firm* — Mintz, Levin, Cohn, Ferris, Glovsky and Popeo, P.C.; Zachary L. Terranova

(57) ABSTRACT

Disclosed herein, inter alia, are compositions and methods of use thereof for interrogating a cell.

20 Claims, 15 Drawing Sheets

(56) References Cited

U.S. PATENT DOCUMENTS

| | | | | |
|---|---|---|---|---|
| 11,155,858 | B2 | 10/2021 | Glezer et al. | |
| 11,434,525 | B2 | 9/2022 | Glezer | |
| 11,486,004 | B2 | 11/2022 | Witters et al. | |
| 11,492,662 | B2 | 11/2022 | Glezer et al. | |
| 11,643,679 | B2 | 5/2023 | Glezer et al. | |
| 11,680,288 | B2 | 6/2023 | Glezer | |
| 11,753,678 | B2 | 9/2023 | Glezer | |
| 11,891,656 | B2 * | 2/2024 | Glezer | G01N 33/5308 |
| 12,006,534 | B2 | 6/2024 | Glezer | |
| 12,180,542 | B2 | 12/2024 | Glezer et al. | |
| 2001/0053519 | A1 | 12/2001 | Fodor et al. | |
| 2001/0054691 | A1 | 12/2001 | Park et al. | |
| 2002/0064779 | A1 | 5/2002 | Landegren et al. | |
| 2003/0032024 | A1 | 2/2003 | Lizardi et al. | |
| 2003/0049862 | A1 | 3/2003 | He et al. | |
| 2003/0077580 | A1 | 4/2003 | Catanzariti et al. | |
| 2003/0082556 | A1 | 5/2003 | Kaufman et al. | |
| 2003/0082576 | A1 | 5/2003 | Jones et al. | |
| 2003/0143536 | A1 | 7/2003 | Lizardi | |
| 2004/0137484 | A1 | 7/2004 | Zhang et al. | |
| 2004/0248318 | A1 | 12/2004 | Weinberger et al. | |
| 2005/0089860 | A1 | 4/2005 | Arita | |
| 2005/0130173 | A1 | 6/2005 | Leamon et al. | |
| 2005/0142556 | A1 | 6/2005 | Hoon et al. | |
| 2005/0208644 | A1 | 9/2005 | Takiguchi et al. | |
| 2005/0287526 | A1 | 12/2005 | Landegren et al. | |
| 2005/0287578 | A1 | 12/2005 | Davis | |
| 2006/0050376 | A1 | 3/2006 | Houston et al. | |
| 2006/0292559 | A1 | 12/2006 | Reddy et al. | |
| 2009/0048119 | A1 | 2/2009 | Krjutskov et al. | |
| 2009/0048785 | A1 * | 2/2009 | Katzir | G06V 20/693<br>702/19 |
| 2009/0298718 | A1 | 12/2009 | Denman et al. | |
| 2011/0223585 | A1 | 9/2011 | Gullberg et al. | |
| 2012/0301886 | A1 | 11/2012 | Farrell et al. | |
| 2013/0085146 | A1 | 4/2013 | Ho et al. | |
| 2014/0031241 | A1 | 1/2014 | Nicol et al. | |
| 2014/0056811 | A1 | 2/2014 | Jacob et al. | |
| 2014/0057799 | A1 | 2/2014 | Johnson et al. | |
| 2014/0120534 | A1 * | 5/2014 | Bernitz | C12Q 1/6809<br>435/6.11 |
| 2014/0170654 | A1 | 6/2014 | Landegren et al. | |
| 2014/0220006 | A1 | 8/2014 | Aghvanyan et al. | |
| 2014/0256588 | A1 | 9/2014 | Glezer et al. | |
| 2014/0274738 | A1 | 9/2014 | Amorese et al. | |
| 2014/0322759 | A1 | 10/2014 | Skirgaila et al. | |
| 2015/0167092 | A1 | 6/2015 | Kartalov et al. | |
| 2015/0225778 | A1 | 8/2015 | Hindson et al. | |
| 2016/0003716 | A1 * | 1/2016 | Torres | G01N 1/30<br>435/40.52 |
| 2016/0108392 | A1 | 4/2016 | Stelling | |
| 2016/0116384 | A1 | 4/2016 | Chen et al. | |
| 2016/0145696 | A1 | 5/2016 | Brandon et al. | |
| 2016/0257993 | A1 | 9/2016 | Fu et al. | |
| 2016/0289750 | A1 | 10/2016 | Landegren et al. | |
| 2016/0304952 | A1 | 10/2016 | Boyden et al. | |
| 2016/0369329 | A1 | 12/2016 | Cai et al. | |
| 2017/0067096 | A1 | 3/2017 | Wassie et al. | |
| 2017/0067925 | A1 | 3/2017 | Spence et al. | |
| 2017/0107563 | A1 | 4/2017 | Samusik et al. | |
| 2017/0212983 | A1 | 7/2017 | Cai et al. | |
| 2017/0343539 | A1 | 11/2017 | Epstein et al. | |
| 2018/0187242 | A1 | 7/2018 | Makrigiorgos et al. | |
| 2018/0246076 | A1 | 8/2018 | Qian et al. | |
| 2019/0017106 | A1 | 1/2019 | Frisen et al. | |
| 2019/0032121 | A1 | 1/2019 | Daugharthy et al. | |
| 2019/0055594 | A1 | 2/2019 | Samusik et al. | |
| 2019/0064109 | A1 | 2/2019 | Brown et al. | |
| 2019/0071668 | A1 | 3/2019 | Schmidt et al. | |
| 2019/0113423 | A1 | 4/2019 | Goodman et al. | |
| 2019/0119735 | A1 | 4/2019 | Deisseroth et al. | |
| 2019/0145982 | A1 | 5/2019 | Chee et al. | |
| 2019/0155835 | A1 | 5/2019 | Daugharthy et al. | |
| 2019/0161796 | A1 | 5/2019 | Hauling et al. | |
| 2019/0177718 | A1 | 6/2019 | Church et al. | |
| 2019/0194709 | A1 | 6/2019 | Church et al. | |
| 2019/0241945 | A1 | 8/2019 | Malyshev et al. | |
| 2019/0241950 | A1 | 8/2019 | Daugharthy et al. | |
| 2019/0258777 | A1 | 8/2019 | Bo et al. | |
| 2019/0264279 | A1 | 8/2019 | Kain et al. | |
| 2019/0376123 | A1 | 12/2019 | Bobrow et al. | |
| 2019/0391140 | A1 | 12/2019 | Aghvanyan et al. | |
| 2020/0071751 | A1 | 3/2020 | Daugharthy et al. | |
| 2020/0087707 | A1 | 3/2020 | Engreitz | |
| 2020/0103639 | A1 | 4/2020 | Skinner et al. | |
| 2020/0124601 | A1 | 4/2020 | Fan et al. | |
| 2020/0140944 | A1 | 5/2020 | Belgrader et al. | |
| 2020/0224244 | A1 | 7/2020 | Nilsson et al. | |
| 2020/0224544 | A1 | 7/2020 | Barker et al. | |
| 2020/0271556 | A1 | 8/2020 | Sarkar et al. | |
| 2020/0277663 | A1 | 9/2020 | Ramachandran Iyer et al. | |
| 2020/0277664 | A1 | 9/2020 | Frenz | |
| 2020/0290043 | A1 | 9/2020 | Williamson et al. | |
| 2020/0294439 | A1 | 9/2020 | Mandle et al. | |
| 2020/0362334 | A1 | 11/2020 | Regev et al. | |
| 2020/0393477 | A1 | 12/2020 | Davey et al. | |
| 2021/0017596 | A1 | 1/2021 | Tong et al. | |
| 2021/0039062 | A1 | 2/2021 | Mirkin et al. | |
| 2021/0108195 | A1 | 4/2021 | Bernate et al. | |
| 2021/0164029 | A1 | 6/2021 | Sekedat et al. | |
| 2021/0164039 | A1 | 6/2021 | Wang et al. | |
| 2021/0189481 | A1 | 6/2021 | Glezer et al. | |
| 2021/0198727 | A1 | 7/2021 | Kühnemund et al. | |
| 2021/0222262 | A1 | 7/2021 | Bakaher et al. | |
| 2021/0230695 | A1 * | 7/2021 | Grunig | A61P 11/00 |
| 2021/0262018 | A1 | 8/2021 | Bava et al. | |
| 2021/0292834 | A1 | 9/2021 | Daugharthy et al. | |
| 2021/0318530 | A1 | 10/2021 | Deissler | |
| 2021/0333211 | A1 | 10/2021 | Chen et al. | |
| 2021/0363579 | A1 | 11/2021 | Daugharthy | |
| 2021/0381043 | A1 | 12/2021 | Ju et al. | |
| 2021/0382033 | A1 | 12/2021 | Mir | |
| 2021/0388424 | A1 | 12/2021 | Bava | |
| 2022/0042083 | A1 | 2/2022 | Glezer et al. | |
| 2022/0042084 | A1 | 2/2022 | Glezer | |
| 2022/0112486 | A1 | 4/2022 | Ramachandran Iyer et al. | |
| 2022/0333173 | A1 | 10/2022 | Glezer et al. | |
| 2022/0333174 | A1 | 10/2022 | Glezer et al. | |
| 2022/0403456 | A1 | 12/2022 | Glezer et al. | |
| 2022/0403457 | A1 | 12/2022 | Glezer et al. | |
| 2023/0027467 | A1 | 1/2023 | Fredriksson | |
| 2023/0057571 | A1 | 2/2023 | Costa et al. | |
| 2023/0088043 | A1 | 3/2023 | Kovacs et al. | |
| 2023/0097368 | A1 | 3/2023 | Glezer | |
| 2023/0100215 | A1 | 3/2023 | Glezer et al. | |
| 2023/0203570 | A1 | 6/2023 | Kovacs et al. | |
| 2023/0357828 | A1 | 11/2023 | Lezer | |
| 2023/0366013 | A1 | 11/2023 | Glezer | |
| 2023/0374572 | A1 | 11/2023 | Glezer | |
| 2024/0026428 | A1 | 1/2024 | Glezer et al. | |
| 2024/0182956 | A1 | 6/2024 | Glezer et al. | |

FOREIGN PATENT DOCUMENTS

| | | | |
|---|---|---|---|
| WO | 8910977 | A1 | 11/1989 |
| WO | 9607669 | A1 | 3/1996 |
| WO | 2004018497 | A2 | 3/2004 |
| WO | WO-2005/039389 | A2 | 5/2005 |
| WO | WO-2008/042067 | A2 | 4/2008 |
| WO | WO-2013/090360 | A2 | 6/2013 |
| WO | WO-2013/090360 | A3 | 8/2013 |
| WO | WO-2014/030066 | A2 | 2/2014 |
| WO | WO-2014/030066 | A3 | 5/2014 |
| WO | WO-2017/079382 | A1 | 5/2017 |
| WO | WO-2018/091676 | A1 | 5/2018 |
| WO | 2018148723 | A1 | 8/2018 |
| WO | WO-2019/068880 | A1 | 4/2019 |
| WO | WO-2019/084062 | A1 | 5/2019 |
| WO | WO-2019/199579 | A1 | 10/2019 |
| WO | WO-2019/222284 | A1 | 11/2019 |
| WO | WO-2020/028194 | A1 | 2/2020 |
| WO | 2020056044 | A1 | 3/2020 |
| WO | WO-2020/076976 | A1 | 4/2020 |
| WO | WO-2020/076979 | A1 | 4/2020 |

(56) References Cited

FOREIGN PATENT DOCUMENTS

| | | | |
|---|---|---|---|
| WO | WO-2020/096687 | A1 | 5/2020 |
| WO | WO-2020/099640 | A1 | 5/2020 |
| WO | WO-2020/123309 | A1 | 6/2020 |
| WO | WO-2020/160044 | A1 | 8/2020 |
| WO | WO-2022/032194 | A1 | 2/2022 |
| WO | WO-2022/032195 | A2 | 2/2022 |
| WO | WO-2022/032195 | A3 | 3/2022 |
| WO | WO-2022/235764 | A1 | 11/2022 |

OTHER PUBLICATIONS

Shao et al.,, Optimization of rolling-circle amplified protein microarrays for multiplexed protein profiling. J. of Biomedicine and Biotechnology 5:299 (Year: 2003).*
Zhu et al., Fluorescent Probes for Sensing and Imaging within Specific Cellular Organelles. Accounts of Chemical Research 49:2115 (Year: 2016).*
Nayyar, et al. (2019) "Overcoming Resistance to Natural Killer Cell Based Immunotherapies for Solid Tumors", Frontiers in Oncology, 9:51 (28 pages).
Nedeljkovic, et al. (2019) "Mechanisms of Chemotherapy Resistance in Triple-Negative Breast Cancer—How We Can Rise to the Challenge", Cells, 8(9):957 (32 pages).
Nie, et al. (2018) "Toll-Like Receptors, Associated Biological Roles, and Signaling Networks in Non-Mammals", Frontiers in Immunology, 9:1523 (19 pages).
Nik-Zainal, et al. (2016) "Landscape of Somatic Mutations in 560 Breast Cancer Whole-genome Sequences", Nature, 534(7605):47-54.
Noggle, et al. (Oct. 5, 2011) "Human Oocytes Reprogram Somatic Cells to a Pluripotent State", Nature, 478(7367):70-75.
O'Gorman, et al. (2015) "Single-cell Systems-level Analysis of Human Toll-like Receptor Activation Defines a Chemokine Signature in Patients with Systemic Lupus Erythematosus", The Journal of Allergy and Clinical Immunology, 136(5):1326-1336.
Paik, et al. (2004) "A Multigene Assay to Predict Recurrence of Tamoxifen-Treated, Node-Negative Breast Cancer", The New England Journal of Medicine, 351(27):2817-2826.
Parker, et al. (2009) "Supervised Risk Predictor of Breast Cancer Based on Intrinsic Subtypes", Journal of Clinical Oncology, 27(8):1160-1167.
Risom, et al. (2018) "Differentiation-state Plasticity is a Targetable Resistance Mechanism in Basal-like Breast Cancer", Nature Communications, 9(1):3815 (17 pages).
Robichaux, et al. (2018) "Mechanisms and Clinical Activity of an EGFR and HER2 Exon 20-selective Kinase Inhibitor in Non-small Cell Lung Cancer", Nature Medicine, 24(5):638-646.
Ronaghi, et al. (Jul. 17, 1998) "A Sequencing Method Based on Real-Time Pyrophosphate", Science, 281(5375):363-365 (6 pages).
Ronaghi, et al., "Pyrosequencing Sheds Light on DNA Sequencing", Genome Research, Jan. 2001, 11(1):3-11 (10 pages).
Ronaghi, et al. (Nov. 1, 1996) "Real-Time DNA Sequencing Using Detection of Pyrophosphate Release", Analytical Biochemistry, 242(1):84-89.
Rossi, et al. (2019) "Single-Cell Analysis of Circulating Tumor Cells: How Far Have We Come in the—Omics Era?", Frontiers in Genetics, 10:958 (12 pages).
Ruparel, et al. (2005) "Design and Synthesis of a 3'-O-Allyl Photocleavable Fluorescent Nucleotide as a Reversible Terminator for Dna Sequencing by Synthesis", Proc Natl Acad Sci U S A, 102(17):5932-5937.
Sankowski, et al. (2019) "Mapping Microglia States in the Human Brain Through the Integration of High-dimensional Techniques", Nature Neuroscience, 22(12):2098-2110.
Shendure, et al. (2005) "Accurate Multiplex Polony Sequencing of an Evolved Bacterial Genome", Science, 309(5741):1728-1732 (6 pages).
Soderberg, et al. (2008) "Characterizing Proteins and Their Interactions in Cells and Tissues Using the in Situ Proximity Ligation Assay", Methods, 45(3):227-232.
Southworth, et al. (May 28, 1996) "Cloning of Thermostable DNA Polymerases from Hyperthermophilic Marine Archaea with Emphasis on *Thermococcus* sp. 9 Degrees N-7 and Mutations Affecting 3'-5' Exonuclease Activity", Proceedings of the National Academy of Sciences of the United States of America, 93(11):5281-5285.
Sporikova, et al. (2018) "Genetic Markers in Triple-Negative Breast Cancer", Clinical Breast Cancer, 18(5):e841-e850.
Steingart, et al. (2014) "Xpert® MTB/RIF Assay for Pulmonary Tuberculosis and Rifampicin Resistance in Adults", Cochrane Database of Systematic Reviews, 2014(1):CD009593 (134 pages).
Svedlund, et al. (2019) "Generation of in Situ Sequencing Based Oncomaps to Spatially Resolve Gene Expression Profiles of Diagnostic and Prognostic Markers in Breast Cancer", EBioMedicine, 48:212-223.
Tavakoli, et al. (2017) "Current Diagnostic Methods for HIV", Future Virology, 12(3):141-155.
Thanna, et al. (2016) "Targeting the Trehalose Utilization Pathways of *Mycobacterium tuberculosis*", Medchemcomm, 7(1):69-85.
Walker, et al. (1988) "Photolabile 1 -( 2-Nitropheny1)ethyl Phosphate Esters of Adenine Nucleotide Analogues. Synthesis and Mechanism of Photolysis", Journal of the American Chemical Society, 110(21):7170-7177.
Wang, et al. (2005) "Gene-expression Profiles to Predict Distant Metastasis of Lymph-node-negative Primary Breast Cancer", Lancet, 365(9460):671-679.
Wu, et al. (2007) "3'-O-Modified Nucleotides as Reversible Terminators for Pyrosequencing", Proc Natl Acad Sci U S A, 104(42):16462-16467.
Zimmermann, et al. (2014) "Chapter 5: Clearing Up the Signal: Spectral Imaging and Linear Unmixing in Fluorescence Microscopy", Confocal Microscopy: Methods and Protocols, Methods in Molecular Biology, 1075:129-148.
Mag, et al. (Nov. 24, 1992) "Synthesis and Selective Cleavage of an Oligodeoxynucleotide Containing a Bridged Non-chiral Internucleotide 3'-phosphoramidate Linkage", Tetrahedron Letters, 33(48):7319-7322.
2006) "The Cancer Genome Atlas Program (TCGA)", National Cancer Institute Center for Cancer Genomics, www.cancer.gov/tcga, 2 pages.
Mirza, et al. (Mar. 14, 2008) "Methods and Approaches for the Comprehensive Characterization and Quantification of Cellular Proteomes Using Mass Spectrometry", Physiological Genomics, 33(1):3-11.
Akira, et al. (2006) "Pathogen Recognition and Innate Immunity", Cell, 124(4):783-801.
Aldape, et al. (2019) "Challenges to Curing Primary Brain Tumours", Nature Reviews Clinical Oncology, 16(8):509-520.
Al-Mutairi, et al. (2019) "Occurrence of Disputed rpoB Mutations Among *Mycobacterium tuberculosis* Isolates Phenotypically Susceptible to Rifampicin in a Country With a Low Incidence of Multidrug-resistant Tuberculosis", BMC Infectious Diseases, 19(1):3 (9 pages).
Alon, et al. (2020) "Expansion Sequencing: Spatially Precise in Situ Transcriptomics in Intact Biological Systems", Biorxiv, 127 pages.
Altfeld, et al. (2015) "Innate Immunity Against HIV-1 Infection", Nature Immunology, 16(6):554-562.
Asif, et al. (2016) "HER-2 Positive Breast Cancer—a Mini-Review", Asian Pacific Journal of Cancer Prevention, 17(4):1609-1615.
Bains, et al. (Dec. 7, 1988) "A Novel Method for Nucleic Acid Sequence Determination", Journal of Theoretical Biology, 135(3):303-307.
Barretina, et al. (2012) "The Cancer Cell Line Encyclopedia Enables Predictive Modelling of Anticancer Drug Sensitivity", Nature, 483(7391):603-607.
Bentley, et al. (Nov. 6, 2008) "Accurate Whole Human Genome Sequencing Using Reversible Terminator Chemistry", Nature, 456(7218):53-59.

(56) References Cited

OTHER PUBLICATIONS

Bergen, et al. (Jun. 17, 2013) "Structures of KOD and 9°N DNA Polymerases Complexed with Primer Template Duplex", ChemBioChem, 14(9):1058-1062.
Chakaya, et al. (2021) "Global Tuberculosis Report 2020—Reflections on the Global TB burden, Treatment and Prevention Efforts", International Journal of Infectious Diseases, 113:S7-S12.
Ciocan-Cartita, et al. (2020) "New Insights in Gene Expression Alteration as Effect of Doxorubicin Drug Resistance in Triple Negative Breast Cancer Cells", Journal of Experimental & Clinical Cancer Research, 39(1):241 (16 pages).
Cocco, et al. (2020) "Biomarkers in Triple-Negative Breast Cancer: State-of-the-Art and Future Perspectives", International Journal of Molecular Sciences, 21(13):4579 (33 pages).
Coussens, et al. (2013) "Neutralizing Tumor-Promoting Chronic Inflammation: A Magic Bullet?", Science, 339(6117):286-291.
Dirks, et al. (2004) "Triggered Amplification by Hybridization Chain Reaction", Proc Natl Acad Sci U S A, 101(43):15275-15278.
Drmanac et al. (Jan. 1998) "Accurate Sequencing by Hybridization for DNA Diagnostics and Individual Genomics", Nature Biotechnology, 16(1):54-58 (6 pages).
Echeverria, et al. (2019) "Resistance to Neoadjuvant Chemotherapy in Triple-negative Breast Cancer Mediated by a Reversible Drug-tolerant State", Science Translational Medicine, 11(488):eaav0936 (16 pages).
Fan, et al. (2018) "Branched Rolling Circle Amplification Method for Measuring Serum Circulating MicroRNA Levels for Early Breast Cancer Detection", Cancer Science, 109(9):2897-2906.
Fodor, et al. (Feb. 15, 1991) "Light-Directed, Spatially Addressable Parallel Chemical Synthesis", Science, 251(4995):767-773 (8 pages).
Fuller, et al. (Apr. 18, 2016) "Real-Time Single-Molecule Electronic DNA Sequencing by Synthesis Using Polymer-Tagged Nucleotides on a Nanopore Array", Proceedings of the National Academy of Sciences of the United States of America, 113(19):5233-5238.
Gaibar, et al. (2020) "Somatic Mutations in HER2 and Implications for Current Treatment Paradigms in HER2-Positive Breast Cancer", Journal of Oncology, 2020:6375956 (13 pages).
Garnett, et al. (2012) "Systematic Identification of Genomic Markers of Drug Sensitivity in Cancer Cells", Nature, 483(7391):570-575.
Garrido-Castro et al. (2019) "Insights into Molecular Classifications of Triple-Negative Breast Cancer: Improving Patient Selection for Treatment", Cancer Discovery, 9(2):176-198.
Gern, et al. (2021) "TGFβ Restricts Expansion, Survival, and Function of T Cells Within the Tuberculous Granuloma", Cell Host & Microbe, 29(4):594-606.
Greenman, et al. (2007) "Patterns of Somatic Mutation in Human Cancer Genomes", Nature, 446(7132):153-158.
Hendry et al. (2017) "Assessing Tumor-infiltrating Lymphocytes in Solid Tumors: A Practical Review for Pathologists and Proposal for a Standardized Method from the International Immunooncology Biomarkers Working Group: Part 1: Assessing the Host Immune Response, TILs in Invasiv", Advances in Anatomic Pathology, 24(5):235-251.
Hilscher et al. (May 12, 2020) "In Situ Sequencing: A High-Throughput, Multi-Targeted Gene Expression Profiling Technique for Cell Typing in Tissue Sections", Methods in Molecular Biology, vol. 2148, 313-329.
Ho, et al. (2019) "Dissection of Gastric Cancer Heterogeneity for Precision Oncology", Cancer Science, 110(11):3405-3414.
Huang, et al. (2020) "Identification of Immune Cell Infiltration and Immune-Related Genes in the Tumor Microenvironment of Glioblastomas", Frontiers in Immunology, 11:585034 (14 pages).
Hutter, et al. (Nov. 30, 2010) "Labeled Nucleoside Triphosphates with Reversibly Terminating Aminoalkoxyl Groups", Nucleosides Nucleotides Nucleic Acids, 29(11):879-895.
Iyer, et al. (Mar. 20, 2018) "Barcoded oligonucleotides ligated on RNA amplified for multiplex and parallel in-situ analyses", BioRxiv, 281121 (49 pages).
Ju, et al. (Dec. 26, 2006) "Four-color DNA Sequencing by Synthesis Using Cleavable Fluorescent Nucleotide Reversible Terminators", Proceedings of the National Academy of Sciences of the United States of America, 103(52):19635-19640.
Kawasaki, et al. (2014) "Toll-like Receptor Signaling Pathways", Frontiers in Immunology, 5:461 (9 pages).
Kim, et al. (2010) "Caseation of Human Tuberculosis Granulomascorrelates with Elevated Host Lipidmetabolism", EMBO Molecular Medicine, 2(7):258-274.
Klemm, et al. (2020) "Interrogation of the Microenvironmental Landscape in Brain Tumors Reveals Disease-Specific Alterations of Immune Cells", Cell, 181(7):1643-1660.
Krywkowski, et al. (2018) "Padlock Probes to Detect Single Nucleotide Polymorphisms", Methods in Molecular Biology, 1649:209-229.
Kumar, et al. (2012) "Peg-Labeled Nucleotides and Nanopore Detection for Single Molecule DNA Sequencing by Synthesis", Scientific Reports, 2:684(8 pages).
Lage, et al. (Feb. 2003) "Whole genome analysis of genetic alterations in small DNA samples using hyperbranched strand displacement amplification and array-CGH", Genome Research, 13(2):294-307.
Larsson, et al. (2004) "In situ Genotyping Individual DNA Molecules by Target-Primed Rolling-Circle Amplification of Padlock Probes", Nature Methods, 1(3):227-232.
Lehmann, et al. (Jul. 2011) "Identification of Human Triple-Negative Breast Cancer Subtypes and Preclinical Models for Selection of Targeted Therapies", The Journal of Clinical Investigation, 121(7):2750-2767.
Lizardi, et al. (Jul. 1998) "Mutation Detection and Single-Molecule Counting Using Isothermal Rolling-Circle Amplification", Nature Genetics, 19(3):225-232.
Lundin, et al. (2020) "Spatiotemporal Mapping of RNA Editing in the Developing Mouse Brain Using in Situ Sequencing Reveals Regional and Cell-type-specific Regulation", BMC Biology, 18(1):6.
Ma, et al. (2019) "Current Progress in CAR-T Cell Therapy for Solid Tumors", International Journal of Biological Sciences, 15(12):2548-2560.
Made, et al. (2020) "Presence of Genetic Variants Among Young Men With Severe COVID-19", JAMA, 324 (7):663-673.
Magaki, et al. (2019) "An Introduction to the Performance of Immunohistochemistry", Methods in Molecular Biology, 1897:289-298.
Manoharan, Vinothan N. (2010) "Digital Holographic Microscopy for 3D Imaging of Complex Fluids and Biological Systems", Frontiers of Engineering: Reports on Leading-edge Engineering from the 2009 Symposium, 8 pages.
Marakalala, et al. (2016) "Inflammatory Signaling in Human Tuberculosis Granulomas is Spatially Organized", Nature Medicine vol. 22(5):531-538.
McGranahan, et al. (2017) "Clonal Heterogeneity and Tumor Evolution: Past, Present, and the Future", Cell, 168(4):613-628.
Montemurro, et al. (2014) "Biomarkers of Drugs Targeting HER-family Signalling in Cancer", The Journal of Pathology, 232(2):219-229.
Moreno-Eutimio, et al. (2020) "Bioinformatic Analysis and Identification of Single-stranded RNA Sequences Recognized by TLR7/8 in the SARS-CoV-2, SARS-CoV, and MERS-CoV Genomes", Microbes and Infection, 22(4-5):226-229.
Ambardar, S. et al. (Dec. 2016, e-published Jul. 9, 2016). "High throughput sequencing: an overview of sequencing chemistry," *Indian journal of microbiology* 56: 394-404.
Agrawal, S. et al. (Nov. 15, 2016). "Nivolumab dose selection: challenges, opportunities, and lessons learned for cancer immunotherapy," *Journal of Immunotherapy Cancer* 4: 72.
Ahern, H. (1995) "Biochemical, reagent kits offer scientists good return on investment," *Scientist* 9(15): 20.
Alon, S. et al. (2020). "Expansion Sequencing: Spatially Precise In Situ Transcriptomics in Intact Biological Systems," *Science* 371(6528): eaax2656.
Arce, S. et al. (2013). "Fast and accurate automated cell boundary determination for fluorescence microscopy," *Sci Rep* 3: 2266.

(56) References Cited

OTHER PUBLICATIONS

Banér, J. et al. (Apr. 1, 005). "Analysis of T-cell receptor vβ gene repertoires after immune stimulation and in malignancy by use of padlock probes and microarrays," *Clinical chemistry* 51(4): 768-775.
Borkamo, E. D. et al. (Dec. 1, 2009, e-published Nov. 19, 2009). "cDNA microarray analysis of serially sampled cervical cancer specimens from patients treated with thermochemoradiotherapy," *International Journal of Radiation Oncology*Biology*Physics* 75(5): 1562-1569.
Bullinger, L. et al. (Apr. 15, 2004). "Use of gene-expression profiling to identify prognostic subclasses in adult acute myeloid leukemia," *New England Journal of Medicine* 350(16): 1605-1616.
Carow, B. et al. (2019). "Spatial and temporal localization of immune transcripts defines hallmarks and diversity in the tuberculosis granuloma," *Nature Communications* 10(1): 1823.
Carpenter, A. E. et al.(2006, e-published Oct. 31, 2016). "CellProfiler: image analysis software for identifying and quantifying cell phenotypes," *Genome Biology* 7(10) :R100.
Catuogno, S. et al. (Apr. 8, 2011). "Recent advance in biosensors for microRNAs detection in cancer," *Cancers* 3(2): 1877-1898.
Chen, F. et al. (Jan. 30, 2015, e-published Jan. 15, 2015). "Optical imaging. Expansion microscopy," *Science* 347(6221): 543-548.
Chen, K. H. et al. (Apr. 24, 2015, e-published Apr. 9, 2015). "RNA imaging. Spatially resolved, highly multiplexed RNA profiling in single cells," *Science* 348(6233): aaa6090.
Chen, X. et al. (Feb. 28, 2018, e-published Nov. 28, 2017). "Efficient in situ barcode sequencing using padlock probe-based BaristaSeq," *Nucleic acids research* 46(4): Article e22, pp. 1-10.
Christian, A. T. et al. (Dec. 4, 2001, e-published Nov. 27, 2001). "Detection of DNA point mutations and mRNA expression levels by rolling circle amplification in individual cells," *PNAS USA* 98(25): 14238-14243.
Conze, T. et al. (Jul. 2009, e-published Feb. 19, 2009). "Analysis of genes, transcripts, and proteins via DNA ligation," *Annual review of analytical chemistry* 2(1): 215-239.
Costea, P. I. et al. (Mar. 4, 2013). "TagGD: fast and accurate software for DNA Tag generation and demultiplexing," *PLoS One* 8(3): e57521.
Daigeler, A. et al. (Jul. 6, 2006). "Clinicopathological findings in a case series of extrathoracic solitary fibrous tumors of soft tissues," *BMC surgery* 6: 1-8.
Denkert, C. et al. (Nov. 1, 2015, e-published Aug. 14, 2015). "Strategies for developing Ki67 as a useful biomarker in breast cancer," *The Breast* 24: S67-S72.
Edelman, M. J. et al. (May 1997, e-published Feb. 28, 2002). "The utility of follow-up testing after curative cancer therapy: a critical review and economic analysis," *Journal of general internal medicine* 12(5): 318-331.
El-Sagheer, A. H. et al. (Aug. 21, 2012, e-published Mar. 22, 2012)."Click nucleic acid ligation: applications in biology and nanotechnology," *Accounts of chemical research* 45(8):1258-1267.
Extended European Search Report mailed Mar. 18, 2024, for EP Application No. 21852670.5, 13 pages.
Fijnvandraat, A. C. et al. (Sep. 1, 2002, e-published Sep. 10, 2002). "Nonradioactive in situ detection of mRNA in ES cell-derived cardiomyocytes and in the developing heart," *Microscopy research and technique* 58(5): 387-394.
Frances-Soriano, L. et al. (Jan. 26, 2021, e-published Dec. 28, 2020). "In Situ rolling circle amplification Forster resonance energy transfer (RCA-FRET) for washing-free real-time single-protein imaging," *Analytical Chemistry* 93(3): 1842-1850.
Frank, D. N. (Oct. 29, 2009). "Barcrawl and Bartab: software tools for the design and implementation of barcoded primers for highly multiplexed DNA sequencing," *BMC bioinformatics* 10(1): 1-13.
Fredriksson, S. et al. (Apr. 2007, e-published Mar. 18, 2007). "Multiplexed protein detection by proximity ligation for cancer biomarker validation," *Nature methods* 4(4): 327-329.
Fredriksson, S. et al. (May 1, 2002). "Protein detection using proximity-dependent DNA ligation assays," *Nature biotechnology* 20(5): 473-477.
Gao, H. et al. (Dec. 2019, e-published Oct. 17, 2019). "Rolling circle amplification for single cell analysis and in situ sequencing," *TrAC Trends in Analytical Chemistry* 121: 115700.
Garmendia, C. et al. (Feb. 1992). "The bacteriophage phi 29 DNA polymerase, a proofreading enzyme," *Journal of Biological Chemistry* 267(4): 2594-2599.
Gelali, E. et al. (Apr. 9, 2019). "iFISH is a publically available resource enabling versatile DNA FISH to study genome architecture," *Nat Commun* 10(1): 1636.
Gore, A. et al. (Mar. 3, 2011). "Somatic coding mutations in human induced pluripotent stem cells," *Nature* 471 (7336): 63-67.
Gullberg, M. et al. (May 21, 2004). "Cytokine detection by antibody-based proximity ligation," *PNAS* 101(22): 8420-8424.
Guo, J. et al. (Jul. 8, 2008, e-published Jun. 30, 2008). "Four-color DNA sequencing with 3'-O-modified nucleotide reversible terminators and chemically cleavable fluorescent dideoxynucleotides," *PNAS USA* 105(27): 9145-9150.
Gyllborg, D. et al. (Nov. 4, 2020). "Hybridization-based in situ sequencing (HybISS) for spatially resolved transcriptomics in human and mouse brain tissue," *Nucleic Acids Research* 48(19): e112.
Hagai, T. et al. (Nov. 2018, e-published Oct. 24, 2018). "Gene expression variability across cells and species shapes innate immunity," *Nature* 563(7730): 197-202.
Hamaday, M. et al. (Mar. 2008) "Error-correcting barcoded primers for pyrosequencing hundreds of samples in multiplex," *Nature Methods* 5(3): 235.
Hamilton, N. (2009) "Quantification and its applications in fluorescent microscopy imaging." *Traffic* 10(8): 951-961.
Hardenbol, P. et al. (2003) "Multiplexed genotyping with sequence-tagged molecular inversion probes." *Nature biotechnology* 21(6): 673-678.
Heintzmann, R. et al. (Dec. 13, 2017, e-published Nov. 10, 2017). "Super-Resolution Structured Illumination Microscopy," *Chem. Rev.* 117(23): 13890-13908.
Hu, Y. et al. (2014) "Sensitive quantification of messenger RNA with a real-time ligase chain reaction by using a ribonucleotide-modified DNA probe." *Chemical Communications* 50(86): 13093-13095.
International Search Report and Written Opinion mailed on Nov. 23, 2021, for PCT Application No. PCT/US2021/045104, filed Aug. 6, 2021, 15 pages.
International Search Report & Written Opinion mailed on Jan. 31, 2022, for PCT Application No. PCT/US2021/045105, filed Aug. 6, 2022, 18 pages.
International Search Report & Written Opinion mailed on Sep. 19, 2022, for PCT Application No. PCT/US2022/027630, filed May 4, 2022, 14 pages.
Jeong, S. et al. (Apr. 2020, e-published Jan. 30, 2020). "Current immunoassay methods and their applications to clinically used biomarkers of breast cancer," *Clinical biochemistry* 78: 43-57.
Kappler, K. et al. (Aug. 2020, e-published Aug. 5, 2020). "Emergence and significance of carbohydrate-specific antibodies," *Genes Immun* 21(4): 224-239.
Ke, R. et al. (Sep. 2013, e-published Jul. 14, 2013) "In situ sequencing for RNA analysis in preserved tissue and cells." *Nature methods* 10(9): 857-860.
Klein A. M., et al. (Jul. 25, 2017). "InDrops and Drop-seq technologies for single-cell sequencing," *Lab Chip* 17(15): 2540-2541.
Kobori, T. et al. (2014) "Expanding possibilities of rolling circle amplification as a biosensing platform," *Analytical Sciences* 30(1): 59-64.
Kohman, R. E. et al. (Apr. 28, 2020). "Fluorescent in situ sequencing of DNA barcoded antibodies," *bioRxiv* Apr. 2020.
Konry, T. et al. (Feb. 7, 2011, e-published Dec. 27, 2010). "Ultrasensitive detection of low-abundance surface-marker protein using isothermal rolling circle amplification in a microfluidic nanoliter platform," *Small* 7(3): 395-400.
Krzywkowski, T. et al. (Oct. 2018). "Chimeric padlock and iLock probes for increased efficiency of targeted RNA detection," *RNA* 25(1): 82-89.

(56) References Cited

OTHER PUBLICATIONS

Lareau, C. A., et al. (Feb. 13, 2020). "Inference and effects of barcode multiplets in droplet-based single-cell assays," *Nature Communications* 11(1): 866.
Larimore, K. et al. (Sep. 15, 2012). "Shaping of human germline IgH repertoires revealed by deep sequencing," *The Journal of Immunology* 189(6): 3221-3230.
Larsson, C. et al., (May 2010, e-published Apr. 11, 2010). "In situ detection and genotyping of individual mRNA molecules," *Nature Methods* 7(5): 395-397.
Lee, J. H. et al. (e-published Feb. 12, 2015). "Fluorescent in situ sequencing (FISSEQ) of RNA for gene expression profiling in intact cells and tissues," *Nature protocols* 10(3): 442-458.
Lee, J. H. et al. (Feb. 27, 2014, e-published Feb. 20, 2014). "Highly multiplexed subcellular RNA sequencing in situ," *Science* 343(6177): 1360-1363.
Li, J. B. et al. (Sep. 2009, e-published Jun. 12, 2009). Multiplex padlock targeted sequencing reveals human hypermutable CpG variations, *GenomeRes* 19(9): 1606-1615.
Li, J. B. et al. (May 29, 2009). "Genome-wide identification of human RNA editing sites by parallel DNA capturing and sequencing," *Science* 324(5931): 1210-1213.
Li, N. et al. (May 21, 2009) "Stand-alone rolling circle amplification combined with capillary electrophoresis for specific detection of small RNA." *Analytical chemistry* 81(12): 4906-4913.
Lubeck, E. et al. (Jul. 2012, e-published Jun. 3, 2012). "Single-cell systems biology by super-resolution imaging and combinatorial labeling," *Nature methods* 9(7): 743-748.
Lubeck, E. et al. (Apr. 2014, e-published Mar. 28, 2014). "Single-cell in situ RNA profiling by sequential hybridization," *Nature methods* 11(4): 360-361.
Manuguerra I. et al. (May 1, 2018). "Gene assembly via one-pot chemical ligation of DNA promoted by DNA nanostructures," *Chem Commun(Camb)* 54(36): 4529-4532.
Mignardi, M. et al. (Apr. 28, 2014). "Fourth-generation sequencing in the cell and the clinic," *Genome medicine* 6: 1-4.
Mitra, R.D. et al. (2003) "Fluorescent in situ sequencing on polymerase colonies." *Analytical biochemistry* 320(1): 55-65.
Mohammadi-Kambs, M. et al. (2017) "Hamming distance as a concept in DNA molecular recognition." *ACS omega* 2(4): 1302-1308.
Nilsson, M. et al. (Sep. 30, 1994). "Padlock probes: circularizing oligonucleotides for localized DNA detection," *Science* 265 (5181) :2085-2088.
Nitta, H. et al. (Aug. 2013, e-published Nov. 15, 2015). "New methods for ALK status diagnosis in non-small-Cell lung Cancer: an improved ALK immunohistochemical assay and a new, Brightfield, dual ALK IHC—In situ hybridization assay," *Journal of Thoracic Oncology* 8(8): 1019-1031.
Odeh, F., et al. (Dec. 18, 2019). "Aptamers Chemistry: Chemical Modifications and Conjugation Strategies," *Molecules* (Basel, Switzerland) 25(1): 3.
Ouladan, S. et al. (Jun. 2015, e-published Apr. 20, 2015). "Differential diagnosis of solitary fibrous tumors: A study of 454 soft tissue tumors indicating the diagnostic value of nuclear STAT6 relocation and ALDH1 expression combined with in situ proximity ligation assay," *International journal of oncology* 46(6): 2595-2605.
Park, M. S. et al. (May 11, 2013). "The role of chemotherapy in advanced solitary fibrous tumors: a retrospective analysis," *Clinical sarcoma research* 3(1): 1-7.
Patel, A. P. et al. (Jun. 20, 2014, e-published Jun. 12, 2014). "Single-cell RNA-seq highlights intratumoral heterogeneity in primary glioblastoma," *Science* 344(6190): 1396-1401.
Payne, A. C. (Jun. 2017, e-published Jul. 31, 2017). "Towards sequencing by synthesis in situ. Doctoral Dissertation." *Massachusetts Institute of Technology*, 55 pages.
Pearson, A. et al. (Aug. 2016, e-published May 13, 2016). "High-Level Clonal FGFR Amplification and Response to FGFR Inhibition in a Translational Clinical Trial," *CancerDiscov* 6(8): 838-851.
Peerzade, S. A. et al. (May 8, 2020). "Ultrabright Fluorescent Silica Nanoparticles for Multiplexed Detection," *Nanomaterials* 10(5): 905.
Peters, J. M. et al. (Jan. 2011). "Multiparameter flow cytometry in the diagnosis and management of acute leukemia," *ArchPathol Lab Med* 135(1): 44-54.
Porreca, G. J. et al. (Nov. 2007, e-published Oct. 14, 2007). "Multiplex amplification of large sets of human exons," *Nat Methods* 4(11): 931-936.
Rouhanifard, S. H., et al. (2018) "Exponential fluorescent amplification of individual RNAs using clampFISH probes." *bioRxiv*, Article 222794.
Roussis, I. M. et al. (Mar. 3, 2017). "RNA whole-mount in situ hybridization proximity ligation assay (rISH-PLA), an assay for detecting RNA-protein complexes in intact cells," *Current protocols in cell biology* 74(1): 17-20.
Sansone, A. (Jun. 2019). "Spatial transcriptomics levels up," *NatMethods* 16(6): 458.
Sapoznik, E. et al. (Nov. 12, 2020). "A versatile oblique plane microscope for large-scale and high-resolution imaging of subcellular dynamics," *eLife* 9: e57681.
Schallmeiner, E. et al. (Feb. 1, 2007, e-published Dec. 17, 2006). "Sensitive protein detection via triple-binder proximity ligation assays," *Nature methods* 4(2): 135-137.
Schlachter, S. et al. (2009). "A method to unmix multiple fluorophores in microscopy images with minimal a priori information," *OptExpress* 17(25): 22747-22760.
Shirakawa, H. et al. (Mar. 2004). "Blind spectral decomposition of single-cell fluorescence by parallel factor analysis," *Biophysical Journal* 86(3): 1739-1752.
Söderberg, O et al. (Dec. 2006, e-published Oct. 29, 2006). "Direct observation of individual endogenous protein complexes in situ by proximity ligation," *Nature methods* 3(12): 995-1000.
Stratagene Catalog, The (1988). p. 39.
Strell, C. et al. (Apr. 2019, e-published Mar. 14, 2019). "Placing RNA in context and space-methods for spatially resolved transcriptomics," *The FEBS journal* 286(8): 1468-1481.
Suzuki, A. et al. (Dec. 20, 2019). "Characterization of cancer omics and drug perturbations in panels of lung cancer cells," *Sci. Rep* 9(1): 19529.
Takahashi, H. et al. (2018) "RNase H-assisted RNA-primed rolling circle amplification for targeted RNA sequence detection." *Scientific reports* 8: 1-11.
Tang, S. et al. (Aug. 2, 2016). "Suppression of rolling circle amplification by nucleotide analogs in circular template for three DNA polymerases," *Bioscience, Biotechnology, and Biochemistry* 80(8): 1555-1561.
Turczyk, B. M. et al. (Jul. 2020). "Spatial sequencing: a perspective," *Journal of Biomolecular Technique* 31(2): 44.
Vickovic, S.et al. (Oct. 2019, e-published Sep. 9, 2019). "High-definition spatial transcriptomics for in situ tissue profiling," *Nat. Methods* 16(10): 987-990.
Wahlestedt, C. et al. (May 9, 2000). "Potent and nontoxic antisense oligonucleotides containing locked nucleic acids," *PNAS* 97(10): 5633-5638.
Wang, G. et al. (Mar. 19, 2018). "Multiplexed imaging of high-density libraries of RNAs with MERFISH and expansion microscopy," *SciRep* 8(1): 4847.
Wang X. et al. (Jul. 27, 2018, e-published Jun. 21, 2018). "Three-dimensional intact-tissue sequencing of single-cell transcriptional states," *Science* 361(6400): eaat5691.
Wassie, A. T. et al. (e-published Dec. 20, 2018). "Expansion microscopy: principles and uses in biological research," *Nature methods* 16(1): 33-41.
Weibrecht, I. et al. (Jan. 2013) "In situ detection of individual mRNA molecules and protein complexes or post-translational modifications using padlock probes combined with the in situ proximity ligation assay." *Nature protocols* 8(2): 355-372.
Wilson, C. S. et al. (Jul. 15, 2006, e-published Apr. 4, 2006). "Gene expression profiling of adult acute myeloid leukemia identifies novel biologic clusters for risk classification and outcome prediction," *Blood* 108(2): 685-696.

(56) References Cited

OTHER PUBLICATIONS

Xu, Q. et al. (2009) "Design of 240,000 orthogonal 25mer DNA barcode probes." *PNAS* 106(7): 2289-2294.
You, Y. et al. (Apr. 1, 2006, e-published Jan. 1, 2006). "Design of LNA probes that improve mismatch discrimination," *Nucleic acids research* 34(8): e60-e60.
York, A. G. et al. (Nov. 2013, e-published Oct. 6, 2013). "Instant super-resolution imaging in live cells and embryos via analog image processing," *Nature Methods* 10(11): 1122-1126.
Zhang, D. et al. (Jan. 2006, e-published Aug. 24, 2005). "Amplification of circularizable probes for the detection of target nucleic acids and proteins," *Clinica chimica acta* 363(1-2): 61-70.
Zhang, K. et al. (Aug. 2009, e-published Jul. 20, 2009). "Digital RNA allelotyping reveals tissue-specific and allele-specific gene expression in human," *Nature Methods* 6(8): 613-618.
Zheng, G. X. et al. (Jan. 16, 2017). "Massively parallel digital transcriptional profiling of single cells," *NatComm* 8: 14049.
Anastasi et al. (Jan. 1990) "Detection of Numerical Chromosomal Abnormalities in Neoplastic Hematopoietic Cells by in situ Hybridization with a Chromosome-Specific Probe", American Journal of Pathology, 136(1): 131-139.
Lishner et al. (1996) "Trisomies 9 and 8 detected by Fluorescence in situ Hybridization in Patients with Systemic Mastocytosis", The Journal of Allergy and Clinical Immunology, 98:199-204.
Moqbel et al. (1991) "Expression of mRNA and Immunoreactivity for the Granulocyte/Macrophage Colony-stimulating Factor in Activated Human Eosinophils", Journal of Experimental Medicine, 174:749-752.
Pinkel et al. (1986) "Cytogenetic Analysis by In Situ Hybridization with Fluorescently Labeled Nucleic Acid Probes", Cold Spring Harbor Symposia on Quantitative Biology, 51:151-157.
Thompson, Joanne (2002) "In Situ Detection of RNA in Blood- and Mosquito-Stage Malaria Parasites", Malaria Methods and Protocols, 72:225-226 (11 pages).
Wagner et al. (1998) "In situ Detection of a Virulence Factor mRNA and 16S rRNA in Listeria Monocytogenes", FEMS Microbiology Letters, 160:159-168.
Ehlers et al. (Jan. 7, 2013) "The Granuloma in Tuberculosis: Dynamics of a Host-pathogen Collusion", Frontiers in Immunology, 3:411 (9 pages).

* cited by examiner

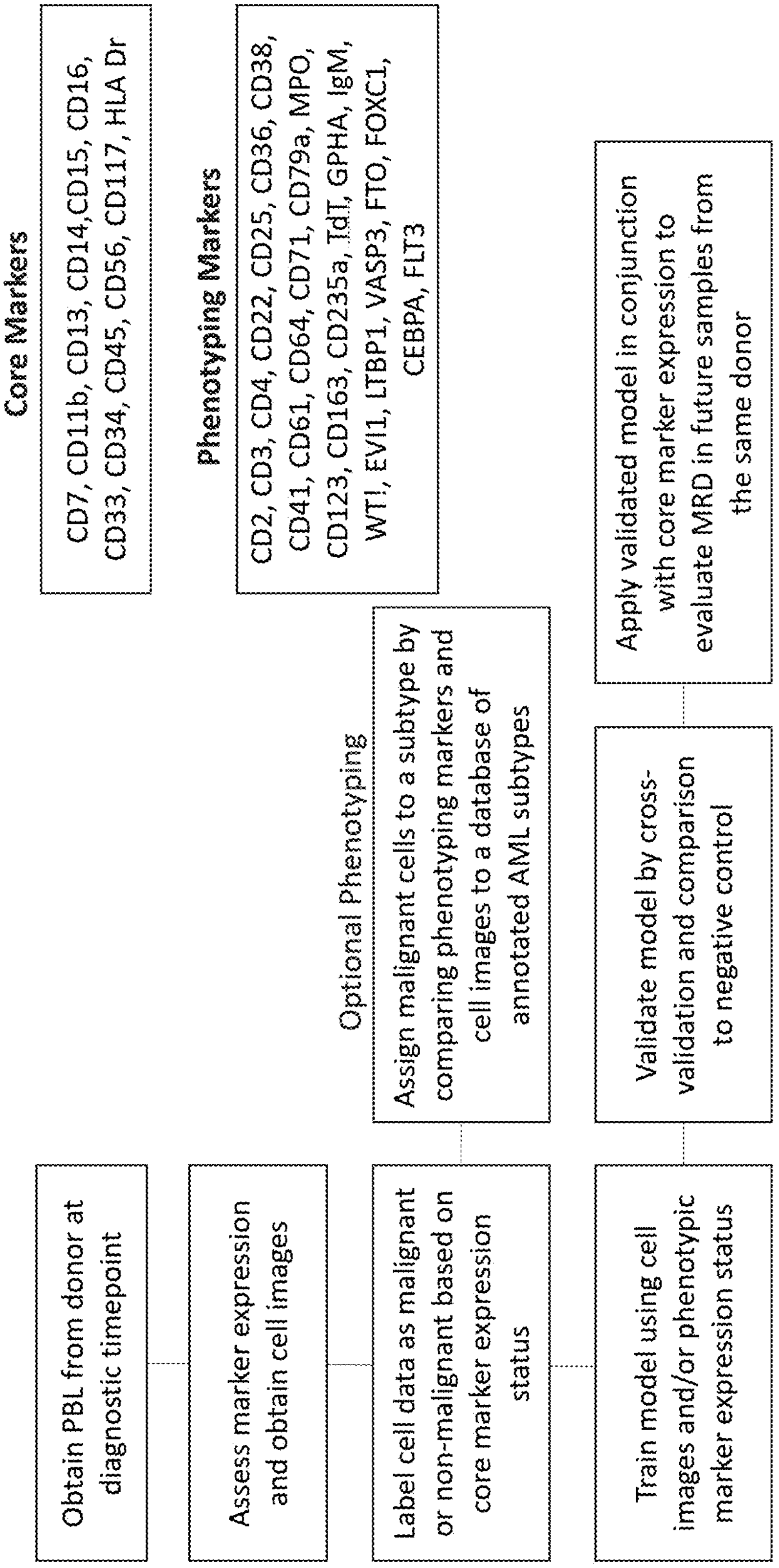

FIG. 7

Core Markers

CD7, CD11b, CD13, CD14, CD15, CD16, CD33, CD34, CD45, CD56, CD117, HLA Dr

Phenotyping Markers

CD2, CD3, CD4, CD22, CD25, CD36, CD38, CD41, CD61, CD64, CD71, CD79a, MPO, CD123, CD163, CD235a, TdT, GPHA, IgM, WT1, EVI1, LTBP1, VASP3, FTO, FOXC1, CEBPA, FLT3

Obtain PBL from donor at diagnostic timepoint

Assess marker expression and obtain cell images

Label cell data as malignant or non-malignant based on core marker expression status Train model using cell images and/or phenotypic marker expression status Optional Phenotyping Assign malignant cells to a subtype by comparing phenotyping markers and cell images to a database of annotated AML subtypes Validate model by cross-validation and comparison to negative control Apply validated model in conjunction with core marker expression to evaluate MRD in future samples from the same donor

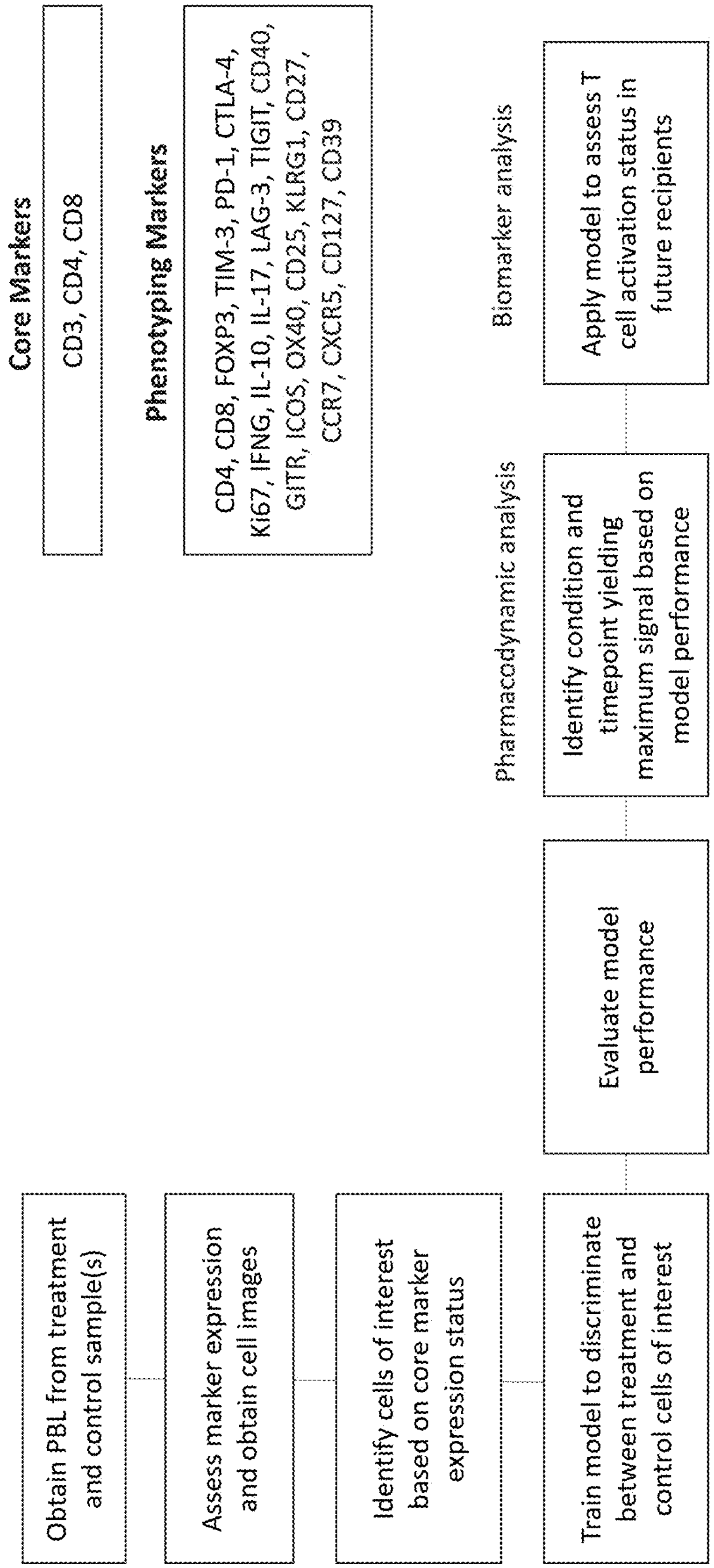

FIG. 8

Core Markers

CD3, CD4, CD8

Phenotyping Markers

CD4, CD8, FOXP3, TIM-3, PD-1, CTLA-4, Ki67, IFNG, IL-10, IL-17, LAG-3, TIGIT, CD40, GITR, ICOS, OX40, CD25, KLRG1, CD27, CCR7, CXCR5, CD127, CD39

Obtain PBL from treatment and control sample(s)

Assess marker expression and obtain cell images

Identify cells of interest based on core marker expression status

Train model to discriminate between treatment and control cells of interest

Evaluate model performance

Pharmacodynamic analysis

Identify condition and timepoint yielding maximum signal based on model performance Biomarker analysis Apply model to assess T cell activation status in future recipients

FIG. 9

| Drug Dose | Model AUC at Timepoint | | | | |
|---|---|---|---|---|---|
| | day 0 | 1 hr | 1 day | 10 days | 30 days |
| 0.1 mg/kg | 0.50 | 0.50 | 0.50 | 0.50 | 0.50 |
| 0.3 mg/kg | 0.50 | 0.50 | 0.50 | 0.52 | 0.50 |
| 1 mg/kg | 0.50 | 0.51 | 0.55 | 0.60 | 0.52 |
| 3 mg/kg | 0.50 | 0.53 | 0.62 | 0.81 | 0.56 |
| 10 mg/kg | 0.50 | 0.54 | 0.62 | 0.80 | 0.55 |

METHODS FOR IN SITU TRANSCRIPTOMICS AND PROTEOMICS

CROSS-REFERENCES TO RELATED APPLICATIONS

This application is a divisional application of U.S. patent application Ser. No. 18/443,079, filed Feb. 15, 2024, which is a continuation of U.S. patent application Ser. No. 17/938,329, filed Oct. 5, 2022, which is a continuation of U.S. patent application Ser. No. 17/816,841, filed Aug. 2, 2022, which is a continuation of U.S. patent application Ser. No. 17/840,473, filed Jun. 14, 2022, now issued as U.S. Pat. No. 11,891,656, which is a continuation of U.S. patent application Ser. No. 17/840,469, filed Jun. 14, 2022, now issued as U.S. Pat. No. 11,643,679, which is a continuation of U.S. patent application Ser. No. 17/396,575, filed Aug. 6, 2021, now issued as U.S. Pat. No. 11,492,662, which claims the benefit of U.S. Provisional Application No. 63/062,054, filed Aug. 6, 2020; U.S. Provisional Application No. 63/140,700, filed Jan. 22, 2021; and U.S. Provisional Application No. 63/209,886, filed Jun. 11, 2021; each of which are incorporated herein by reference in their entirety and for all purposes.

BACKGROUND

Single-cell technologies have emerged to enable profiling the composition of the genome, epigenome, transcriptome, or proteome of a single cell. Uncovering the distribution, heterogeneity, spatial gene and protein co-expression patterns within cells and tissues is vital for understanding how cell co-localization influences tissue development and the spread of diseases such as cancer, which could lead to important new discoveries and therapeutics. Quantifying gene and protein expression enables precise identification, monitoring, and possible treatment at the molecular level. Disclosed herein, inter alia, are solutions to these and other problems in the art.

BRIEF SUMMARY

In an aspect is provided a method of detecting a plurality of different targets within an optically resolved volume of a cell in situ. In embodiments, the method includes i) associating a different oligonucleotide barcode from a known set of barcodes with each of the plurality of targets; ii) sequencing each barcode to obtain a multiplexed signal in the cell in situ; iii) demultiplexing the multiplexed signal by comparison with the known set of barcodes; and detecting the plurality of targets by identifying the associated barcodes detected in the cell.

In an aspect is provided a method of identifying a cell that responds to a genetically modifying agent, the method including administering a genetically modifying agent to the cell, detecting whether an agent-mediated nucleic acid sequence is present in the cell by detecting a plurality of different targets within an optically resolved volume of a cell in situ, according to the methods described herein, including embodiments, and identifying a cell that responds to a genetically modifying agent when the presence of the agent-mediated nucleic acid is detected in the cell.

In an aspect is provided a method of identifying an agent as a genetically modifying agent, the method including administering an agent to a cell, detecting whether an agent-mediated nucleic acid sequence is present in the cell by detecting a plurality of different targets within an optically resolved volume of a cell in situ, according to the methods described herein, including embodiments, and identifying the genetically modifying agent when the presence of the agent-mediated nucleic acid is detected in the cell.

BRIEF DESCRIPTION OF THE DRAWINGS

As shown in FIG. 1B, the padlock probe is primed across the ligation site (i.e., an amplification primer hybridizes to both the 3' and 5' ends of the padlock probe) and amplified to produce an amplicon. Alternatively, as shown in FIG. 1C, the padlock probe is primed at a region within the padlock probe (i.e., an amplification primer hybridizes a region of the padlock probe) and amplified to produce an amplicon. Here, the ligation site is depicted as a dashed line. The amplicon is primed with a sequencing primer and subjected to a sequencing process, whereby the identity of the oligonucleotide barcode is obtained, as illustrated in FIG. 1D. FIG. 1E shows the original cell wherein one resolved pixel (depicted by the dotted box) includes a plurality of amplicons.

FIG. 5A is a cartoon representation of two padlock probe molecules, Probe 1 and Probe 2, that contain combinations of multiple primer binding sites. The combinations are introduced in the padlock probes, as described herein. A first circular polynucleotide, labeled Probe 1 in FIG. 5A, includes a first primer binding site (a nucleic acid sequence complementary to a first sequencing primer, labeled Primer 1) before a barcode (labeled as Barcode 1), and a second primer binding site (a nucleic acid sequence complementary to a second sequencing primer, labeled Primer 2) before another instance of the same barcode (also labeled as Barcode 1). The primer binding sites (i.e., Primer 1 and Primer 2) are different from each other such that the first primer will not hybridize to the second primer binding site, and vice versa. A second circular polynucleotide, labeled Probe 2 in FIG. 5A, includes a first primer binding site (a nucleic acid sequence complementary to a first sequencing primer, labeled Primer 1) before a barcode (labeled as Barcode 1), and a third primer binding site (a nucleic acid sequence complementary to a third sequencing primer, labeled Primer 3) before another instance of the same barcode (also labeled as Barcode 1). The primer binding sites (i.e., primer 1, primer 2, and primer 3) are different from each other such that the first primer will not hybridize to the second primer binding site or the third primer binding site, the second primer will not hybridize to the first primer binding site or the third primer binding site, and the third primer will not hybridize to the first primer binding site or the second primer binding site under reaction conditions according to an embodiment. In this example, two circularized and amplified probes (e.g., Probe 1 and Probe 2) bound to overlapping transcripts in a voxel are targeted by a set of 3 primers (i.e., a primer set of 3). During the first round of sequencing, using primer 1, the two transcripts are unresolvable, as the first instance of Barcode 1 in each of Probe 1 and Probe 2 would be sequenced. However, in the second round of sequencing, primer 2 can hybridize and sequence the second instance of Barcode 1 in Probe 1. Similarly, in the third round of sequencing primer 3 can hybridize and sequence the second instance of Barcode 1 in Probe 2. By such iterative means, two otherwise overlapping RNA transcripts are resolved. FIG. 5B is a flowchart outlining an example using the iterative multiplexed primer sequencing method described herein. FIG. 5B describes padlock probe hybridization, ligation, and amplification, followed by hybridizing the first primer (Primer 1) and sequencing of the first barcode to a sufficient read length (e.g., the entirety of the barcode). In embodiments, a gap between the two feet of the padlock probe is filled by polymerase extension prior to ligation and amplification (not shown). Optionally, the sequencing cycle is terminated (e.g., incorporating dideoxynucleotides triphosphates (ddNTPs)). This process is repeated for the second and third barcodes, up to N number of primers in the set of primers.

FIG. 7 provides an embodiment of a method for MRD assessment of AML using marker gene status and cell imaging.

FIG. 8 provides an embodiment of a method for pharmacodynamic and biomarker analysis of a T-cell modulating immunotherapy.

FIG. 9. Pharmacodynamic analysis of a T-cell modulating immunotherapy using model performance as a Metric-of-Agent activity.

FIG. 11B labels the overall footprint of the complementary, hybridized sequences, 30 and 31, in the V and J region, respectively.

DETAILED DESCRIPTION

Figure 1A:
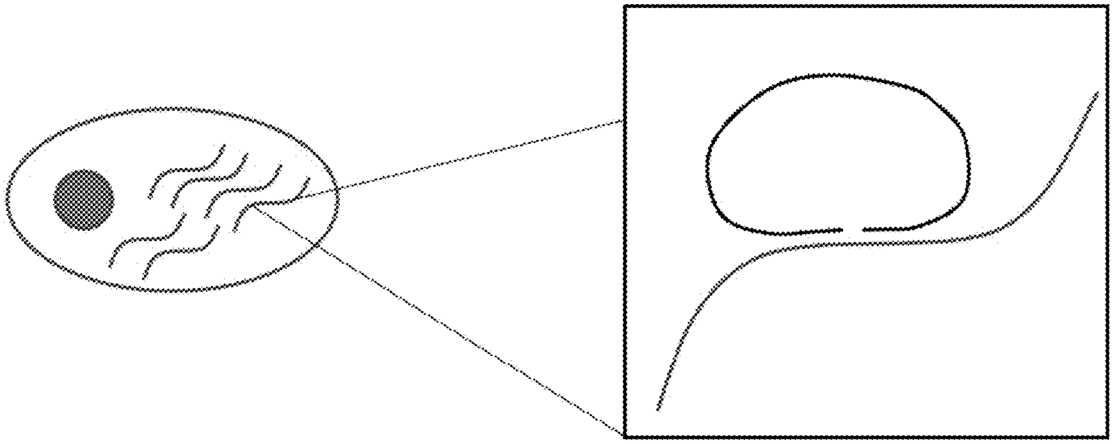
FIGS. 1A-1E. A cartoon depiction of a cell that is attached to a surface, and is also fixed (e.g., using a fixing agent) and permeabilized according to known methods is illustrated in FIG. 1A. The cell may have been cultured on the surface, or the cell may have been initially cultured in suspension and then fixed to the surface. The RNA present in the cell (depicted as a wavy line) is subjected to an amplification technique where a targeted padlock probe which contains an oligonucleotide barcode (e.g., 10-15 nucleotides) hybridizes on the RNA. Following padlock probe ligation, the excess content is washed away (e.g., unhybridized padlock probes).

The aspects and embodiments described herein relate to systems and methods for analyzing a cell and cellular components (e.g., RNA transcripts, proteins, or analytes). Data obtained from the proteome and transcriptome is used in research to gain insight into processes such as cellular differentiation, carcinogenesis, transcription regulation, and biomarker discovery, among others.

I. Definitions

The practice of the technology described herein will employ, unless indicated specifically to the contrary, conventional methods of chemistry, biochemistry, organic chemistry, molecular biology, bioinformatics, microbiology, recombinant DNA techniques, genetics, immunology, and cell biology that are within the skill of the art, many of which are described below for the purpose of illustration. Examples of such techniques are available in the literature. See, e.g., Singleton et al., DICTIONARY OF MICROBIOLOGY AND MOLECULAR BIOLOGY 2nd ed., J. Wiley & Sons (New York, NY 1994); and Sambrook and Green, Molecular Cloning: A Laboratory Manual, 4th Edition (2012). Methods, devices, and materials similar or equivalent to those described herein can be used in the practice of embodiments of this invention.

All patents, patent applications, articles and publications mentioned herein, both supra and infra, are hereby expressly incorporated herein by reference in their entireties.

Unless defined otherwise herein, all technical and scientific terms used herein have the same meaning as commonly understood by one of ordinary skill in the art to which this disclosure belongs. Various scientific dictionaries that include the terms included herein are well known and available to those in the art. Although any methods and materials similar or equivalent to those described herein find use in the practice or testing of the disclosure, some preferred methods and materials are described. Accordingly, the terms defined immediately below are more fully described by reference to the specification as a whole. It is to be understood that this disclosure is not limited to the particular methodology, protocols, and reagents described, as these may vary, depending upon the context in which they are used by those of skill in the art. The following definitions are provided to facilitate understanding of certain terms used frequently herein and are not meant to limit the scope of the present disclosure.

As used herein, the singular terms “a”, “an”, and “the” include the plural reference unless the context clearly indicates otherwise. Reference throughout this specification to, for example, “one embodiment”, “an embodiment”, “another embodiment”, “a particular embodiment”, “a related embodiment”, “a certain embodiment”, “an additional embodiment”, or “a further embodiment” or combinations thereof means that a particular feature, structure or characteristic described in connection with the embodiment is included in at least one embodiment of the present disclosure. Thus, the appearances of the foregoing phrases in various places throughout this specification are not necessarily all referring to the same embodiment. Furthermore, the particular features, structures, or characteristics may be combined in any suitable manner in one or more embodiments.

As used herein, the term “about” means a range of values including the specified value, which a person of ordinary skill in the art would consider reasonably similar to the specified value. In embodiments, the term “about” means within a standard deviation using measurements generally acceptable in the art. In embodiments, about means a range extending to +/−10% of the specified value. In embodiments, about means the specified value.

Throughout this specification, unless the context requires otherwise, the words “comprise”, “comprises” and “comprising” will be understood to imply the inclusion of a stated step or element or group of steps or elements but not the exclusion of any other step or element or group of steps or elements. By “consisting of” is meant including, and limited to, whatever follows the phrase “consisting of.” Thus, the phrase “consisting of” indicates that the listed elements are required or mandatory, and that no other elements may be present. By “consisting essentially of” is meant including any elements listed after the phrase, and limited to other elements that do not interfere with or contribute to the activity or action specified in the disclosure for the listed elements. Thus, the phrase “consisting essentially of” indicates that the listed elements are required or mandatory, but that no other elements are optional and may or may not be present depending upon whether or not they affect the activity or action of the listed elements.

As used herein, the term “associated” or “associated with” can mean that two or more species are identifiable as being co-located at a point in time. An association can mean that two or more species are or were within a similar container. An association can be an informatics association, where for example digital information regarding two or more species is stored and can be used to determine that one or more of the species were co-located at a point in time. An association can also be a physical association. In some instances two or more associated species are “tethered”, “coated”, "attached", or "immobilized" to one another or to a common solid or semisolid support. An association may refer to a relationship, or connection, between two entities. Associated may refer to the relationship between a sample and the DNA molecules, RNA molecules, or polynucleotides originating from or derived from that sample. These relationships may be encoded in oligonucleotide barcodes, as described herein. A polynucleotide is associated with a sample if it is an endogenous polynucleotide, i.e., it occurs in the sample at the time the sample is obtained, or is derived from an endogenous polynucleotide. For example, the RNAs endogenous to a cell are associated with that cell. cDNAs resulting from reverse transcription of these RNAs, and DNA amplicons resulting from PCR amplification of the cDNAs, contain the sequences of the RNAs and are also associated with the cell. The polynucleotides associated with a sample need not be located or synthesized in the sample, and are considered associated with the sample even after the sample has been destroyed (for example, after a cell has been lysed). Barcoding can be used to determine which polynucleotides in a mixture are associated with a particular sample.

As used herein, the term "complementary" or "substantially complementary" refers to the hybridization, base pairing, or the formation of a duplex between nucleotides or nucleic acids. For example, complementarity exists between the two strands of a double stranded DNA molecule or between an oligonucleotide primer and a primer binding site on a single stranded nucleic acid when a nucleotide (e.g., RNA or DNA) or a sequence of nucleotides is capable of base pairing with a respective cognate nucleotide or cognate sequence of nucleotides. As described herein and commonly known in the art the complementary (matching) nucleotide of adenosine (A) is thymidine (T) and the complementary (matching) nucleotide of guanosine (G) is cytosine (C). Thus, a complement may include a sequence of nucleotides that base pair with corresponding complementary nucleotides of a second nucleic acid sequence. The nucleotides of a complement may partially or completely match the nucleotides of the second nucleic acid sequence. Where the nucleotides of the complement completely match each nucleotide of the second nucleic acid sequence, the complement forms base pairs with each nucleotide of the second nucleic acid sequence. Where the nucleotides of the complement partially match the nucleotides of the second nucleic acid sequence only some of the nucleotides of the complement form base pairs with nucleotides of the second nucleic acid sequence. Examples of complementary sequences include coding and non-coding sequences, wherein the non-coding sequence contains complementary nucleotides to the coding sequence and thus forms the complement of the coding sequence. A further example of complementary sequences are sense and antisense sequences, wherein the sense sequence contains complementary nucleotides to the antisense sequence and thus forms the complement of the antisense sequence. "Duplex" means at least two oligonucleotides and/or polynucleotides that are fully or partially complementary undergo Watson-Crick type base pairing among all or most of their nucleotides so that a stable complex is formed.

As described herein, the complementarity of sequences may be partial, in which only some of the nucleic acids match according to base pairing, or complete, where all the nucleic acids match according to base pairing. Thus, two sequences that are complementary to each other, may have a specified percentage of nucleotides that complement one another (e.g., about 60%, preferably 65%, 70%, 75%, 80%, 85%, 90%, 91%, 92%, 93%, 94%, 95%, 96%, 97%, 98%, 99%, or higher complementarity over a specified region). In embodiments, two sequences are complementary when they are completely complementary, having 100% complementarity. In embodiments, sequences in a pair of complementary sequences form portions of a single polynucleotide with non-base-pairing nucleotides (e.g., as in a hairpin structure, with or without an overhang) or portions of separate polynucleotides. In embodiments, one or both sequences in a pair of complementary sequences form portions of longer polynucleotides, which may or may not include additional regions of complementarity.

As used herein, the term "contacting" is used in accordance with its plain ordinary meaning and refers to the process of allowing at least two distinct species (e.g., chemical compounds, biomolecules, nucleotides, binding reagents, or cells) to become sufficiently proximal to react, interact or physically touch. However, the resulting reaction product can be produced directly from a reaction between the added reagents or from an intermediate from one or more of the added reagents that can be produced in the reaction mixture. The term "contacting" may include allowing two species to react, interact, or physically touch, wherein the two species may be a compound, a protein (e.g., an antibody), or enzyme.

As used herein, the term "hybridize" or "specifically hybridize" refers to a process where two complementary nucleic acid strands anneal to each other under appropriately stringent conditions. Hybridizations are typically and preferably conducted with oligonucleotides. The terms "annealing" and "hybridization" are used interchangeably to mean the formation of a stable duplex. Non-limiting examples of nucleic acid hybridization techniques are described in, for example, Sambrook, et al., Molecular Cloning: A Laboratory Manual (2nd Edition, 1989). Those skilled in the art understand how to estimate and adjust the stringency of hybridization conditions such that sequences having at least a desired level of complementarity will stably hybridize, while those having lower complementarity will not. As used herein, the term "stringent condition" refers to condition(s) under which a polynucleotide probe or primer will hybridize preferentially to its target sequence, and to a lesser extent to, or not at all to, other sequences. A "stringent hybridization" and "stringent hybridization wash conditions" in the context of nucleic acid hybridization are sequence dependent, and are different under different environmental parameters.

As used herein, the term "nucleic acid" refers to nucleotides (e.g., deoxyribonucleotides or ribonucleotides) and polymers thereof in either single-, double- or multiple-stranded form, or complements thereof. The terms "polynucleotide," "oligonucleotide," "oligo" or the like refer, in the usual and customary sense, to a sequence of nucleotides. The term "nucleotide" refers, in the usual and customary sense, to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA, and hybrid molecules having mixtures of single and double stranded DNA and RNA with linear or circular framework. Non-limiting examples of polynucleotides include a gene, a gene fragment, an exon, an intron, intergenic DNA (including, without limitation, heterochromatic DNA), messenger RNA (mRNA), transfer RNA, ribosomal RNA, a ribozyme, cDNA, a recombinant polynucleotide, a branched polynucleotide, a plasmid, a vector, isolated DNA of a sequence, isolated RNA of a sequence, a nucleic acid probe, and a primer. Polynucleotides useful in the methods of the disclosure may comprise natural nucleic acid sequences and variants thereof, artificial nucleic acid sequences, or a combination of such sequences. Nucleic acids can be linear or branched. For example, nucleic acids can be a linear chain of nucleotides or the nucleic acids can be branched, e.g., such that the nucleic acids comprise one or more arms or branches of nucleotides. Optionally, the branched nucleic acids are repetitively branched to form higher ordered structures such as dendrimers and the like.

As used herein, the terms "polynucleotide primer" and "primer" refer to any polynucleotide molecule that may hybridize to a polynucleotide template, be bound by a polymerase, and be extended in a template-directed process for nucleic acid synthesis. The primer may be a separate polynucleotide from the polynucleotide template, or both may be portions of the same polynucleotide (e.g., as in a hairpin structure having a 3' end that is extended along another portion of the polynucleotide to extend a double-stranded portion of the hairpin. A primer can be of any length depending on the particular technique it will be used for. For example, amplification primers are generally between 10 and 40 nucleotides in length. The length and complexity of the primer onto the nucleic acid template may vary. One of skill can adjust these factors to provide optimum hybridization and signal production for a given hybridization procedure. The primer permits the addition of a nucleotide residue thereto, or oligonucleotide or polynucleotide synthesis therefrom, under suitable conditions. In an embodiment the primer is a DNA primer, i.e., a primer consisting of, or largely consisting of, deoxyribonucleotide residues. The primers are designed to have a sequence that is the complement of a region of template polynucleotide (e.g., a padlock probe) to which the primer hybridizes. The addition of a nucleotide residue to the 3' end of a primer by formation of a phosphodiester bond results in an extension product The addition of a nucleotide residue to the 3' end of the extension product by formation of a phosphodiester bond results in a further extension product. In another embodiment the primer is an RNA primer. In embodiments, a primer is hybridized to a target polynucleotide. A "primer" is complementary to a polynucleotide template, and complexes by hydrogen bonding or hybridization with the template to give a primer/template complex for initiation of synthesis by a polymerase, which is extended by the addition of covalently bonded bases linked at its 3' end complementary to the template in the process of DNA synthesis. A primer typically has a length of 10 to 50 nucleotides. For example, a primer may have a length of 10 to 40, 10 to 30, 10 to 20, 25 to 50, 15 to 40, 15 to 30, 20 to 50, 20 to 40, or 20 to 30 nucleotides. In some embodiments, a primer has a length of 18 to 24 nucleotides. Examples of primers include, but are not limited to, P5 primer, P7 primer, PE1 primer, PE2 primer, A19 primer, or others known in the art.

Nucleic acids, including e.g., nucleic acids with a phosphorothioate backbone, can include one or more reactive moieties. As used herein, the term reactive moiety includes any group capable of reacting with another molecule, e.g., a nucleic acid or polypeptide through covalent, non-covalent or other interactions. By way of example, the nucleic acid can include an amino acid reactive moiety that reacts with an amino acid on a protein or polypeptide through a covalent, non-covalent or other interaction.

The term "messenger RNA" or "mRNA" refers to an RNA that is without introns and is capable of being translated into a polypeptide. The term "RNA" refers to any ribonucleic acid, including but not limited to mRNA, tRNA (transfer RNA), rRNA (ribosomal RNA), and/or noncoding RNA (such as lncRNA (long noncoding RNA)). The term "cDNA" refers to a DNA that is complementary or identical to an RNA, in either single stranded or double stranded form.

As used herein, the term "template polynucleotide" refers to any polynucleotide molecule that may be bound by a polymerase and utilized as a template for nucleic acid synthesis. A template polynucleotide may be a target polynucleotide. In general, the term "target polynucleotide" refers to a nucleic acid molecule or polynucleotide in a starting population of nucleic acid molecules having a target sequence whose presence, amount, and/or nucleotide sequence, or changes in one or more of these, are desired to be determined. In general, the term "target sequence" refers to a nucleic acid sequence on a single strand of nucleic acid. The target sequence may be a portion of a gene, a regulatory sequence, genomic DNA, cDNA, RNA including mRNA, microRNA (miRNA), rRNA, or others. The target sequence may be a target sequence from a sample or a secondary target such as a product of an amplification reaction. A target polynucleotide is not necessarily any single molecule or sequence. For example, a target polynucleotide may be any one of a plurality of target polynucleotides in a reaction, or all polynucleotides in a given reaction, depending on the reaction conditions. For example, in a nucleic acid amplification reaction with random primers, all polynucleotides in a reaction may be amplified. As a further example, a collection of targets may be simultaneously assayed using polynucleotide primers directed to a plurality of targets in a single reaction. As yet another example, all or a subset of polynucleotides in a sample may be modified by the addition of a primer-binding sequence (such as by the ligation of adapters containing the primer binding sequence), rendering each modified polynucleotide a target polynucleotide in a reaction with the corresponding primer polynucleotide(s).

A polynucleotide is typically composed of a specific sequence of four nucleotide bases: adenine (A); cytosine (C); guanine (G); and thymine (T) (uracil (U) for thymine (T) when the polynucleotide is RNA). Thus, the term "polynucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Polynucleotides may optionally include one or more non-standard nucleotide(s), nucleotide analog(s) and/or modified nucleotides.

As used herein, the terms "analog" or "analogue", in reference to a chemical compound (e.g., a nucleotide), refers to compound having a structure similar to that of another one, but differing from it in respect of one or more different atoms, functional groups, or substructures that are replaced with one or more other atoms, functional groups, or substructures. In the context of a nucleotide useful in practicing embodiments of the invention, a nucleotide analog refers to a compound that, like the nucleotide of which it is an analog, can be incorporated into a nucleic acid molecule (e.g., an extension product) by a suitable polymerase, for example, a DNA polymerase in the context of a dNTP analogue. The terms also encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, include, without limitation, phosphodiester derivatives including, e.g., phosphoramidate, phosphorodiamidate, phosphorothioate (also known as phosphothioate having double bonded sulfur replacing oxygen in the phosphate), phosphorodithioate, phosphonocarboxylic acids, phosphonocarboxylates, phosphonoacetic acid, phosphonoformic acid, methyl phosphonate, boron phosphonate, or O-methylphosphoroamidite linkages (see, e.g., see Eckstein, OLIGONUCLEOTIDES AND ANALOGUES: A PRACTICAL APPROACH, Oxford University Press) as well as modifications to the nucleotide bases such as in 5-methyl cytidine or pseudouridine; and peptide nucleic acid backbones and linkages. Other analog nucleic acids include those with positive backbones; non-ionic backbones, modified sugars, and non-ribose backbones (e.g. phosphorodiamidate morpholino oligos or locked nucleic acids (LNA) as known in the art), including those described in U.S. Pat. Nos. 5,235,033 and 5,034,506, and Chapters 6 and 7, ASC Symposium Series 580, CARBOHYDRATE MODIFICATIONS IN ANTISENSE RESEARCH, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. In embodiments, the internucleotide linkages in DNA are phosphodiester, phosphodiester derivatives, or a combination of both.

As used herein, the term "modified nucleotide" refers to nucleotide modified in some manner. Typically, a nucleotide contains a single 5-carbon sugar moiety, a single nitrogenous base moiety and 1 to three phosphate moieties. In embodiments, a nucleotide can include a blocking moiety (i.e., a reversible terminator) or a label moiety (e.g., a label is attached to the modified nucleotide through a cleavable linker). A blocking moiety on a nucleotide prevents formation of a covalent bond between the 3' hydroxyl moiety of the nucleotide and the 5' phosphate of another nucleotide. A blocking moiety on a nucleotide can be reversible, whereby the blocking moiety can be removed or modified to allow the 3' hydroxyl to form a covalent bond with the 5' phosphate of another nucleotide. A blocking moiety can be effectively irreversible under particular conditions used in a method set forth herein. In embodiments, the blocking moiety is attached to the 3' oxygen of the nucleotide and is independently —$NH_2$, —CN, —$CH_3$, $C_2$-$C_6$ allyl (e.g., —$CH_2$—$CH{=}CH_2$), methoxyalkyl (e.g., —$CH_2$—O—$CH_3$), or —$CH_2N_3$. In embodiments, the blocking moiety is attached to the 3' oxygen of the nucleotide and is independently

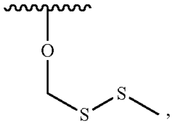,
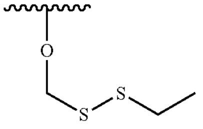,
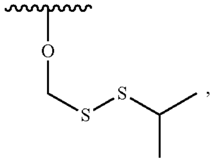,
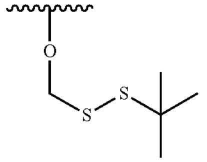,

-continued

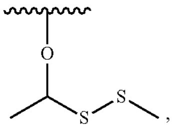,
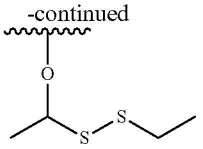,
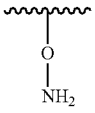,
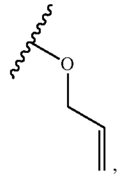,
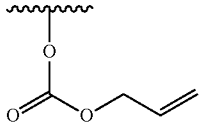,
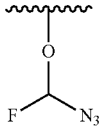,
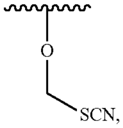,
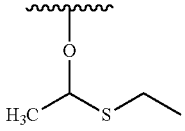,
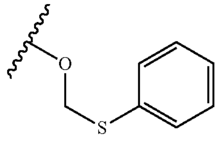,
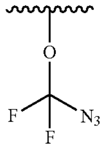,
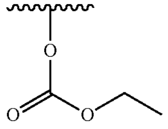,
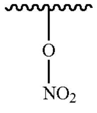,
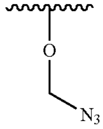, or
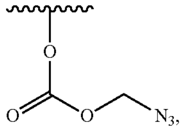, wherein the 3' oxygen of the nucleotide is explicitly shown in the formulae above. A label moiety of a nucleotide can be any moiety that allows the nucleotide to be detected, for example, using a spectroscopic method. Exemplary label moieties are fluorescent labels, mass labels, chemiluminescent labels, electrochemical labels, detectable labels and the like. One or more of the above moieties can be absent from a nucleotide used in the methods and compositions set forth herein. For example, a nucleotide can lack a label moiety or a blocking moiety or both. Examples of nucleotide analogues include, without limitation, 7-deaza-adenine, 7-deaza-guanine, the analogues of deoxynucleotides shown herein, analogues in which a label is attached through a cleavable linker to the 5-position of cytosine or thymine or to the 7-position of deaza-adenine or deaza-guanine, and analogues in which a small chemical moiety is used to cap the OH group at the 3'-position of deoxyribose. Nucleotide analogues and DNA polymerase-based DNA sequencing are also described in U.S. Pat. No. 6,664,079, which is incorporated herein by reference in its entirety for all purposes.

The term "cleavable linker" or "cleavable moiety" as used herein refers to a divalent or monovalent, respectively, moiety which is capable of being separated (e.g., detached, split, disconnected, hydrolyzed, a stable bond within the moiety is broken) into distinct entities. A cleavable linker is cleavable (e.g., specifically cleavable) in response to external stimuli (e.g., enzymes, nucleophilic/basic reagents, reducing agents, photo-irradiation, electrophilic/acidic reagents, organometallic and metal reagents, or oxidizing reagents). A chemically cleavable linker refers to a linker which is capable of being split in response to the presence of a chemical (e.g., acid, base, oxidizing agent, reducing agent, Pd(0), tris-(2-carboxyethyl)phosphine, dilute nitrous acid, fluoride, tris(3-hydroxypropyl)phosphine), sodium dithionite ($Na_2S_2O_4$), or hydrazine ($N_2H_4$)). A chemically cleavable linker is non-enzymatically cleavable. In embodiments, the cleavable linker is cleaved by contacting the cleavable linker with a cleaving agent. In embodiments, the cleaving agent is a phosphine containing reagent (e.g., TCEP or THPP), sodium dithionite ($Na_2S_2O_4$), weak acid, hydrazine ($N_2H_4$), Pd(0), or light-irradiation (e.g., ultraviolet radiation). In embodiments, cleaving includes removing. A "cleavable site" or "scissile linkage" in the context of a polynucleotide is a site which allows controlled cleavage of the polynucleotide strand (e.g., the linker, the primer, or the polynucleotide) by chemical, enzymatic, or photochemical means known in the art and described herein. A scissile site may refer to the linkage of a nucleotide between two other nucleotides in a nucleotide strand (i.e., an internucleosidic linkage). In embodiments, the scissile linkage can be located at any position within the one or more nucleic acid molecules, including at or near a terminal end (e.g., the 3' end of an oligonucleotide) or in an interior portion of the one or more nucleic acid molecules. In embodiments, conditions suitable for separating a scissile linkage include modulating the pH and/or the temperature. In embodiments, a scissile site can include at least one acid-labile linkage. For example, an acid-labile linkage may include a phosphoramidate linkage. In embodiments, a phosphoramidate linkage can be hydrolysable under acidic conditions, including mild acidic conditions such as trifluoroacetic acid and a suitable temperature (e.g., 30° C.), or other conditions known in the art, for example Matthias Mag, et al Tetrahedron Letters, Volume 33, Issue 48, 1992, 7319-7322. In embodiments, the scissile site can include at least one photolabile internucleosidic linkage (e.g., o-nitrobenzyl linkages, as described in Walker et al, J. Am. Chem. Soc. 1988, 110, 21, 7170-7177), such as o-nitrobenzyloxymethyl or p-nitrobenzyloxymethyl group(s). In embodiments, the scissile site includes at least one uracil nucleobase. In embodiments, a uracil nucleobase can be cleaved with a uracil DNA glycosylase (UDG) or Formamidopyrimidine DNA Glycosylase Fpg. In embodiments, the scissile linkage site includes a sequence-specific nicking site having a nucleotide sequence that is recognized and nicked by a nicking endonuclease enzyme or a uracil DNA glycosylase.

As used herein, the terms "reversible blocking groups" and "reversible terminators" are used in accordance with their plain and ordinary meanings and refer to a blocking moiety located, for example, at the 3' position of the nucleotide and may be a chemically cleavable moiety such as an allyl group, an azidomethyl group or a methoxymethyl group, or may be an enzymatically cleavable group such as a phosphate ester. Non-limiting examples of nucleotide blocking moieties are described in applications WO 2004/018497, U.S. Pat. Nos. 7,057,026, 7,541,444, WO 96/07669, U.S. Pat. Nos. 5,763,594, 5,808,045, 5,872,244 and 6,232,465 the contents of which are incorporated herein by reference in their entirety. The nucleotides may be labelled or unlabeled. They may be modified with reversible terminators useful in methods provided herein and may be 3'-O-blocked reversible or 3'-unblocked reversible terminators. In nucleotides with 3'-O-blocked reversible terminators, the blocking group —OR [reversible terminating (capping) group] is linked to the oxygen atom of the 3'-OH of the pentose, while the label is linked to the base, which acts as a reporter and can be cleaved. The 3'-O-blocked reversible terminators are known in the art, and may be, for instance, a 3'-$ONH_2$ reversible terminator, a 3'-O-allyl reversible terminator, or a 3'-O-azidomethyl reversible terminator. In embodiments, the reversible terminator moiety is attached to the 3'-oxygen of the nucleotide, having the formula:

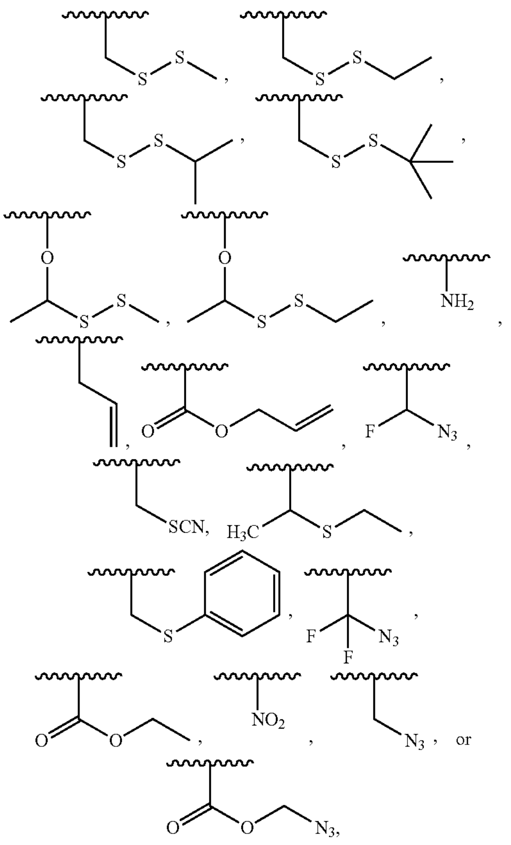

wherein the 3' oxygen of the nucleotide is not shown in the formulae above. The term "allyl" as described herein refers to an unsubstituted methylene attached to a vinyl group (i.e., —CH=$CH_2$). In embodiments, the reversible terminator moiety is

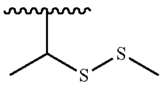 [SMILES: *C(C)SSC]

as described in U.S. Pat. No. 10,738,072, which is incorporated herein by reference for all purposes. For example, a nucleotide including a reversible terminator moiety may be represented by the formula:

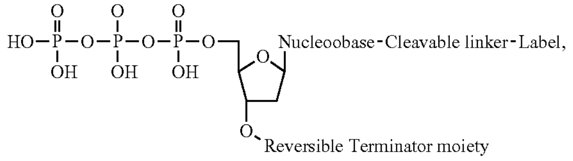

where the nucleobase is adenine or adenine analogue, thymine or thymine analogue, guanine or guanine analogue, or cytosine or cytosine analogue.

A label moiety of a nucleotide can be any moiety that allows the nucleotide to be detected, for example, using a spectroscopic method. Exemplary label moieties are fluorescent labels, mass labels, chemiluminescent labels, electrochemical labels, detectable labels and the like. One or more of the above moieties can be absent from a nucleotide used in the methods and compositions set forth herein. For example, a nucleotide can lack a label moiety or a blocking moiety or both. As used herein, the term "label" or "labels" generally refer to molecules that can directly or indirectly produce or result in a detectable signal either by themselves or upon interaction with another molecule. Non-limiting examples of detectable labels include labels comprising fluorescent dyes, biotin, digoxin, haptens, and epitopes. In general, a dye is a molecule, compound, or substance that can provide an optically detectable signal, such as a colorimetric, luminescent, bioluminescent, chemiluminescent, phosphorescent, or fluorescent signal. In embodiments, the dye is a fluorescent dye. Non-limiting examples of dyes, some of which are commercially available, include CF dyes (Biotium, Inc.), Alexa Fluor dyes (Thermo Fisher), DyLight dyes (Thermo Fisher), Cy dyes (GE Healthscience), IRDyes (Li-Cor Biosciences, Inc.), and HiLyte dyes (Anaspec, Inc.). In embodiments, the label is a fluorophore.

Examples of detectable agents (i.e., labels) include imaging agents, including fluorescent and luminescent substances, molecules, or compositions, including, but not limited to, a variety of organic or inorganic small molecules commonly referred to as "dyes," "labels," or "indicators." Examples include fluorescein, rhodamine, acridine dyes, Alexa dyes, and cyanine dyes. In embodiments, the detectable moiety is a fluorescent molecule (e.g., acridine dye, cyanine, dye, fluorine dye, oxazine dye, phenanthridine dye, or rhodamine dye). In embodiments, the detectable moiety is a fluorescent molecule (e.g., acridine dye, cyanine, dye, fluorine dye, oxazine dye, phenanthridine dye, or rhodamine dye). The term "cyanine" or "cyanine moiety" as described herein refers to a detectable moiety containing two nitrogen groups separated by a polymethine chain. In embodiments, the cyanine moiety has 3 methine structures (i.e. cyanine 3 or Cy3). In embodiments, the cyanine moiety has 5 methine structures (i.e. cyanine 5 or Cy5). In embodiments, the cyanine moiety has 7 methine structures (i.e., cyanine 7 or Cy7).

As used herein, the term "polymer" refers to macromolecules having one or more structurally unique repeating units. The repeating units are referred to as "monomers," which are polymerized for the polymer. Typically, a polymer is formed by monomers linked in a chain-like structure. A polymer formed entirely from a single type of monomer is referred to as a "homopolymer." A polymer formed from two or more unique repeating structural units may be referred to as a "copolymer." A polymer may be linear or branched, and may be random, block, polymer brush, hyperbranched polymer, bottlebrush polymer, dendritic polymer, or polymer micelles. The term "polymer" includes homopolymers, copolymers, tripolymers, tetra polymers and other polymeric molecules made from monomeric subunits. Copolymers include alternating copolymers, periodic copolymers, statistical copolymers, random copolymers, block copolymers, linear copolymers and branched copolymers. The term "polymerizable monomer" is used in accordance with its meaning in the art of polymer chemistry and refers to a compound that may covalently bind chemically to other monomer molecules (such as other polymerizable monomers that are the same or different) to form a polymer.

Polymers can be hydrophilic, hydrophobic or amphiphilic, as known in the art. Thus, "hydrophilic polymers" are substantially miscible with water and include, but are not limited to, polyethylene glycol and the like. "Hydrophobic polymers" are substantially immiscible with water and include, but are not limited to, polyethylene, polypropylene, polybutadiene, polystyrene, polymers disclosed herein, and the like. "Amphiphilic polymers" have both hydrophilic and hydrophobic properties and are typically copolymers having hydrophilic segment(s) and hydrophobic segment(s). Polymers include homopolymers, random copolymers, and block copolymers, as known in the art. The term "homopolymer" refers, in the usual and customary sense, to a polymer having a single monomeric unit. The term "copolymer" refers to a polymer derived from two or more monomeric species. The term "random copolymer" refers to a polymer derived from two or more monomeric species with no preferred ordering of the monomeric species. The term "block copolymer" refers to polymers having two or homopolymer subunits linked by covalent bond. Thus, the term "hydrophobic homopolymer" refers to a homopolymer which is hydrophobic. The term "hydrophobic block copolymer" refers to two or more homopolymer subunits linked by covalent bonds and which is hydrophobic.

As used herein, the term "hydrogel" refers to a three-dimensional polymeric structure that is substantially insoluble in water, but which is capable of absorbing and retaining large quantities of water to form a substantially stable, often soft and pliable, structure. In embodiments, water can penetrate in between polymer chains of a polymer network, subsequently causing swelling and the formation of a hydrogel. In embodiments, hydrogels are super-absorbent (e.g., containing more than about 90% water) and can be comprised of natural or synthetic polymers.

As used herein, the terms "solid support" and "substrate" and "substrate surface" and "solid surface" refers to discrete solid or semi-solid surfaces to which a plurality of functional groups may be attached. A solid support may encompass any type of solid, porous, or hollow sphere, ball, cylinder, or other similar configuration composed of plastic, ceramic, metal, or polymeric material (e.g., hydrogel) onto which a nucleic acid may be immobilized (e.g., covalently or non-covalently). A solid support may comprise a discrete particle that may be spherical (e.g., microspheres) or have a non-spherical or irregular shape, such as cubic, cuboid, pyramidal, cylindrical, conical, oblong, or disc-shaped, and the like. A bead can be non-spherical in shape. A solid support may be used interchangeably with the term "bead." A solid support may further comprise a polymer or hydrogel on the surface to which the primers are attached. Exemplary solid supports include, but are not limited to, glass and modified or functionalized glass, plastics (including acrylics, polystyrene and copolymers of styrene and other materials, polypropylene, polyethylene, polybutylene, polyurethanes, Teflon™, cyclic olefin copolymers, polyimides etc.), nylon, ceramics, resins, Zeonor, silica or silica-based materials including silicon and modified silicon, carbon, metals, inorganic glasses, optical fiber bundles, photopatternable dry film resists, UV-cured adhesives and polymers. The solid support, or regions thereof, can be substantially flat. The solid support can have surface features such as wells, pits, channels, ridges, raised regions, pegs, posts or the like. The term solid support is encompassing of a substrate having a surface comprising a plurality of functional groups covalently attached thereto, wherein the functional groups are selected to immobilize the sample.

As used herein, the term "selective" or "selectivity" or the like of a compound refers to the substance's ability to discriminate between molecular targets. As used herein, the terms "specific", "specifically", "specificity", or the like of a compound refers to the substance's ability to cause a particular action, such as binding, to a particular molecular target with minimal or no action to other substances (e.g., an antibody and antigen).

As used herein, the term "barcode" refers to a known nucleic acid sequence that allows some feature with which the barcode is associated to be identified. Typically, a barcode is unique to a particular feature in a pool of barcodes that differ from one another in sequence, and each of which is associated with a different feature. In embodiments, barcodes are about or at least about 5, 6, 7, 8, 9, 10, 15, 20, 25, 30, 40, 50, 75 or more nucleotides in length. In embodiments, barcodes are shorter than 20, 15, 10, 9, 8, 7, 6, or 5 nucleotides in length. In embodiments, barcodes are 10-50 nucleotides in length, such as 15-40 or 20-30 nucleotides in length. In a pool of different barcodes, barcodes may have the same or different lengths. In general, barcodes are of sufficient length and comprise sequences that are sufficiently different to allow the identification of associated features (e.g., a binding moiety or analyte) based on barcodes with which they are associated. In embodiments, a barcode can be identified accurately after the mutation, insertion, or deletion of one or more nucleotides in the barcode sequence, such as the mutation, insertion, or deletion of 1, 2, 3, 4, 5, or more nucleotides. In embodiments, each barcode in a plurality of barcodes differs from every other barcode in the plurality by at least three nucleotide positions, such as at least 3, 4, 5, 6, 7, 8, 9, 10, or more nucleotide positions. In embodiments, the barcodes are selected to form a known set of barcodes, e.g., the set of barcodes may be distinguished by a particular Hamming distance.

The terms "bind" and "bound" as used herein are used in accordance with their plain and ordinary meanings and refer to an association between atoms or molecules. The association can be direct or indirect. For example, bound atoms or molecules may be directly bound to one another, e.g., by a covalent bond or non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions and the like). As a further example, two molecules may be bound indirectly to one another by way of direct binding to one or more intermediate molecules (e.g., as in a substrate, bound to a first antibody, bound to an analyte, bound to a second antibody), thereby forming a complex. As used herein, the term "attached" refers to the state of two things being joined, fastened, adhered, connected or bound to each other. For example, a sample such as a nucleic acid, cell, or tissue, can be attached to a material, such as a hydrogel, polymer, or solid support, by a covalent or non-covalent bond. In embodiments, attachment is a covalent attachment.

"Specific binding" is where the binding is selective between two molecules. A particular example of specific binding is that which occurs between an antibody and an antigen. Typically, specific binding can be distinguished from non-specific when the dissociation constant (KD) is less than about $1\times10^{-5}$ M or less than about $1\times10^{-6}$ M or $1\times10^{-7}$ M. Specific binding can be detected, for example, by ELISA, immunoprecipitation, coprecipitation, with or without chemical crosslinking, two-hybrid assays and the like.

Where a range of values is provided, it is understood that each intervening value, to the tenth of the unit of the lower limit unless the context clearly indicates otherwise, between the upper and lower limit of that range, and any other stated or unstated intervening value in, or smaller range of values within, that stated range is encompassed by such disclosure herein. The upper and lower limits of any such smaller range (within a more broadly recited range) may independently be included in the smaller ranges, or as particular values themselves, and are also encompassed by such disclosure herein, subject to any specifically excluded limit in the stated range. Where the stated range includes one or both of the limits, ranges excluding either or both of those included limits are also included by such disclosure herein.

As used herein, a "native" nucleotide is used in accordance with its plain and ordinary meaning and refers to a naturally occurring nucleotide that does not include an exogenous label (e.g., a fluorescent dye, or other label) or chemical modification such as may characterize a nucleotide analog. Examples of native nucleotides useful for carrying out procedures described herein include: dATP (2'-deoxyadenosine-5'-triphosphate); dGTP (2'-deoxyguanosine-5'-triphosphate); dCTP (2'-deoxycytidine-5'-triphosphate); dTTP (2'-deoxythymidine-5'-triphosphate); and dUTP (2'-deoxyuridine-5'-triphosphate).

Provided herein are methods, systems, and compositions for analyzing a sample (e.g., sequencing nucleic acids within a sample) in situ. The term "in situ" is used in accordance with its ordinary meaning in the art and refers to a sample surrounded by at least a portion of its native environment, such as it may preserve the relative position of two or more elements. For example, an extracted human cell obtained is considered in situ when the cell is retained in its local microenvironment so as to avoid extracting the target (e.g., nucleic acid molecules or proteins) away from their native environment. An in situ sample (e.g., a cell) can be obtained from a suitable subject. An in situ cell sample may refer to a cell and its surrounding milieu, or a tissue. A sample can be isolated or obtained directly from a subject or part thereof. In embodiments, the methods described herein (e.g., sequencing a plurality of target nucleic acids of a cell in situ) are applied to an isolated cell (i.e., a cell not surrounded by least a portion of its native environment). For the avoidance of any doubt, when the method is performed within a cell (e.g., an isolated cell) the method may be considered in situ. In some embodiments, a sample is obtained indirectly from an individual or medical professional. A sample can be any specimen that is isolated or obtained from a subject or part thereof. A sample can be any specimen that is isolated or obtained from multiple subjects. Non-limiting examples of specimens include fluid or tissue from a subject, including, without limitation, blood or a blood product (e.g., serum, plasma, platelets, buffy coats, or the like), umbilical cord blood, chorionic villi, amniotic fluid, cerebrospinal fluid, spinal fluid, lavage fluid (e.g., lung, gastric, peritoneal, ductal, ear, arthroscopic), a biopsy sample, celocentesis sample, cells (blood cells, lymphocytes, placental cells, stem cells, bone marrow derived cells, embryo or fetal cells) or parts thereof (e.g., mitochondrial, nucleus, extracts, or the like), urine, feces, sputum, saliva, nasal mucous, prostate fluid, lavage, semen, lymphatic fluid, bile, tears, sweat, breast milk, breast fluid, the like or combinations thereof. Non-limiting examples of tissues include organ tissues (e.g., liver, kidney, lung, thymus, adrenals, skin, bladder, reproductive organs, intestine, colon, spleen, brain, the like or parts thereof), epithelial tissue, hair, hair follicles, ducts, canals, bone, eye, nose, mouth, throat, ear, nails, the like, parts thereof or combinations thereof. A sample may comprise cells or tissues that are normal, healthy, diseased (e.g., infected), and/or cancerous (e.g., cancer cells). A sample obtained from a subject may comprise cells or cellular material (e.g., nucleic acids) of multiple organisms (e.g., virus nucleic acid, fetal nucleic acid, bacterial nucleic acid, parasite nucleic acid). A sample may include a cell and RNA transcripts. A sample can comprise nucleic acids obtained from one or more subjects. In some embodiments a sample comprises nucleic acid obtained from a single subject. A subject can be any living or non-living organism, including but not limited to a human, non-human animal, plant, bacterium, fungus, virus, or protist. A subject may be any age (e.g., an embryo, a fetus, infant, child, adult). A subject can be of any sex (e.g., male, female, or combination thereof). A subject may be pregnant. In some embodiments, a subject is a mammal. In some embodiments, a subject is a plant. In some embodiments, a subject is a human subject. A subject can be a patient (e.g., a human patient). In some embodiments a subject is suspected of having a genetic variation or a disease or condition associated with a genetic variation.

As used herein, the term "disease state" is used in accordance with its plain and ordinary meaning and refers to any abnormal biological or aberrant state of a cell. The presence of a disease state may be identified by the same collection of biological constituents used to determine the cell's biological state. In general, a disease state will be detrimental to a biological system. A disease state may be a consequence of, inter alia, an environmental pathogen, for example a viral infection (e.g., HIV/AIDS, hepatitis B, hepatitis C, influenza, measles, etc.), a bacterial infection, a parasitic infection, a fungal infection, or infection by some other organism. A disease state may also be the consequence of some other environmental agent, such as a chemical toxin or a chemical carcinogen. As used herein, a disease state further includes genetic disorders wherein one or more copies of a gene is altered or disrupted, thereby affecting its biological function. Exemplary genetic diseases include, but are not limited to, polycystic kidney disease, familial multiple endocrine neoplasia type I, neurofibromatosis, Tay-Sachs disease, Huntington's disease, sickle cell anemia, thalassemia, and Down's syndrome, as well as others (see, e.g., The Metabolic and Molecular Bases of Inherited Diseases, 7th ed., McGraw-Hill Inc., New York). Other exemplary diseases include, but are not limited to, cancer, hypertension, Alzheimer's disease, neurodegenerative diseases, and neuropsychiatric disorders such as bipolar affective disorders or paranoid schizophrenic disorders. Disease states are monitored to determine the level or severity (e.g., the stage or progression) of one or more disease states of a subject and, more specifically, detect changes in the biological state of a subject which are correlated to one or more disease states (see, e.g., U.S. Pat. No. 6,218,122, which is incorporated by reference herein in its entirety). In embodiments, methods provided herein are also applicable to monitoring the disease state or states of a subject undergoing one or more therapies. Thus, the present disclosure also provides, in some embodiments, methods for determining or monitoring efficacy of a therapy or therapies (i.e., determining a level of therapeutic effect) upon a subject. In embodiments, methods of the present disclosure can be used to assess therapeutic efficacy in a clinical trial, e.g., as an early surrogate marker for success or failure in such a clinical trial. Within eukaryotic cells, there are hundreds to thousands of signaling pathways that are interconnected. For this reason, perturbations in the function of proteins within a cell have numerous effects on other proteins and the transcription of other genes that are connected by primary, secondary, and sometimes tertiary pathways. This extensive interconnection between the function of various proteins means that the alteration of any one protein is likely to result in compensatory changes in a wide number of other proteins. In particular, the partial disruption of even a single protein within a cell, such as by exposure to a drug or by a disease state which modulates the gene copy number (e.g., a genetic mutation), results in characteristic compensatory changes in the transcription of enough other genes that these changes in transcripts can be used to define a "signature" of particular transcript alterations which are related to the disruption of function, e.g., a particular disease state or therapy, even at a stage where changes in protein activity are undetectable.

The terms "polypeptide," "peptide" and "protein" are used interchangeably herein to refer to a polymer of amino acid residues, wherein the polymer may optionally be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymer. A protein may refer to a protein expressed in a cell.

A polypeptide, or a cell is "recombinant" when it is artificial or engineered, or derived from or contains an artificial or engineered protein or nucleic acid (e.g., non-natural or not wild type). For example, a polynucleotide that is inserted into a vector or any other heterologous location, e.g., in a genome of a recombinant organism, such that it is not associated with nucleotide sequences that normally flank the polynucleotide as it is found in nature is a recombinant polynucleotide. A protein expressed in vitro or in vivo from a recombinant polynucleotide is an example of a recombinant polypeptide. Likewise, a polynucleotide sequence that does not appear in nature, for example a variant of a naturally occurring gene, is recombinant.

As used herein, a "single cell" refers to one cell. Single cells useful in the methods described herein can be obtained from a tissue of interest, or from a biopsy, blood sample, or cell culture. Additionally, cells from specific organs, tissues, tumors, neoplasms, or the like can be obtained and used in the methods described herein. In general, cells from any population can be used in the methods, such as a population of prokaryotic or eukaryotic organisms, including bacteria or yeast.

The term "cellular component" is used in accordance with its ordinary meaning in the art and refers to any organelle, nucleic acid, protein, or analyte that is found in a prokaryotic, eukaryotic, archaeal, or other organismic cell type. Examples of cellular components (e.g., a component of a cell) include RNA transcripts, proteins, membranes, lipids, and other analytes.

A "gene" refers to a polynucleotide sequence that is capable of conferring biological function after being transcribed and/or translated.

As used herein, the term "DNA polymerase" and "nucleic acid polymerase" are used in accordance with their plain ordinary meanings and refer to enzymes capable of synthesizing nucleic acid molecules from nucleotides (e.g., deoxyribonucleotides). Exemplary types of polymerases that may be used in the compositions and methods of the present disclosure include the nucleic acid polymerases such as DNA polymerase, DNA- or RNA-dependent RNA polymerase, and reverse transcriptase. In some cases, the DNA polymerase is 9° N polymerase or a variant thereof, *E. Coli* DNA polymerase I, Bacteriophage T4 DNA polymerase, Sequenase, Taq DNA polymerase, DNA polymerase from *Bacillus stearothermophilus*, Bst 2.0 DNA polymerase, 9° N polymerase (exo-)A485L/Y409V, Phi29 DNA Polymerase (φ29 DNA Polymerase), T7 DNA polymerase, DNA polymerase II, DNA polymerase III holoenzyme, DNA polymerase IV, DNA polymerase V, Vent® DNA polymerase, Therminator™ II DNA Polymerase, Therminator™ III DNA Polymerase, or Therminator™ IX DNA Polymerase. In embodiments, the polymerase is a protein polymerase. Typically, a DNA polymerase adds nucleotides to the 3'-end of a DNA strand, one nucleotide at a time. In embodiments, the DNA polymerase is a Pol I DNA polymerase, Pol II DNA polymerase, Pol III DNA polymerase, Pol IV DNA polymerase, Pol V DNA polymerase, Pol β DNA polymerase, Pol μ DNA polymerase, Pol λ DNA polymerase, Pol σ DNA polymerase, Pol α DNA polymerase, Pol δ DNA polymerase, Pol ε DNA polymerase, Pol η DNA polymerase, Pol τ DNA polymerase, Pol κ DNA polymerase, Pol ζ DNA polymerase, Pol γ DNA polymerase, Pol θ DNA polymerase, Pol ν DNA polymerase, or a thermophilic nucleic acid polymerase (e.g. Therminator γ, 9° N polymerase (exo-), Therminator II, Therminator III, or Therminator IX). In embodiments, the DNA polymerase is a modified archaeal DNA polymerase. In embodiments, the polymerase is a reverse transcriptase. In embodiments, the polymerase is a mutant *P. abyssi* polymerase (e.g., such as a mutant *P. abyssi* polymerase described in WO 2018/148723 or WO 2020/056044, each of which are incorporated herein by reference for all purposes).

As used herein, the term "thermophilic nucleic acid polymerase" refers to a family of DNA polymerases (e.g., 9° N™) and mutants thereof derived from the DNA polymerase originally isolated from the hyperthermophilic archaea, *Thermococcus* sp. 9 degrees N-7, found in hydrothermal vents at that latitude (East Pacific Rise) (Southworth M W, et al. PNAS. 1996; 93(11):5281-5285). A thermophilic nucleic acid polymerase is a member of the family B DNA polymerases. Site-directed mutagenesis of the 3'-5' exo motif I (Asp-Ile-Glu or DIE) to AIA, AIE, EIE, EID or DIA yielded polymerase with no detectable 3' exonuclease activity. Mutation to Asp-Ile-Asp (DID) resulted in reduction of 3'-5' exonuclease specific activity to <1% of wild type, while maintaining other properties of the polymerase including its high strand displacement activity. The sequence AIA (D141A, E143A) was chosen for reducing exonuclease. Subsequent mutagenesis of key amino acids results in an increased ability of the enzyme to incorporate dideoxynucleotides, ribonucleotides and acyclonucleotides (e.g., Therminator II enzyme from New England Biolabs with D141A/E143A/Y409V/A485L mutations); 3'-amino-dNTPs, 3'-azido-dNTPs and other 3'-modified nucleotides (e.g., NEB Therminator III DNA Polymerase with D141A/E143A/L408S/Y409A/P410V mutations, NEB Therminator IX DNA polymerase), or γ-phosphate labeled nucleotides (e.g., Therminator γ: D141A/E143A/W355A/L408W/R460A/Q461S/K464E/D480V/R484W/A485L). Typically, these enzymes do not have 5'-3' exonuclease activity. Additional information about thermophilic nucleic acid polymerases may be found in (Southworth M W, et al. PNAS. 1996; 93(11):5281-5285; Bergen K, et al. *ChemBioChem.* 2013; 14(9):1058-1062; Kumar S, et al. *Scientific Reports.* 2012; 2:684; Fuller C W, et al. 2016; 113(19):5233-5238; Guo J, et al. *Proceedings of the National Academy of Sciences of the United States of America.* 2008; 105(27):9145-9150), which are incorporated herein in their entirety for all purposes.

As used herein, the term "exonuclease activity" is used in accordance with its ordinary meaning in the art, and refers to the removal of a nucleotide from a nucleic acid by a DNA polymerase. For example, during polymerization, nucleotides are added to the 3' end of the primer strand. Occasionally a DNA polymerase incorporates an incorrect nucleotide to the 3'-OH terminus of the primer strand, wherein the incorrect nucleotide cannot form a hydrogen bond to the corresponding base in the template strand. Such a nucleotide, added in error, is removed from the primer as a result of the 3' to 5' exonuclease activity of the DNA polymerase. In embodiments, exonuclease activity may be referred to as "proofreading." When referring to 3'-5' exonuclease activity, it is understood that the DNA polymerase facilitates a hydrolyzing reaction that breaks phosphodiester bonds at either the 3' end of a polynucleotide chain to excise the nucleotide. In embodiments, 3'-5' exonuclease activity refers to the successive removal of nucleotides in single-stranded DNA in a 3'→5' direction, releasing deoxyribonucleoside 5'-monophosphates one after another. Methods for quantifying exonuclease activity are known in the art, see for example Southworth et al, PNAS Vol 93, 8281-8285 (1996).

As used herein, the term "extension" or "elongation" is used in accordance with its plain and ordinary meanings and refer to synthesis by a polymerase of a new polynucleotide strand complementary to a template strand by adding free nucleotides (e.g., dNTPs) from a reaction mixture that are complementary to the template in the 5'-to-3' direction. Extension includes condensing the 5'-phosphate group of the dNTPs with the 3'-hydroxy group at the end of the nascent (elongating) polynucleotide strand.

As used herein, the term "kit" refers to any delivery system for delivering materials. In the context of reaction assays, such delivery systems include systems that allow for the storage, transport, or delivery of reaction reagents (e.g., oligonucleotides, enzymes, etc. in the appropriate containers) and/or supporting materials (e.g., buffers, written instructions for performing the assay, etc.) from one location to another. For example, kits include one or more enclosures (e.g., boxes) containing the relevant reaction reagents and/or supporting materials. As used herein, the term "fragmented kit" refers to a delivery system comprising two or more separate containers that each contain a subportion of the total kit components. The containers may be delivered to the intended recipient together or separately. For example, a first container may contain an enzyme for use in an assay, while a second container contains oligonucleotides. In contrast, a "combined kit" refers to a delivery system containing all of the components of a reaction assay in a single container (e.g., in a single box housing each of the desired components). The term "kit" includes both fragmented and combined kits.

As used herein the term "determine" can be used to refer to the act of ascertaining, establishing or estimating. A determination can be probabilistic. For example, a determination can have an apparent likelihood of at least 50%, 75%, 90%, 95%, 98%, 99%, 99.9% or higher. In some cases, a determination can have an apparent likelihood of 100%. An exemplary determination is a maximum likelihood analysis or report. As used herein, the term "identify," when used in reference to a thing, can be used to refer to recognition of the thing, distinction of the thing from at least one other thing or categorization of the thing with at least one other thing. The recognition, distinction or categorization can be probabilistic. For example, a thing can be identified with an apparent likelihood of at least 50%, 75%, 90%, 95%, 98%, 99%, 99.9% or higher. A thing can be identified based on a result of a maximum likelihood analysis. In some cases, a thing can be identified with an apparent likelihood of 100%.

As used herein, the terms "sequencing", "sequence determination", and "determining a nucleotide sequence", are used in accordance with their ordinary meaning in the art, and refer to determination of partial as well as full sequence information of the nucleic acid being sequenced, and particular physical processes for generating such sequence information. That is, the term includes sequence comparisons, fingerprinting, and like levels of information about a target nucleic acid, as well as the express identification and ordering of nucleotides in a target nucleic acid. The term also includes the determination of the identification, ordering, and locations of one, two, or three of the four types of nucleotides within a target nucleic acid. Sequencing produces a sequencing read.

As used herein, the term "sequencing cycle" is used in accordance with its plain and ordinary meaning and refers to incorporating one or more nucleotides (e.g., a compound described herein) to the 3' end of a polynucleotide with a polymerase, and detecting one or more labels that identify the one or more nucleotides incorporated. The sequencing may be accomplished by, for example, sequencing by synthesis, pyrosequencing, and the like. In embodiments, a sequencing cycle includes extending a complementary polynucleotide by incorporating a first nucleotide using a polymerase, wherein the polynucleotide is hybridized to a template nucleic acid, detecting the first nucleotide, and identifying the first nucleotide. In embodiments, to begin a sequencing cycle, one or more differently labeled nucleotides and a DNA polymerase can be introduced. Following nucleotide addition, signals produced (e.g., via excitation and emission of a detectable label) can be detected to determine the identity of the incorporated nucleotide (based on the labels on the nucleotides). Reagents can then be added to remove the 3' reversible terminator and to remove labels from each incorporated base. Reagents, enzymes and other substances can be removed between steps by washing. Cycles may include repeating these steps, and the sequence of each cluster is read over the multiple repetitions.

As used herein, the term "sequencing read" is used in accordance with its plain and ordinary meaning and refers to an inferred sequence of nucleotide base pairs (or nucleotide base pair probabilities) corresponding to all or part of a single polynucleotide fragment. A sequencing read may include 10, 20, 30, 40, 50, 60, 70, 80, 90, 100, 150, 200, 250, or more nucleotide base pairs. In embodiments, a sequencing read includes reading a barcode and a template nucleotide sequence. In embodiments, a sequencing read includes reading a template nucleotide sequence. In embodiments, a sequencing read includes reading a barcode and not a template nucleotide sequence. As used herein, the term "sequencing read" refers to an inferred sequence of base pairs (or base pair probabilities) corresponding to all or part of a single DNA fragment. In embodiments, the sequenced read of a barcode is considered a code. In embodiments, the sequenced read generates a codeword.

As used herein, the term "code," means a system of rules to convert information, such as signals obtained from a detection apparatus, into another form or representation, such as a base call or nucleic acid sequence. For example, signals that are produced by one or more incorporated nucleotides can be encoded by a digit. The digit can have several potential values, each value encoding a different signal state. For example, a binary digit will have a first value for a first signal state and a second value for a second signal state. A digit can have a higher radix including, for example, a ternary digit having three potential values, a quaternary digit having four potential values, etc. A series of digits can form a codeword. The length of the codeword is the same as the number of sequencing steps performed. Exemplary codes include, but are not limited to, a Hamming code. A Hamming code is used in accordance with its ordinary meaning in computer science, mathematics, telecommunication sciences and refers to a code that can be used to detect and correct the errors that can occur when the data is moved or stored. The Hamming distance refers to the difference in integer number between two codewords of equal length, and may be determined using known techniques in the art such as the Hamming distance test or the Hamming distance algorithm. For example, for two codewords (i.e., two sequenced barcodes that have been converted to a string of integers), a difference of 0 indicates that the codewords (i.e., the sequences) are identical. A difference of 1 in integer value indicates a Hamming distance of 1, thus 1 base difference between the oligos. Hamming distance is the number of positions for which the corresponding bit values in the two strings are different. In other words, the test measures the minimum number of substitutions that would be necessary to change one bit string into the other.

As used herein, the term "signal" refers to energy or coded information that can be selectively observed over other energy or information such as background energy or information. A signal can have a desired or predefined characteristic. For example, an optical signal can be characterized or observed by one or more of intensity, wavelength, energy, frequency, power, luminance or the like. Other signals can be quantified according to characteristics such as voltage, current, electric field strength, magnetic field strength, frequency, power, temperature, etc. An optical signal can be detected at a particular intensity, wavelength, or color; an electrical signal can be detected at a particular frequency, power or field strength; or other signals can be detected based on characteristics known in the art pertaining to spectroscopy and analytical detection. Absence of signal is understood to be a signal level of zero or a signal level that is not meaningfully distinguished from noise. In embodiments, a sequencing cycle generates a signal upon the correct nucleotide incorporation event.

As used herein, the term "signal state" refers to a mode or characteristic of a signal obtained from a detector. Exemplary modes or characteristics include, but are not limited to, wavelength of energy absorption, wavelength of luminescent excitation, wavelength of luminescence emission, intensity of energy absorption, intensity of luminescent excitation, intensity of luminescent emission, polarization state, luminescence lifetime, color. A signal state can have multiple potential values. For example, a signal state can have two potential states (binary), three potential states (ternary), four potential states (quaternary) etc. An example of a binary signal state is presence or absence of signal detected at a particular wavelength. Another example of a binary signal state is luminescence emission detected at a first wavelength or second wavelength.

As used herein a "genetically modifying agent" is a substance that alters the genetic sequence of a cell following exposure to the cell, resulting in an agent-mediated nucleic acid sequence. In embodiments, the genetically modifying agent is a small molecule, protein, pathogen (e.g., virus or bacterium) toxin, oligonucleotide, or antigen. In embodiments, the genetically modifying agent is a virus (e.g., influenza) and the agent-mediated nucleic acid sequence is the nucleic acid sequence that develops within a T-cell upon cellular exposure and contact with the virus. In embodiments, the genetically modifying agent modulates the expression of a nucleic acid sequence in a cell relative to a control (e.g., the absence of the genetically modifying agent).

The term "synthetic target" as used herein refers to a modified protein or nucleic acid such as those constructed by synthetic methods. In embodiments, a synthetic target is artificial or engineered, or derived from or contains an artificial or engineered protein or nucleic acid (e.g., non-natural or not wild type). For example, a polynucleotide that is inserted or removed such that it is not associated with nucleotide sequences that normally flank the polynucleotide as it is found in nature is a synthetic target polynucleotide.

The terms "bioconjugate group," "bioconjugate reactive moiety," and "bioconjugate reactive group" refer to a chemical moiety which participates in a reaction to form a bioconjugate linker (e.g., covalent linker). Non-limiting examples of bioconjugate groups include —$NH_2$, "*MERGEFORMAT*MERGEFORMAT —COOH, —$COOCH_3$, —N— hydroxysuccinimide, -maleimide,

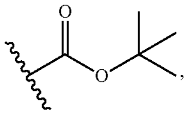, or 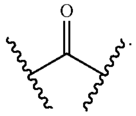.

In embodiments, the bioconjugate reactive group may be protected (e.g., with a protecting group). In embodiments, the bioconjugate reactive moiety is

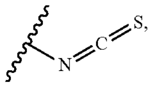 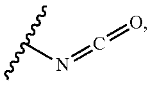 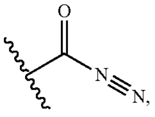 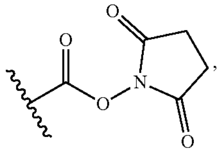 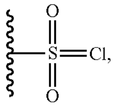 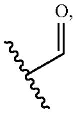 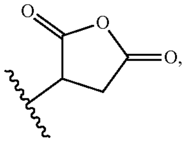 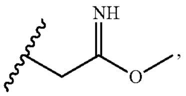 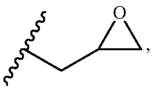 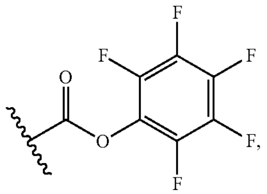

or —$NH_2$. Additional examples of bioconjugate reactive groups and the resulting bioconjugate reactive linkers may be found in the Bioconjugate Table below:

| Bioconjugate reactive group 1 (e.g., electrophilic bioconjugate reactive moiety) | Bioconjugate reactive group 2 (e.g., nucleophilic bioconjugate reactive moiety) | Resulting Bioconjugate reactive linker |
|---|---|---|
| activated esters | amines/anilines | carboxamides |
| acrylamides | thiols | thioethers |

-continued

| Bioconjugate reactive group 1 (e.g., electrophilic bioconjugate reactive moiety) | Bioconjugate reactive group 2 (e.g., nucleophilic bioconjugate reactive moiety) | Resulting Bioconjugate reactive linker |
|---|---|---|
| acyl azides | amines/anilines | carboxamides |
| acyl halides | amines/anilines | carboxamides |
| acyl halides | alcohols/phenols | esters |
| acyl nitriles | alcohols/phenols | esters |
| acyl nitriles | amines/anilines | carboxamides |
| aldehydes | amines/anilines | imines |
| aldehydes or ketones | hydrazines | hydrazones |
| aldehydes or ketones | hydroxylamines | oximes |
| alkyl halides | amines/anilines | alkyl amines |
| alkyl halides | carboxylic acids | esters |
| alkyl halides | thiols | thioethers |
| alkyl halides | alcohols/phenols | ethers |
| alkyl sulfonates | thiols | thioethers |
| alkyl sulfonates | carboxylic acids | esters |
| alkyl sulfonates | alcohols/phenols | ethers |
| anhydrides | alcohols/phenols | esters |
| anhydrides | amines/anilines | carboxamides |
| aryl halides | thiols | thiophenols |
| aryl halides | amines | aryl amines |
| aziridines | thiols | thioethers |
| boronates | glycols | boronate esters |
| carbodiimides | carboxylic acids | N-acylureas or anhydrides |
| diazoalkanes | carboxylic acids | esters |
| epoxides | thiols | thioethers |
| haloacetamides | thiols | thioethers |
| haloplatinate | amino | platinum complex |
| haloplatinate | heterocycle | platinum complex |
| haloplatinate | thiol | platinum complex |
| halotriazines | amines/anilines | aminotriazines |
| halotriazines | alcohols/phenols | triazinyl ethers |
| halotriazines | thiols | triazinyl thioethers |
| imido esters | amines/anilines | amidines |
| isocyanates | amines/anilines | ureas |
| isocyanates | alcohols/phenols | urethanes |
| isothiocyanates | amines/anilines | thioureas |
| maleimides | thiols | thioethers |
| phosphoramidite s | alcohols | phosphite esters |
| silyl halides | alcohols | silyl ethers |
| sulfonate esters | amines/anilines | alkyl amines |
| sulfonate esters | thiols | thioethers |
| sulfonate esters | carboxylic acids | esters |
| sulfonate esters | alcohols | ethers |
| sulfonyl halides | amines/anilines | sulfonamides |
| sulfonyl halides | phenols/alcohols | sulfonate esters |

As used herein, the term "bioconjugate" or "bioconjugate linker" refers to the resulting association between atoms or molecules of bioconjugate reactive groups. The association can be direct or indirect. For example, a conjugate between a first bioconjugate reactive group (e.g., "*MERGEFORMAT*MERGEFORMAT —$NH_2$, —COOH, —N— hydroxysuccinimide, or -maleimide) and a second bioconjugate reactive group (e.g., sulfhydryl, sulfur-containing amino acid, amine, amine sidechain containing amino acid, or carboxylate) provided herein can be direct, e.g., by covalent bond or linker (e.g., a first linker of second linker), or indirect, e.g., by non-covalent bond (e.g., electrostatic interactions (e.g., ionic bond, hydrogen bond, halogen bond), van der Waals interactions (e.g., dipole-dipole, dipole-induced dipole, London dispersion), ring stacking (pi effects), hydrophobic interactions and the like). In embodiments, bioconjugates or bioconjugate linkers are formed using bioconjugate chemistry (i.e., the association of two bioconjugate reactive groups) including, but not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982. In embodiments, the first bioconjugate reactive group (e.g., maleimide moiety) is covalently attached to the second bioconjugate reactive group (e.g., a sulfhydryl). In embodiments, the first bioconjugate reactive group (e.g., haloacetyl moiety) is covalently attached to the second bioconjugate reactive group (e.g., a sulfhydryl). In embodiments, the first bioconjugate reactive group (e.g., pyridyl moiety) is covalently attached to the second bioconjugate reactive group (e.g., a sulfhydryl). In embodiments, the first bioconjugate reactive group (e.g., —N— hydroxysuccinimide moiety) is covalently attached to the second bioconjugate reactive group (e.g., an amine). In embodiments, the first bioconjugate reactive group (e.g., maleimide moiety) is covalently attached to the second bioconjugate reactive group (e.g., a sulfhydryl). In embodiments, the first bioconjugate reactive groups (e.g., dibenzocyclooctyne (DBCO)) is covalently attached to the second bioconjugate reactive group (e.g., an azide). In embodiments, the first bioconjugate reactive group (e.g., -sulfo-N-hydroxysuccinimide moiety) is covalently attached to the second bioconjugate reactive group (e.g., an amine). In embodiments, the first bioconjugate reactive group (e.g., —COOH) is covalently attached to the second bioconjugate reactive group (e.g., 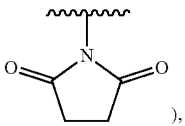), thereby forming a bioconjugate (e.g., 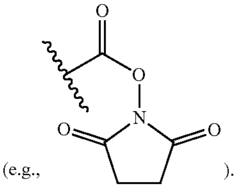 [SMILES: *C(=O)ON1C(=O)CCC1=O]).

In embodiments, the first bioconjugate reactive group (e.g., —$NH_2$) is covalently attached to the second bioconjugate reactive group (e.g., 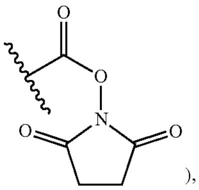), thereby forming a bioconjugate (e.g., 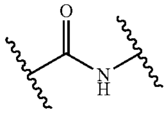).

The bioconjugate reactive groups can be chosen such that they do not participate in, or interfere with, the chemical stability of the conjugate described herein. Alternatively, a reactive functional group can be protected from participating in the crosslinking reaction by the presence of a protecting group. In embodiments, the bioconjugate comprises a molecular entity derived from the reaction of an unsaturated bond, such as a maleimide, and a sulfhydryl group.

Useful bioconjugate reactive groups used for bioconjugate chemistries herein include, for example: (a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters; (b) hydroxyl groups which can be converted to esters, ethers, aldehydes, etc.; (c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom; (d) dienophile groups which are capable of participating in Diels-Alder reactions such as, for example, maleimido or maleimide groups; (e) aldehyde or ketone groups such that subsequent derivatization is possible via formation of carbonyl derivatives such as, for example, imines, hydrazones, semicarbazones or oximes, or via such mechanisms as Grignard addition or alkyllithium addition; (f) sulfonyl halide groups for subsequent reaction with amines, for example, to form sulfonamides; (g) thiol groups, which can be converted to disulfides, reacted with acyl halides, or bonded to metals such as gold, or react with maleimides; (h) amine or sulfhydryl groups (e.g., present in cysteine), which can be, for example, acylated, alkylated or oxidized; (i) alkenes, which can undergo, for example, cycloadditions, acylation, Michael addition, etc.; (j) epoxides, which can react with, for example, amines and hydroxyl compounds; (k) phosphoramidites and other standard functional groups useful in nucleic acid synthesis; (l) metal silicon oxide bonding; (m) metal bonding to reactive phosphorus groups (e.g., phosphines) to form, for example, phosphate diester bonds; (n) azides coupled to alkynes using copper catalyzed cycloaddition click chemistry; (o) biotin conjugate can react with avidin or strepavidin to form a avidin-biotin complex or streptavidin-biotin complex.

An "antibody" (Ab) is a protein that binds specifically to a particular substance, known as an "antigen" (Ag). An "antibody" or "antigen-binding fragment" is an immunoglobulin that binds a specific "epitope." The term encompasses polyclonal, monoclonal, and chimeric antibodies. In nature, antibodies are generally produced by lymphocytes in response to immune challenge, such as by infection or immunization. An "antigen" (Ag) is any substance that reacts specifically with antibodies or T lymphocytes (T cells). An antibody may include the entire antibody as well as any antibody fragments capable of binding the antigen or antigenic fragment of interest. Examples include complete antibody molecules, antibody fragments, such as Fab, F(ab')2, CDRs, VL, VH, and any other portion of an antibody which is capable of specifically binding to an antigen. Antibodies used herein are immunospecific for, and therefore specifically and selectively bind to, for example, proteins either detected (e.g., biological targets of interest) or used for detection (e.g., probes containing oligonucleotide barcodes) in the methods and devices as described herein.

As used herein, the term "control" or "control experiment" is used in accordance with its plain and ordinary meaning and refers to an experiment in which the subjects, cells, tissues, or reagents of the experiment are treated as in a parallel experiment except for omission of a procedure, reagent, or variable of the experiment. In some instances, the control is used as a standard of comparison in evaluating experimental effects. In embodiments, a control cell is the same cell type as the cell being examined, wherein the control cell does not include the variable or is subjected to conditions being examined.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

II. Compositions and Kits

In an aspect is provided a polynucleotide including a plurality of units. In embodiments, each unit includes a portion of a genomic sequence and a padlock probe primer, wherein each padlock primer is a single-stranded polynucleotide having a 5' and a 3' end and includes: a) an oligonucleotide barcode from a known set of barcodes, and further includes a primer binding sequence from a known set of primer binding sequences (e.g., a known set of sequencing primer binding sequences). In embodiments, the polynucleotide is within a cell. In embodiments, the polynucleotide includes three or more units. In embodiments, the padlock probe has a first domain that is capable of hybridizing to a first target sequence domain, and a second domain capable of hybridizing to an adjacent second target sequence domain. In embodiments, the length of the first domain and second domain are the same length (e.g., both the first and the second domains are about 15 nucleotides). In embodiments, the length of the first domain and second domain are different lengths (e.g., the first domain is about 10 nucleotides and the second domain is about 20 nucleotides). In embodiments, an asymmetric padlock probe (i.e., a padlock probe having a first domain and second domain that are different lengths) may be advantageous in preventing non-specific hybridization. In embodiments, the total length of the first domain and second domain combined is about 25, 30, 35, or 40 nucleotides. In embodiments, the total length of the first domain and second domain combined is about 30 nucleotides.

In an aspect, provided herein are kits for use in accordance with any of the compounds, compositions, or methods disclosed herein, and including one or more elements thereof. In embodiments, a kit includes labeled nucleotides including differently labeled nucleotides, enzymes, buffers, oligonucleotides, and related solvents and solutions. In embodiments, the kit includes a padlock probe (e.g., a padlock primer as described herein). The kit may also include a template nucleic acid (DNA and/or RNA), one or more primer polynucleotides, nucleoside triphosphates (including, e.g., deoxyribonucleotides, dideoxynucleotides, ribonucleotides, labeled nucleotides, and/or modified nucleotides), buffers, salts, and/or labels (e.g., fluorophores). In embodiments, the kit includes components useful for circularizing template polynucleotides using chemical ligation techniques. In embodiments, the kit includes components useful for circularizing template polynucleotides using a ligation enzyme (e.g., Circligase enzyme, Taq DNA Ligase, HiFi Taq DNA Ligase, T4 ligase, or Ampligase DNA Ligase). In embodiments the ligation enzyme is an RNA-dependent DNA ligase (e.g., Splint® ligase). For example, such a kit further includes the following components: (a) reaction buffer for controlling pH and providing an optimized salt composition for a ligation enzyme (e.g., Circligase enzyme, Taq DNA Ligase, HiFi Taq DNA Ligase, T4 ligase, or Ampligase DNA Ligase), and (b) ligation enzyme cofactors. In embodiments, the kit further includes instructions for use thereof. In embodiments, kits described herein include a polymerase. In embodiments, the polymerase is a DNA polymerase. In embodiments, the DNA polymerase is a thermophilic nucleic acid polymerase. In embodiments, the DNA polymerase is a modified archaeal DNA polymerase. In embodiments, the kit includes a sequencing solution. In embodiments, the sequencing solution include labeled nucleotides including differently labeled nucleotides, wherein the label (or lack thereof) identifies the type of nucleotide. For example, each adenine nucleotide, or analog thereof; a thymine nucleotide; a cytosine nucleotide, or analog thereof; and a guanine nucleotide, or analog thereof may be labeled with a different fluorescent label.

III. Methods

In an aspect is provided a method of profiling a sample (e.g., a cell). In embodiments, the method includes determining information (e.g., gene and protein expression) about the transcriptome of an organism thus elucidating subcellular substances and processes. In embodiments, the method includes simultaneously identifying a plurality of RNA transcripts or proteins in situ within an optically resolved volume of a sample (e.g., a voxel). RNA transcripts are responsible for the process of converting DNA into an organism's phenotype, thus by determining the types and quantity of RNA present in a sample (e.g., a cell), it is possible to assign a phenotype to the cell. RNA transcripts include coding RNA and non-coding RNA molecules, such as messenger RNA (mRNA), transfer RNA (tRNA), micro RNA (miRNA), small interfering RNA (siRNA), small nucleolar RNA (snoRNA), small nuclear RNA (snRNA), Piwi-interacting RNA (piRNA), enhancer RNA (eRNA), or ribosomal RNA (rRNA). In embodiments, the target is pre-mRNA. In embodiments, the target is heterogeneous nuclear RNA (hnRNA).

In an aspect is provided a method of detecting a plurality of different targets within an optically resolved volume of a cell in situ. In embodiments, the method includes i) associating a different oligonucleotide barcode from a known set of barcodes with each of the plurality of targets; ii) sequencing each barcode to obtain a multiplexed signal in the cell in situ; iii) demultiplexing the multiplexed signal by comparison with the known set of barcodes; and iv) detecting the plurality of targets by identifying the associated barcodes detected in the cell. In embodiments, the method includes detecting a plurality of targets (e.g., a nucleic acid sequence or a protein) within an optically resolved volume of a sample (e.g., a voxel). In embodiments, the method includes i) associating an oligonucleotide barcode with each of the plurality of targets; ii) sequencing each barcode to obtain a multiplexed signal; and iii) demultiplexing the multiplexed signal to obtain a set of signals corresponding to barcodes with a specified Hamming distance; thereby detecting a plurality of targets within an optically resolved volume of a sample.

In an aspect is provided a method of detecting a plurality of different nucleic acid sequences within an optically resolved volume of a cell in situ, wherein the method includes i) associating a different oligonucleotide barcode from a known set of barcodes with each of the plurality of targets, wherein associating an oligonucleotide barcode with each of the plurality of targets includes hybridizing a padlock probe to two adjacent nucleic acid sequences of the target, wherein the padlock probe is a single-stranded polynucleotide having a 5' and a 3' end, and wherein the padlock probe includes a primer binding sequence from a known set of primer binding sequences; ii) sequencing each barcode to obtain a multiplexed signal in the cell in situ; iii) demultiplexing the multiplexed signal by comparison with the known set of barcodes; and iv) detecting the plurality of targets by identifying the associated barcodes detected in the cell.

In another aspect is provided a method of detecting a plurality of carbohydrates within an optically resolved volume of a cell in situ, wherein the method includes i) associating a different oligonucleotide barcode from a known set of barcodes with each of the plurality of targets, wherein associating an oligonucleotide barcode with each of the plurality of targets includes contacting each of the targets with a specific binding reagent, wherein the specific binding reagent includes an oligonucleotide barcode; ii) hybridizing a padlock probe to two adjacent nucleic acid sequences of the barcode, wherein the padlock probe is a single-stranded polynucleotide having a 5' and a 3' end, and wherein the padlock probe includes a primer binding sequence from a known set of primer binding sequences; iii) sequencing each barcode to obtain a multiplexed signal in the cell in situ; iv) demultiplexing the multiplexed signal by comparison with the known set of barcodes; and v) detecting the plurality of targets by identifying the associated barcodes detected in the cell.

In another aspect is provided a method of detecting a plurality of proteins (e.g., different proteins) within an optically resolved volume of a cell in situ, wherein the method includes i) associating a different oligonucleotide barcode from a known set of barcodes with each of the plurality of targets, wherein associating an oligonucleotide barcode with each of the plurality of targets includes contacting each of the targets with a specific binding reagent, wherein the specific binding reagent includes an oligonucleotide barcode; ii) hybridizing a padlock probe to two adjacent nucleic acid sequences of the barcode, wherein the padlock probe is a single-stranded polynucleotide having a 5' and a 3' end, and wherein the padlock probe includes a primer binding sequence from a known set of primer binding sequences; iii) sequencing each barcode to obtain a multiplexed signal in the cell in situ; iv) demultiplexing the multiplexed signal by comparison with the known set of barcodes; and v) detecting the plurality of targets by identifying the associated barcodes detected in the cell. In another aspect is provided a method of detecting a plurality of proteins (e.g., different proteins) within an optically resolved volume of a cell in situ, wherein the method includes i) associating a different oligonucleotide barcode from a known set of barcodes with each of the plurality of targets, wherein associating an oligonucleotide barcode with each of the plurality of targets includes contacting each of the targets with a specific binding reagent, wherein the specific binding reagent includes an oligonucleotide barcode; ii) sequencing each barcode to obtain a multiplexed signal in the cell in situ; iii) demultiplexing the multiplexed signal by comparison with the known set of barcodes; and iv) detecting the plurality of targets by identifying the associated barcodes detected in the cell.

In an aspect is provided a method of detecting a plurality of different targets within an optically resolved volume of a granuloma in situ. In embodiments, the method includes i) associating a different oligonucleotide barcode from a known set of barcodes with each of the plurality of targets; ii) sequencing each barcode to obtain a multiplexed signal in the granuloma in situ; iii) demultiplexing the multiplexed signal by comparison with the known set of barcodes; and iv) detecting the plurality of targets by identifying the associated barcodes detected in the granuloma cell. In embodiments, the method includes detecting a plurality of targets (e.g., nucleic acid sequences and/or proteins) within an optically resolved volume of a granuloma sample (e.g., a voxel). In embodiments, the method includes i) associating an oligonucleotide barcode with each of the plurality of targets; ii) sequencing each barcode to obtain a multiplexed signal; and iii) demultiplexing the multiplexed signal to obtain a set of signals corresponding to barcodes with a specified Hamming distance; thereby detecting a plurality of targets within an optically resolved volume of a granuloma sample. In embodiments, the granuloma is a tuberculosis granuloma (i.e., a TB granuloma). In embodiments, the granuloma includes one or more of the following: a *Mycobacterium tuberculosis* (MTb) cell, macrophage (e.g., a histiocyte), multinucleated giant cell (e.g., Langhans giant cell), epithelioid cell, Foamy cell, and/or lymphocyte. In embodiments, the granuloma includes a *Mycobacterium tuberculosis* (MTb) nucleic acid. In embodiments, the TB granuloma is obtained from a tissue sample. In embodiments, the granuloma is a collection of a plurality of TB granuloma cells. In embodiments, the TB granuloma cell is obtained from a solid granuloma. A solid granuloma is characterized by an intact structure with the macrophage-rich center surrounded by T cells and B cells resulting in a lymphocytic cuff at the periphery. With time, however, some granulomas can undergo complex remodeling characterized by the accumulation of necrotic material that leads to the formation of caseum at the center. In embodiments, the TB granuloma cell is obtained from a caseous granuloma. The caseum may undergo liquefaction resulting in cavitation—the destructive fusion of a liquefying granuloma with an adjacent airway—which facilitates bacterial dissemination (see, e.g., Marakalala M J et al. Nat. Med. 2016; 22(5): 531-538). In embodiments, the TB granuloma cell is obtained from a subject with a cavitary or transmissive granuloma. The transmissive granuloma is characterized by high Mtb growth and dissemination, and high levels of polymorphonuclear neutrophil (PMN) (see, e.g., Ehlers S and Schaible U E. Front. Immunol. 2013; 3: 411).

In embodiments, the granuloma includes a gene for lipid sequestration and metabolism (see, e.g., Kim M J et al. EMBO Mol. Med. 2010; 2(7): 258-274), e.g., Carnitine O-acetyltransferase (CRAT), Cytochrome P450, family 1, subfamily B, polypeptide 1 (CYP1B1), Cytochrome P450, family 27, subfamily A, polypeptide 1 (CYP27A1), adipophilin (ADFP), degenerative spermatocyte homologue 1, lipid desaturase (DEGS1), acyl-CoA synthetase long chain fatty acid family member 1 (ACSL1), acyl-CoA synthetase long chain fatty acid family member 3 (ACSL3), acyl-CoA synthetase long chain fatty acid family member 4 (ACSL4), acyl-CoA synthetase long chain fatty acid family member 5 (ACSL5), saposin C (SapC), 7-Dehydrocholesterol reductase (DHCR7), abhydrolase domain containing 5 (ABHD5), ATP citrate lyase (ACLY), Emopamil binding protein (EBP), Elovl family member 5, elongation of long chain fatty acids (ELOVL5), Fatty acid desaturase 1 (FADS1), Farnesyl diphosphate synthase (FDPS), Glucosidase, beta, acid (GBA), Galactosidase, alpha (GLA), Galactosidase, beta 1 (GLB1), Glycerol-3-phosphate dehydrogenase 2 (GPD2), Hydroxyacyl-Coenzyme A dehydrogenase/3-ketoacyl-Coenzyme A thiolase/enoyl-Coenzyme A hydratase, alpha subunit (HADHA), 3-Hydroxy-3methylglutaryl-Coenzyme A reductase (HMGCR), Isopentenyl-diphosphate delta isomerase 1 (IDI1), Lipase A, lysosomal acid, cholesterol esterase (LIPA), Lanosterol synthase (LSS), Phospholipid scramblase 1 (PLSCR1), Stearoyl-CoA desaturase (SCD), Sterol-C5-desaturase (SC5DL), Sterol O-acyltransferase 1 (SOAT1), Sphingosine kinase 2 (SPHK2), Triosephosphate isomerase 1 (TPI1), and/or prosaposin (PSAP). In embodiments, the granuloma includes a gene for proteins that metabolize arachidonic acid (see, e.g., Marakalala M J et al. Nat. Med. 2016; 22(5): 531-538), e.g., Arachidonate 5-lipoxygenase (ALOX5), Arachidonate 5-lipoxygenase activating protein (ALOX5AP), and/or Leukotriene A4 hydrolase (LTA4H). In embodiments, the granuloma includes a gene for prostanoid synthesis, e.g., Cyclo-oxygenase 1 (COX1) and/or Cyclo-oxygenase 2 (COX2). In embodiments, the granuloma includes genes encoding cytokines, e.g., IFNγ and/or TGF-beta. In embodiments, the granuloma includes genes associated with immunosuppression, e.g., FOX3P and/or IL10. In embodiments, the granuloma includes genes that are involved in TB drug (e.g., rifampin, ethambutol, isoniazid, and/or pyrazinamide) resistance, e.g., rpoB, embB, inhA, and/or pncA. In embodiments, the granuloma includes the rpoB gene, or fragment thereof. In embodiments, the granuloma includes the embB gene, or fragment thereof. In embodiments, the granuloma includes the inhB gene, or fragment thereof. In embodiments, the granuloma includes the pncA gene, or fragment thereof. In embodiments, one or more of these genes comprises a mutation. In embodiments, the expression of one or more of these genes is altered (e.g., increased), relative to a normal control cell.

In embodiments, the granuloma cell is obtained (e.g., by fine-needle aspiration or surgical biopsy) from a tissue. In embodiments, the tissue is lung tissue, lymph node tissue, throat tissue, cervical tissue, intramammary tissue, inguinal tissue, mesenteric tissue, mediastinal tissue, intracranial tissue, gastrointestinal tissue, and/or bone tissue.

Typically, following a TB infection, the tissue site organizes into a granuloma, which includes of a core of infected macrophages surrounded by foamy and epithelioid macrophages, monocytes, and multinucleated giant cells (MGCs). The periphery of the granuloma includes fibroblasts which provides a fibrous capsule around the macrophage-rich core. Typically, lymphocytes are abundant at the periphery of granuloma. In embodiments, the method further comprises monitoring the disease state of an individual. In embodiments, monitoring the disease state of an individual includes comparing the plurality of detected targets in the granuloma to a control (e.g., a reference cell, such as a cell from normal lung parenchyma). In embodiments, monitoring the disease state of an individual includes comparing the plurality of detected targets in the granuloma to a plurality of detected targets in a normal cell (i.e., a cell known not to include TB). In embodiments, monitoring the disease state of an individual includes comparing the plurality of detected targets in the granuloma to a plurality of detected targets in a normal cell over a period of time. In embodiments, the comparison is performed over a period of days, weeks, months, or years.

In an aspect is provided a method of detecting a plurality of different targets within an optically resolved volume of a triple negative breast cancer (TNBC) tumor cell in situ. In embodiments, the method includes i) associating a different oligonucleotide barcode from a known set of barcodes with each of the plurality of targets; ii) sequencing each barcode to obtain a multiplexed signal in the TNBC cell in situ; iii) demultiplexing the multiplexed signal by comparison with the known set of barcodes; and iv) detecting the plurality of targets by identifying the associated barcodes detected in the TNBC cell. In embodiments, the method includes detecting a plurality of targets (e.g., a nucleic acid sequence or a protein) within an optically resolved volume of a TNBC sample (e.g., a voxel). In embodiments, the method includes i) associating an oligonucleotide barcode with each of the plurality of targets; ii) sequencing each barcode to obtain a multiplexed signal; and iii) demultiplexing the multiplexed signal to obtain a set of signals corresponding to barcodes with a specified Hamming distance; thereby detecting a plurality of targets within an optically resolved volume of a TNBC sample. In embodiments, the TNBC tumor cell is obtained after a tumor has been surgically removed. In embodiments, the TNBC tumor cell is a residual tumor cell following surgical removal of a tumor. In embodiments, the TNBC tumor cell is obtained after a tumor has been contacted with a pharmacological agent. In embodiments, the TNBC tumor cell is obtained before a tumor has been contacted with a pharmacological agent. In embodiments, the method further comprises monitoring the disease state of an individual. In embodiments, monitoring the disease state of an individual includes comparing the plurality of detected targets in the tumor cell to a reference cell. In embodiments, monitoring the disease state of an individual includes comparing the plurality of detected targets in the tumor cell to a plurality of detected targets in a normal cell. In embodiments, monitoring the disease state of an individual includes comparing the plurality of detected targets in the tumor cell to a plurality of detected targets in a normal cell over a period of time. In embodiments, the comparison is performed over a period of days, weeks, months, or years.

In embodiments, the TNBC tumor includes one or more of the following: tumor-associated macrophages (TAMs), $CD4^+$ tumor-infiltrating lymphocytes (TILs), $CD8^+$ TILs, and/or $FOXP3^+$ TILs. In embodiments, the TNBC tumor cell includes a gene involved in homologous recombination repair (see, e.g., Cocco S et al. Int. J. Mol. Sci. 2020; 21(13): 4579), e.g., BRCA1, BRCA2, ATM, BARD1, BRIP1, CDK12, CHEK1, CHEK2, FANCL, PALB2, PPP2R2A, RAD51B, RAD51C, RAD51D, and/or RAD54L. In embodiments, one or more of these genes comprises a mutation. In embodiments, the expression of one or more of these genes is altered (e.g., decreased), relative to a normal control cell.

In embodiments, the TNBC tumor cell includes a gene involved in cell cycle and proliferation (see, e.g., Sporikova Z et al. Clin. Breast Cancer. 2018; 18(5): e841-e850), e.g., MYC, NRAS, Ki-67, EGFR, MET, EPHA2, and/or TP53. In embodiments, the TNBC tumor cell includes a gene involved in chemotherapeutic resistance, e.g., TNF, VEGFA, IL-6, TNFSF10, CLU, ABCC6, EGR1, SNAI1, ABCC3, EPHX1, FASN, CXCL1, IL24, JUNB, and/or TP53I11. In embodiments, the TNBC tumor cell includes a gene involved in immune cell signaling processes, e.g., JAK1/2, STAT1/4, IRF1/7/8, and/or TNF. In embodiments, the TNBC tumor cell includes a gene involved in androgen/ estrogen metabolism, steroid synthesis, porphyrin metabolism, e.g., AR, FOXA1, KRT18, and/or XBP1. In embodiments, one or more of these genes comprises a mutation. In embodiments, the expression of one or more of these genes is altered (e.g., increased), relative to a normal control cell.

In embodiments, the TNBC tumor includes one or more of the following cell types: breast cells, persister cells, and/or cancer stem-like cells. In embodiments, the TNBC tumor is classified as a basal-like 1 subtype, basal-like 2 subtype, an immunomodulatory subtype, a mesenchymal subtype, a mesenchymal stem-like subtype, or a luminal androgen receptor subtype (see, e.g., Lehmann B D et al. J. Clin. Invest. 2011; 121(7): 2750-67).

In an aspect is provided a method of detecting a plurality of different targets within an optically resolved volume of a glioblastoma multiforme (GBM) tumor cell in situ. In embodiments, the method includes i) associating a different oligonucleotide barcode from a known set of barcodes with each of the plurality of targets; ii) sequencing each barcode to obtain a multiplexed signal in the GBM tumor cell in situ; iii) demultiplexing the multiplexed signal by comparison with the known set of barcodes; and iv) detecting the plurality of targets by identifying the associated barcodes detected in the GBM tumor cell. In embodiments, the method includes detecting a plurality of targets (e.g., a nucleic acid sequence or a protein) within an optically resolved volume of a GBM tumor sample (e.g., a voxel). In embodiments, the method includes i) associating an oligonucleotide barcode with each of the plurality of targets; ii) sequencing each barcode to obtain a multiplexed signal; and iii) demultiplexing the multiplexed signal to obtain a set of signals corresponding to barcodes with a specified Hamming distance; thereby detecting a plurality of targets within an optically resolved volume of a GBM tumor sample. In embodiments, the GBM tumor cell includes cells from the tumor microenvironment. In embodiments, the GBM tumor cell is a residual tumor cell following surgical removal of a tumor. In embodiments, the GBM tumor cell is obtained after a tumor has been contacted with a pharmacological agent. In embodiments, the GBM tumor cell is obtained before a tumor has been contacted with a pharmacological agent. In embodiments, the method further comprises monitoring the disease state of an individual. In embodiments, monitoring the disease state of an individual includes comparing the plurality of detected targets in the tumor cell to a reference cell. In embodiments, monitoring the disease state of an individual includes comparing the plurality of detected targets in the tumor cell to a plurality of detected targets in a normal cell. In embodiments, monitoring the disease state of an individual includes comparing the plurality of detected targets in the tumor cell to a plurality of detected targets in a normal cell over a period of time. In embodiments, the comparison is performed over a period of days, weeks, months, or years.

In embodiments, the GBM tumor includes one or more of the following: astrocytes, neurons, oligodendrocytes, oligodendrocyte progenitor cells, neural stem cells, microglia, monocyte-derived macrophages, tumor-associated macrophages (TAMs), neutrophils, tumor-infiltrating T cells, cytomegalovirus, herpes simplex virus, and/or Epstein-Barr virus. In embodiments, the GBM tumor cell includes a gene involved in extracellular matrix regulation (see, e.g., Klemm F et al. Cell. 2020; 181(7): 1643-1660), e.g., FN1, VCAN, THBS1, TGFB1, LGALS3, and/or ANGPTL4. In embodiments, the GMB tumor cell includes a gene involved in pro-tumorigenic macrophage polarization and inhibition of T cell activation, e.g., ANXA1 and/or GPNMB. In embodiments, the GBM tumor cell includes a microglial marker, e.g., P2RY12, TMEM119, SALL1, AHR, and/or VDR. In embodiments, the GBM tumor cell, includes a microglial homeostatic gene, e.g., CX3CR1, TMEM119, CSF1R, P2RY12, P2RY13, SELPLG, GLUT5, CD64, HLA-DR, TREM2, APOE, GPR56 and/or MARCKS. In embodiments, one or more of these genes comprises a mutation. In embodiments, the expression of one or more of these genes is altered (e.g., increased), relative to a normal control cell. In embodiments, the GBM tumor is classified based on isocitrate dehydrogenase (IDH) status (e.g., wild-type or mutant) and/or O6-methylguanine-DNA methyltransferase (MGMT) methylation status.

In embodiments, the targets can include any nucleic acid of interest. The nucleic acid can include DNA, RNA, peptide nucleic acid, morpholino nucleic acid, locked nucleic acid, glycol nucleic acid, threose nucleic acid, mixtures thereof, and hybrids thereof. In embodiments, the nucleic acid is obtained from one or more source organisms. In some embodiments, the nucleic acid can include a selected sequence or a portion of a larger sequence. In embodiments, sequencing a portion of a nucleic acid or a fragment thereof can be used to identify the source of the nucleic acid. With reference to nucleic acids, polynucleotides and/or nucleotide sequences a "portion," "fragment" or "region" can be at least 5 consecutive nucleotides, at least 10 consecutive nucleotides, at least 15 consecutive nucleotides, at least 20 consecutive nucleotides, at least 25 consecutive nucleotides, at least 50 consecutive nucleotides, at least 100 consecutive nucleotides, or at least 150 consecutive nucleotides.

In embodiments, the entire sequence of the target is about 1 to 3 kb, and only a portion of that target (e.g., 50 to 100 nucleotides) is sequenced. In embodiments, the target is about 1 to 3 kb. In embodiments, the target is about 1 to 2 kb. In embodiments, the target is about 1 kb. In embodiments, the target is about 2 kb. In embodiments, the target is less than 1 kb. In embodiments, the target is about 500 nucleotides. In embodiments, the target is about 200 nucleotides. In embodiments, the target is about 100 nucleotides. In embodiments, the target is less than 100 nucleotides. In embodiments, the target is about 5 to 50 nucleotides.

In embodiments, the target is a nucleic acid sequence. In embodiments the target is an RNA transcript. In embodiments the target is a single stranded RNA nucleic acid sequence. In embodiments, the target is an RNA nucleic acid sequence or a DNA nucleic acid sequence (e.g., cDNA). In embodiments, the target is a cDNA target nucleic acid sequence and before step i), the RNA nucleic acid sequence is reverse transcribed to generate the cDNA target nucleic acid sequence. In embodiments, the target is genomic DNA (gDNA), mitochondrial DNA, chloroplast DNA, episomal DNA, viral DNA, or copy DNA (cDNA). In embodiments, the target is coding RNA such as messenger RNA (mRNA), and non-coding RNA (ncRNA) such as transfer RNA (tRNA), microRNA (miRNA), small nuclear RNA (snRNA), or ribosomal RNA (rRNA). In embodiments, the target is a cancer-associated gene. In embodiments, to minimize any amplification error or bias, the target is not reverse transcribed to generate cDNA.

In embodiments, the targets are RNA nucleic acid sequences or DNA nucleic acid sequences. In embodiments, the targets are RNA nucleic acid sequences or DNA nucleic acid sequences from the same cell. In embodiments, the targets are RNA nucleic acid sequences. In embodiments, the RNA nucleic acid sequence is stabilized using known techniques in the art. For example, RNA degradation by RNase should be minimized using commercially available solutions, e.g., RNA Later®, RNA Lysis Buffer, or Keratinocyte serum-free medium). In embodiments, the targets are messenger RNA (mRNA), transfer RNA (tRNA), micro RNA (miRNA), small interfering RNA (siRNA), small nucleolar RNA (snoRNA), small nuclear RNA (snRNA), Piwi-interacting RNA (piRNA), enhancer RNA (eRNA), or ribosomal RNA (rRNA). In embodiments, the target is pre-mRNA. In embodiments, the target is heterogeneous nuclear RNA (hnRNA). In embodiments, the target is mRNA, tRNA (transfer RNA), rRNA (ribosomal RNA), or noncoding RNA (such as lncRNA (long noncoding RNA)). In embodiments, the targets are on different regions of the same RNA nucleic acid sequence. In embodiments, the targets are cDNA target nucleic acid sequences and before step i), the RNA nucleic acid sequences are reverse transcribed to generate the cDNA target nucleic acid sequences. In embodiments, the targets are not reverse transcribed to cDNA. In embodiments, the target nucleic acid includes a nucleic acid sequence encoding a TCR alpha chain, a TCR beta chain, a TCR delta chain, a TCR gamma chain, or any fragment thereof (e.g., variable regions including VDJ or VJ regions, constant regions, transmembrane regions, fragments thereof, combinations thereof, and combinations of fragments thereof). In embodiments, the target nucleic acid includes a nucleic acid sequence encoding a B cell receptor heavy chain, B cell receptor light chain, or any fragment thereof (e.g., variable regions including VDJ or VJ regions, constant regions, transmembrane regions, fragments thereof, combinations thereof, and combinations of fragments thereof). In embodiments, the target nucleic acid includes a CDR3 nucleic acid sequence. In embodiments, the target nucleic acid includes a TCRA gene sequence or a TCRB gene sequence. In embodiments, the target nucleic acid includes a TCRA gene sequence and a TCRB gene sequence. In embodiments, the target nucleic acid includes sequences of various T cell receptor alpha variable genes (TRAV genes), T cell receptor alpha joining genes (TRAJ genes), T cell receptor alpha constant genes (TRAC genes), T cell receptor beta variable genes (TRBV genes), T cell receptor beta diversity genes (TRBD genes), T cell receptor beta joining genes (TRBJ genes), T cell receptor beta constant genes (TRBC genes), T cell receptor gamma variable genes (TRGV genes), T cell receptor gamma joining genes (TRGJ genes), T cell receptor gamma constant genes (TRGC genes), T cell receptor delta variable genes (TRDV genes), T cell receptor delta diversity genes (TRDD genes), T cell receptor delta joining genes (TRDJ genes), or T cell receptor delta constant genes (TRDC genes).

RNA, including mRNA, is highly susceptible to degradation upon exposure to one or more RNAses. RNAses are present in a wide range of locations, including water, many reagents, laboratory equipment and surfaces, skin, and mucous membranes. Working with RNA often requires preparing an RNAse-free environment and materials, as well as taking precautions to avoid introducing RNAses into an RNAse-free environment. These precautions include, but are not limited to, cleaning surfaces with an RNAse cleaning product (e.g., RNASEZAP™ and other commercially available products or 0.5% sodium dodecyl sulfate [SDS] followed by 3% $H_2 02$); using a designated workspace, materials, and equipment (e.g., pipets, pipet tips); using barrier tips; baking designated glassware (e.g., 300° C. for 2 hours) prior to use; treating enzymes, reagents, and other solutions (e.g., with diethyl pyrocarbonate [DEPC] or dimethyl pyrocarbonate [DMPC]) or using commercially available, certified RNAse-free water or solutions, or ultrafiltered water (e.g., for Tris-based solutions); including an RNAse inhibitor while avoiding temperatures or denaturing conditions that could deactivate the inhibitor); and wearing clean gloves (while avoiding contaminated surfaces) and a clean lab coat.

In embodiments, the targets are proteins or carbohydrates. In embodiments, the targets are proteins. In embodiments, the targets are carbohydrates. In embodiments when the target are proteins and/or carbohydrates, the method includes contacting the proteins with a specific binding reagent, wherein the specific binding reagent comprises an oligonucleotide barcode. In embodiments, the specific binding reagent comprises an antibody, single-chain Fv fragment (scFv), antibody fragment-antigen binding (Fab), or an aptamer. In embodiments, the specific binding reagent is a peptide, a cell penetrating peptide, an aptamer, a DNA aptamer, an RNA aptamer, an antibody, an antibody fragment, a light chain antibody fragment, a single-chain variable fragment (scFv), a lipid, a lipid derivative, a phospholipid, a fatty acid, a triglyceride, a glycerolipid, a glycerophospholipid, a sphingolipid, a saccharolipid, a polyketide, a polylysine, polyethyleneimine, diethylaminoethyl (DEAE)-dextran, cholesterol, or a sterol moiety. In embodiments, the specific binding reagent interacts (e.g., contacts, or binds) with one or more specific binding reagents on the cell surface. Carbohydrate-specific antibodies are known in the art, see for example Kappler, K., Hennet, T. Genes Immun 21, 224-239 (2020).

In embodiments, associating an oligonucleotide barcode with each of the plurality of targets includes hybridizing a padlock probe to two adjacent nucleic acid sequences of the target, wherein the padlock probe is a single-stranded polynucleotide having a 5' and a 3' end, and the padlock probe includes at least one oligonucleotide barcode, and at least one primer binding sequence. In embodiments, the oligonucleotide barcode includes at least two primer binding sequences. In embodiments, the oligonucleotide barcode includes an amplification primer binding sequence. In embodiments, the oligonucleotide barcode includes a sequencing primer binding sequence. The amplification primer binding sequence refers to a nucleotide sequence that is complementary to a primer useful in initiating amplification (i.e., an amplification primer). Likewise, a sequencing primer binding sequence is a nucleotide sequence that is complementary to a primer useful in initiating sequencing (i.e., a sequencing primer). Primer binding sequences usually have a length in the range of between 3 to 36 nucleotides, also 5 to 24 nucleotides, also from 14 to 36 nucleotides. In embodiments, an amplification primer and a sequencing primer are complementary to the same primer binding sequence, or overlapping primer binding sequences. In embodiments, an amplification primer and a sequencing primer are complementary to different primer binding sequences. In embodiments, the primer binding sequence is complementary to a fluorescent in situ hybridization (FISH) probe. FISH probes may be custom designed using known techniques in the art, see for example Gelali, E., Girelli, G., Matsumoto, M. et al. Nat Commun 10, 1636 (2019).

In embodiments, the padlock probe includes a primer binding sequence from a known set of primer binding sequences. In embodiments, the padlock probe includes only one primer binding sequence, wherein the primer binding sequence serves as the amplification primer binding sequence and sequencing primer binding sequence. In embodiments, the padlock probe includes at least two primer binding sequences from a known set of primer binding sequences. In embodiments, the padlock probe includes two or more primer binding sequences from a known set of primer binding sequences. In embodiments, the padlock probe includes up to 50 different primer binding sequences from a known set of primer binding sequences. In embodiments, the padlock probe includes up to 10 different primer binding sequences from a known set of primer binding sequences. In embodiments, the padlock probe includes up to 5 different primer binding sequences from a known set of primer binding sequences. In embodiments, the padlock probe includes two or more sequencing primer binding sequences from a known set of sequencing primer binding sequences. In embodiments, the padlock probe includes 1, 2, 3, 4, 5, 6, 7, 8, 9, or 10 primer binding sequences from a known set of primer binding sequences. In embodiments, the padlock probe includes two or more different primer binding sequences from a known set of primer binding sequences. In embodiments, the padlock probe includes 1, 2, 3, 4, 5, 6, 7, 8, 9, or 10 different primer binding sequences from a known set of primer binding sequences. In embodiments, the padlock probe includes 2 to 5 primer binding sequences from a known set of primer binding sequences. In embodiments, the padlock probe includes 2 to 5 different primer binding sequences from a known set of primer binding sequences. In embodiments, the padlock probe includes 2 to 5 sequencing primer binding sequences from a known set of sequencing primer binding sequences. In embodiments, the padlock probe includes 2 to 5 different sequencing primer binding sequences from a known set of sequencing primer binding sequences.

In embodiments, the padlock probe includes one oligonucleotide barcode, and one primer binding sequence. In embodiments, the padlock probe includes at least two (optionally different) oligonucleotide barcodes, and at least two different primer binding sequences. In embodiments, the padlock probe includes at least two (optionally different) oligonucleotide barcodes, and at least two different sequencing primer binding sequences. In embodiments, the padlock probe includes two different oligonucleotide barcodes and two different sequencing primer binding sequences. In embodiments, the padlock probe includes identical oligonucleotide barcodes and two different sequencing primer binding sequences.

In embodiments, the known set of primer binding sequences includes at least 2 different primer binding sequences. In embodiments, the known set of primer binding sequences includes two or more different primer binding sequences. In embodiments, the known set of primer binding sequences includes at least 3 different primer binding sequences. In embodiments, the known set of primer binding sequences includes three or more different primer binding sequences. In embodiments, the known set of primer binding sequences includes at least 2 different sequencing primer binding sequences. In embodiments, the known set of primer binding sequences includes two or more different sequencing primer binding sequences. In embodiments, the known set of primer binding sequences includes 2 to 10 different sequencing primer binding sequences. In embodiments, the known set of primer binding sequences includes 2 to 6 different sequencing primer binding sequences. In embodiments, the known set of primer binding sequences includes 3 to 8 different sequencing primer binding sequences.

Padlock probes are specialized ligation probes, examples of which are known in the art, see for example Nilsson M, et al. Science. 1994; 265(5181):2085-2088), and has been applied to detect transcribed RNA in cells, see for example Christian A T, et al. Proc Natl Acad Sci USA. 2001; 98(25):14238-14243, both of which are incorporated herein by reference in their entireties. In embodiments, the padlock probe is approximately 50 to 200 nucleotides. In embodiments, a padlock probe has a first domain that is capable of hybridizing to a first target sequence domain, and a second ligation domain, capable of hybridizing to an adjacent second sequence domain. The configuration of the padlock probe is such that upon ligation of the first and second ligation domains of the padlock probe, the probe forms a circular polynucleotide, and forms a complex with the sequence (i.e., the sequence it hybridized to, the target sequence) wherein the target sequence is "inserted" into the loop of the circle. Padlock probes are useful for the methods provided herein and include, for example, padlock probes for genomic analyses, as exemplified by Gore, A. et al. Nature 471, 63-67 (2011); Porreca, G. J. et al. Nat Methods 4, 931-936 (2007); Li, J. B. et al. Genome Res 19, 1606-1615 (2009), Zhang, K. et al. Nat Methods 6, 613-618 (2009); Noggle, S. et al. Nature 478, 70-75 (2011); and Li, J. B. et al. Science 324, 1210-1213 (2009), the content of each of which is incorporated by reference in its entirety.

In embodiments, the padlock probe includes at least one target-specific region. A target-specific region is a single stranded polynucleotide that is at least 50% complementary, at least 75% complementary, at least 85% complementary, at least 90% complementary, at least 95% complementary, at least 98%, at least 99% complementary, or 100% complementary to a portion of a nucleic acid molecule that includes a target sequence (e.g., a gene of interest). In embodiments, the target-specific region is capable of hybridizing to at least a portion of the target sequence. In embodiments, the target-specific region is substantially non-complementary to other target sequences present in the sample. In embodiments, the padlock probe includes at two target-specific regions.

In embodiments, the padlock probe has a first domain that is capable of hybridizing to a first target sequence domain, and a second domain capable of hybridizing to an adjacent second target sequence domain. In embodiments, the length of the first domain and second domain are the same length (e.g., both the first and the second domains are about 15 nucleotides). In embodiments, the length of the first domain and second domain are different lengths (e.g., the first domain is about 10 nucleotides and the second domain is about 20 nucleotides). In embodiments, an asymmetric padlock probe (i.e., a padlock probe having a first domain and second domain that are different lengths) may be advantageous in preventing non-specific hybridization. In embodiments, the total length of the first domain and second domain is about 25, 30, 35, or 40 nucleotides. In embodiments, the total length of the first domain and second domain is about 30 nucleotides.

In embodiments, the method further includes ligating the 5' and 3' ends of the padlock probe to form a circular polynucleotide (i.e., a polynucleotide that is a continuous strand lacking free 5' and 3' ends). In embodiments, the method includes ligating the 5' and 3' ends of the padlock probe to form a circular polynucleotide, wherein the circular polynucleotide includes the target nucleic acid. In embodiments, the method includes ligating the 5' and 3' ends of the padlock probe to form a circular polynucleotide, wherein the circular polynucleotide includes the oligonucleotide barcode. In embodiments, the ligation includes enzymatic ligation. In embodiments, ligating includes enzymatic ligation including a ligation enzyme (e.g., Circligase enzyme, Taq DNA Ligase, HiFi Taq DNA Ligase, T4 ligase, PBCV-1 DNA Ligase (also known as Splint® ligase) or Ampligase DNA Ligase). Non-limiting examples of ligases include DNA ligases such as DNA Ligase I, DNA Ligase II, DNA Ligase III, DNA Ligase IV, T4 DNA ligase, T7 DNA ligase, T3 DNA Ligase, *E. coli* DNA Ligase, PBCV-1 DNA Ligase (also known as Splint® ligase) or a Taq DNA Ligase. In embodiments, the ligase enzyme includes a T4 DNA ligase, T4 RNA ligase 1, T4 RNA ligase 2, T3 DNA ligase or T7 DNA ligase. In embodiments, the enzymatic ligation is performed by a mixture of ligases. In embodiments, the ligation enzyme is selected from the group consisting of T4 DNA ligase, T4 RNA ligase 1, T4 RNA ligase 2, RtcB ligase, T3 DNA ligase, T7 DNA ligase, Taq DNA ligase, PBCV-1 DNA Ligase, a thermostable DNA ligase (e.g., 5'AppDNA/RNA ligase), an ATP dependent DNA ligase, an RNA-dependent DNA ligase (e.g., Splint® ligase), and combinations thereof.

In embodiments, ligating includes chemical ligation (e.g., enzyme-free, click-mediated ligation). In embodiments, the oligonucleotide primer includes a first bioconjugate reactive moiety capable of bonding upon contact with a second (complementary) bioconjugate reactive moiety. In embodiments, the oligonucleotide primer includes an alkynyl moiety at the 3' and an azide moiety at the 5' end that, upon hybridization to the target nucleic acid react to form a triazole linkage during suitable reaction conditions. Reaction conditions and protocols for chemical ligation techniques that are compatible with nucleic acid amplification methods are known in the art, for example El-Sagheer, A. H., & Brown, T. (2012). *Accounts of chemical research,* 45(8), 1258-1267; Manuguerra I. et al. *Chem Commun* (*Camb*). 2018; 54(36):4529-4532; and Odeh, F., et al. (2019). *Molecules* (*Basel, Switzerland*), 25(1), 3, each of which is incorporated herein by reference in their entirety.

In embodiments, the method includes hybridizing a padlock probe to two adjacent nucleic acid sequences of the target, wherein the padlock probe is a single-stranded polynucleotide having a 5' and a 3' end, and the padlock probe comprises at least one oligonucleotide barcode, at least one amplification primer binding sequence, and at least one sequencing primer binding sequence. In embodiments, the target nucleic acid serves as a splint for the padlock probe.

In embodiments, associating an oligonucleotide barcode with each of the plurality of targets includes contacting each of the targets with a specific binding reagent, wherein the specific binding reagent includes an oligonucleotide barcode. In embodiments, the method further includes hybridizing a padlock probe to two adjacent nucleic acid sequences of the barcode, wherein the padlock probe is a single-stranded polynucleotide having a 5' and a 3' end, and the padlock probe includes at least one primer binding sequence. In embodiments, the method further includes ligating the 5' and 3' ends of the padlock probe to form a circular polynucleotide. In embodiments, the probe includes a primer binding sequence from a known set of primer binding sequences. In embodiments, the probe includes a sequencing primer binding sequence from a known set of sequencing primer binding sequences.

In embodiments, associating an oligonucleotide barcode with each of the plurality of targets includes contacting each of the targets with a specific binding reagent, wherein the specific binding reagent includes a circular polynucleotide which includes the oligonucleotide barcode. For example, in embodiments the specific binding reagent is bound (e.g., covalently linked via a tethered capture oligonucleotide, wherein the capture oligonucleotide is hybridized to the circular polynucleotide) to a circular polynucleotide before contacting the target. In embodiments, the specific binding reagent includes an antibody, single-chain Fv fragment (scFv), antibody fragment-antigen binding (Fab), or an aptamer. In embodiments, the specific binding reagent is an antibody, single-chain Fv fragment (scFv), antibody fragment-antigen binding (Fab), or an aptamer. In embodiments, the circular polynucleotide includes a primer binding sequence from a known set of primer binding sequences.

In embodiments, the barcode is at least 5, 6, 7, 8, 9, 10, 11, 12, 13, 14, or 15 nucleotides in length. In embodiments, the barcode is 5, 6, 7, 8, 9, 10, 11, 12, 13, 14, or 15 nucleotides in length. In embodiments, the barcode is 10 to 15 nucleotides in length. An oligonucleotide barcode is at least about 1, 2, 3, 4, 5, 6, 7, 8, 9, 10, 15, 20, 25, 30, 35, 40, 45, 50 or more nucleotides in length. An oligonucleotide barcode can be at most about 300, 200, 100, 90, 80, 70, 60, 50, 40, 30, 20, 15, 12, 10, 9, 8, 7, 6, 5, 4 or fewer or more nucleotides in length. In embodiments, an oligonucleotide barcode includes between about 5 to about 8, about 5 to about 10, about 5 to about 15, about 5 to about 20, about 10 to about 150 nucleotides. In embodiments, an oligonucleotide barcode includes between 5 to 8, 5 to 10, 5 to 15, 5 to 20, 10 to 150 nucleotides. In embodiments, an oligonucleotide barcode is less than 10 nucleotides. In embodiments, an oligonucleotide barcode is about 10 nucleotides. In embodiments, an oligonucleotide barcode is 10 nucleotides. An oligonucleotide barcode may include a unique sequence (e.g., a barcode sequence) that gives the oligonucleotide barcode its identifying functionality. The unique sequence may be random or non-random. Attachment of the barcode sequence to a nucleic acid of interest (i.e., the target) may associate the barcode sequence with the nucleic acid of interest. The barcode may then be used to identify the nucleic acid of interest during sequencing, even when other nucleic acids of interest (e.g., comprising different oligonucleotide barcodes) are present. In embodiments, the oligonucleotide barcode consists only of a unique barcode sequence. In embodiments, the 5' end of a barcoded oligonucleotide is phosphorylated. In embodiments, the oligonucleotide barcode is known (i.e., the nucleic sequence is known before sequencing) and is sorted into a basis-set according to their Hamming distance. Oligonucleotide barcodes can be associated with a target of interest by knowing, a priori, the target of interest, such as a gene or protein. In embodiments, the oligonucleotide barcodes further include one or more sequences capable of specifically binding a gene or nucleic acid sequence of interest. For example, in embodiments, the oligonucleotide barcode include a sequence capable of hybridizing to mRNA, e.g., one containing a poly-T sequence (e.g., having several T's in a row, e.g., 4, 5, 6, 7, 8, or more T's). In embodiments, the padlock probe is at least about 50, 60, 70, 80, 90, 100, 110, 120, 130 or more nucleotides in length. In embodiments, the padlock probe is at most about 300, 200, 100, 90, 80, or fewer or more nucleotides in length. In embodiments, the total length of the padlock probe is about 80, 90, 100, 110, 120, 130, or 140 nucleotides in length.

In embodiments, the oligonucleotide barcode is included as part of an oligonucleotide of longer sequence length, such as a primer or a random sequence (e.g., a random N-mer). In embodiments, the oligonucleotide barcode contains random sequences to increase the mass or size of the oligonucleotide tag. The random sequence can be of any suitable length, and there may be one or more than one present. As non-limiting examples, the random sequence may have a length of 10 to 40, 10 to 30, 10 to 20, 25 to 50, 15 to 40, 15 to 30, 20 to 50, 20 to 40, or 20 to 30 nucleotides.

In embodiments, the oligonucleotide barcode is a nucleic acid molecule which can hybridize specifically to a target (e.g., a nucleic acid of interest). The unique identifier sequence of the barcode can be a nucleic acid sequence which associates the oligonucleotide barcode with the nucleic acid of interest to which it hybridizes.

In embodiments, the oligonucleotide barcode is taken from a "pool" or "set" or "basis-set" of potential oligonucleotide barcode sequences. The set of oligonucleotide barcodes may be selected using any suitable technique, e.g., randomly, or such that the sequences allow for error detection and/or correction, or having a particular feature, such as by being separated by a certain distance (e.g., Hamming distance). In embodiments, the method includes selecting a basis-set of oligonucleotide barcodes having a specified Hamming distance (e.g., a Hamming distance of 10; a Hamming distance of 5). The pool may have any number of potential barcode sequences, e.g., at least 100, at least 300, at least 500, at least 1,000, at least 3,000, at least 5,000, at least 10,000, at least 30,000, at least 50,000, at least 100,000, at least 300,000, at least 500,000, or at least 1,000,000 barcode sequences.

In embodiments, the cell forms part of a tissue in situ. In embodiments, the cell is an isolated single cell. In embodiments, the cell is a prokaryotic cell. In embodiments, the cell is a eukaryotic cell. In embodiments, the cell is a bacterial cell, a fungal cell, a plant cell, or a mammalian cell. In embodiments, the cell is a stem cell. In embodiments, the stem cell is an embryonic stem cell, a tissue-specific stem cell, a mesenchymal stem cell, or an induced pluripotent stem cell. In embodiments, the cell is an endothelial cell, muscle cell, myocardial, smooth muscle cell, skeletal muscle cell, mesenchymal cell, epithelial cell; hematopoietic cell, such as lymphocytes, including T cell, e.g., (Th1 T cell, Th2 T cell, ThO T cell, cytotoxic T cell); B cell, pre-B cell; monocytes; dendritic cell; neutrophils; or a macrophage. In embodiments, the cell is a stem cell, an immune cell, a cancer cell (e.g., a circulating tumor cell or cancer stem cell), a viral-host cell, or a cell that selectively binds to a desired target. In embodiments, the cell includes a T cell receptor gene sequence, a B cell receptor gene sequence, or an immunoglobulin gene sequence. In embodiments, the cell includes a Toll-like receptor (TLR) gene sequence. In embodiments, the cell includes a gene sequence corresponding to an immunoglobulin light chain polypeptide and a gene sequence corresponding to an immunoglobulin heavy chain polypeptide. In embodiments, the cell is a genetically modified cell. In embodiments, the cell is a circulating tumor cell or cancer stem cell.

In embodiments, the cell is a prokaryotic cell. In embodiments, the cell is a bacterial cell. In embodiments, the bacterial cell is a *Bacteroides, Clostridium, Faecalibacterium, Eubacterium, Ruminococcus, Peptococcus, Peptostreptococcus, Mycobacterium*, or *Bifidobacterium* cell. In embodiments, the bacterial cell is a *Bacteroides fragilis, Bacteroides melaninogenicus, Bacteroides oralis, Enterococcus faecalis, Escherichia coli, Enterobacter* sp., *Klebsiella* sp., *Bifidobacterium bifidum, Mycobacterium tuberculosis, Staphylococcus aureus, Lactobacillus, Clostridium perfringens, Proteus mirabilis, Clostridium tetani, Clostridium septicum, Pseudomonas aeruginosa, Salmonella enterica, Faecalibacterium prausnitzii, Peptostreptococcus* sp., or *Peptococcus* sp. cell. In embodiments, the cell is a fungal cell. In embodiments, the fungal cell is a *Candida, Saccharomyces, Aspergillus, Penicillium, Rhodotorula, Trametes, Pleospora, Sclerotinia, Bullera*, or a *Galactomyces* cell.

In embodiments, the cell is an adherent cell (e.g., epithelial cell, endothelial cell, or neural cell). Adherent cells are usually derived from tissues of organs and attach to a substrate (e.g., epithelial cells adhere to an extracellular matrix coated substrate via transmembrane adhesion protein complexes). Adherent cells typically require a substrate, e.g., tissue culture plastic, which may be coated with extracellular matrix (e.g., collagen and laminin) components to increase adhesion properties and provide other signals needed for growth and differentiation.

In embodiments, the cell is a leukocyte (i.e., a white-blood cell). In embodiments, leukocyte is a granulocyte (neutrophil, eosinophil, or basophil), monocyte, or lymphocyte (T cells and B cells). In embodiments, the cell is a lymphocyte.

In embodiments, the cell is a neuronal cell, an endothelial cell, epithelial cell, germ cell, plasma cell, a muscle cell, peripheral blood mononuclear cell (PBMC), a myocardial cell, or a retina cell. In embodiments, the cell is a suspension cell (e.g., a cell free-floating in the culture medium, such a lymphoblast or hepatocyte). In embodiments, the cell is a glial cell (e.g., astrocyte, radial glia), pericyte, or stem cell (e.g., a neural stem cell). In embodiments, the cell is a neuronal cell. In embodiments, the cell is an endothelial cell. In embodiments, the cell is an epithelial cell. In embodiments, the cell is a germ cell. In embodiments, the cell is a plasma cell. In embodiments, the cell is a muscle cell. In embodiments, the cell is a peripheral blood mononuclear cell (PBMC). In embodiments, the cell is a myocardial cell. In embodiments, the cell is a retina cell. In embodiments, the cell is a lymphoblast. In embodiments, the cell is a hepatocyte. In embodiments, the cell is a glial cell. In embodiments, the cell is an astrocyte. In embodiments, the cell is a radial glia. In embodiments, the cell is a pericyte. In embodiments, the cell is a stem cell. In embodiments, the cell is a neural stem cell.

In embodiments, the cell is an immune cell. In embodiments, the immune cell is a granulocyte, a mast cell, a monocyte, a neutrophil, a dendritic cell, or a natural killer (NK) cell. In embodiments, the immune cell is an adaptive cell, such as a T cell, NK cell, or a B cell. In embodiments, the cell includes a T cell receptor gene sequence, a B cell receptor gene sequence, or an immunoglobulin gene sequence. In embodiments, the immune cell is a granulocyte. In embodiments, the immune cell is a mast cell. In embodiments, the immune cell is a monocyte. In embodiments, the immune cell is a neutrophil. In embodiments, the immune cell is a dendritic cell. In embodiments, the immune cell is a natural killer (NK) cell. In embodiments, the immune cell is a T cell. In embodiments, the immune cell is a B cell. In embodiments, the cell includes a T cell receptor gene sequence. In embodiments, the cell includes a B cell receptor gene sequence. In embodiments, the cell includes an immunoglobulin gene sequence.

In embodiments, the cell is a cancer cell. In embodiments, the cancer cell includes a cancer-associated gene (e.g., an oncogene associated with kinases and genes involved in DNA repair) or a cancer-associated biomarker. A "biomarker" is a substance that is associated with a particular characteristic, such as a disease or condition. A change in the levels of a biomarker may correlate with the risk or progression of a disease or with the susceptibility of the disease to a given treatment. In embodiments, the cancer is Acute Myeloid Leukemia, Adrenocortical Carcinoma, Bladder Urothelial Carcinoma, Breast Ductal Carcinoma, Breast Lobular Carcinoma, Cervical Carcinoma, Cholangiocarcinoma, Colorectal Adenocarcinoma, Esophageal Carcinoma, Gastric Adenocarcinoma, Glioblastoma Multiforme, Head and Neck Squamous Cell Carcinoma, Hepatocellular Carcinoma, Kidney Chromophobe Carcinoma, Kidney Clear Cell Carcinoma, Kidney Papillary Cell Carcinoma, Lower Grade Glioma, Lung Adenocarcinoma, Lung Squamous Cell Carcinoma, Mesothelioma, Ovarian Serous Adenocarcinoma, Pancreatic Ductal Adenocarcinoma, Paraganglioma & Pheochromocytoma, Prostate Adenocarcinoma, Sarcoma, Skin Cutaneous Melanoma, Testicular Germ Cell Cancer, Thymoma, Thyroid Papillary Carcinoma, Uterine Carcinosarcoma, Uterine Corpus Endometrioid Carcinoma, or Uveal Melanoma. In embodiments, the cancer-associated gene is a nucleic acid sequence identified within The Cancer Genome Atlas Program, accessible at www.cancer.gov/tcga.

In embodiments, the cancer-associated biomarker is MDC, NME-2, KGF, P1GF, Flt-3L, HGF, MCP1, SAT-1, MIP-1-b, GCLM, OPG, TNF RII, VEGF-D, ITAC, MMP-10, GPI, PPP2R4, AKR1B1, Amy1A, MIP-1b, P-Cadherin, or EPO. In embodiments, the cancer-associated gene is a AKT1, AKT2, AKT3, ALK, AR, ARAF, ARID1A, ATM, ATR, ATRX, AXL, BAP1, BRAF, BRCA1, BRCA2, BTK, CBL, CCND1, CCND2, CCND3, CCNE1, CDK12, CDK2, CDK4, CDK6, CDKN1B, CDKN2A, CDKN2B, CHEK1, CHEK2, CREBBP, CSF1R, CTNNB1, DDR2, EGFR, ERBB2, ERBB3, ERBB4, ERCC2, ERG, ESR1, ETV1, ETV4, ETV5, EZH2, FANCA, FANCD2, FANCI, FBXW7, FGF19, FGF3, FGFR1, FGFR2, FGFR3, FGFR4, FGR, FLT3, FOXL2, GATA2, GNA11, GNAQ, GNAS, H3F3A, HIST1H3B, HNF1A, HRAS, IDH1, IDH2, IGF1R, JAK1, JAK2, JAK3, KDR, KIT, KNSTRN, KRAS, MAGOH, MAP2K1, MAP2K2, MAP2K4, MAPK1, MAX, MDM2, MDM4, MED12, MET, MLH1, MRE11A, MSH2, MSH6, MTOR, MYB, MYBL1, MYC, MYCL, MYCN, MYD88, NBN, NF1, NF2, NFE2L2, NOTCH1, NOTCH2, NOTCH3, NOTCH4, NRAS, NRG1, NTRK1, NTRK2, NTRK3, NUTM1, PALB2, PDGFRA, PDGFRB, PIK3CA, PIK3CB, PIK3R1, PMS2, POLE, PPARG, PPP2R1A, PRKACA, PRKACB, PTCH1, PTEN, PTPN11, RAC1, RAD50, RAD51, RAD51B, RAD51C, RAD51D, RAF1, RB1, RELA, RET, RHEB, RHOA, RICTOR, RNF43, ROS1, RSPO2, RSPO3, SETD2, SF3B1, SLX4, SMAD4, SMARCA4, SMARCB1, SMO, SPOP, SRC, STAT3, STK11, TERT, TOP1, TP53, TSC1, TSC2, U2AF1, or XPO1 gene. In embodiments, the cancer-associated gene is a ABL1, AKT1, ALK, APC, ATM, BRAF, CDH1, CDKN2A, CSF1R, CTNNB1, EGFR, ERBB2, ERBB4, EZH2, FBXW7, FGFR1, FGFR2, FGFR3, FLT3, GNA11, GNAQ, GNAS, HNF1A, HRAS, IDH1, IDH2, JAK2, JAK3, KDR, KIT, KRAS, MET, MLH1, MPL, NOTCH1, NPM1, NRAS, PDGFRA, PIK3CA, PTEN, PTPN11, RB1, RET, SMAD4, SMARCB1, SMO, SRC, STK11, TP53, or VHL gene. In embodiments, the cell is a cell (e.g., a T cell) within a tumor. In embodiments, the cell is a non-allogenic cell (i.e., native cell to the subject) within a tumor. In embodiments, the cell is a tumor infiltrating lymphocyte (TIL). In embodiments, the cell is an allogenic cell. In embodiments, the cell is a circulating tumor cell.

In embodiments, the cell is a viral-host cell. A "viral-host cell" is used in accordance with its ordinary meaning in virology and refers to a cell that is infected with a viral genome (e.g., viral DNA or viral RNA). The cell, prior to infection with a viral genome, can be any cell that is susceptible to viral entry. In embodiments, the viral-host cell is a lytic viral-host cell. In embodiments, the viral-host cell is capable of producing viral protein. In embodiments, the viral-host cell is a lysogenic viral-host cell. In embodiments, the cell is a viral-host cell including a viral nucleic acid sequence, wherein the viral nucleic acid sequence is from a Hepadnaviridae, Adenoviridae, Herpesviridae, Poxviridae, Parvoviridae, Reoviridae, Coronaviridae, Retroviridae virus.

In embodiments, the cell is a cell that selectively binds to a desired target. In embodiments, the cell is a cell that selectively binds to a desired target, wherein the target is an antibody, or antigen binding fragment, an aptamer, affimer, non-immunoglobulin scaffold, small molecule, or genetic modifying agent.

In embodiments, the cell is bound to a known antigen. In embodiments, the cell is a cell that selectively binds to a desired target, wherein the target is an antibody, or antigen binding fragment, an aptamer, affimer, non-immunoglobulin scaffold, small molecule, or genetic modifying agent. In embodiments, the cell is a leukocyte (i.e., a white-blood cell). In embodiments, leukocyte is a granulocyte (neutrophil, eosinophil, or basophil), monocyte, or lymphocyte (T cells and B cells). In embodiments, the cell is a lymphocyte. In embodiments, the cell is a T cell, an NK cell, or a B cell.

In embodiments, the cell in situ is obtained from a subject (e.g., human or animal tissue). Once obtained, the cell is placed in an artificial environment in plastic or glass containers supported with specialized medium containing essential nutrients and growth factors to support proliferation. In embodiments, the cell is permeabilized and immobilized to a solid support surface. In embodiments, the cell is permeabilized and immobilized to an array (i.e., to discrete locations arranged in an array). In embodiments, the cell is immobilized to a solid support surface. In embodiments, the surface includes a patterned surface (e.g., suitable for immobilization of a plurality of cells in an ordered pattern. The discrete regions of the ordered pattern may have defined locations in a regular array, which may correspond to a rectilinear pattern, circular pattern, hexagonal pattern, or the like. These discrete regions are separated by interstitial regions. As used herein, the term "interstitial region" refers to an area in a substrate or on a surface that separates other areas of the substrate or surface. In embodiments, a plurality of cells are immobilized on a patterned surface that have a mean or median separation from one another of about 10-20 μm. In embodiments, a plurality of cells are immobilized on a patterned surface that have a mean or median separation from one another of about 10-20; 10-50; or 100 μm. In embodiments, a plurality of cells are arrayed on a substrate. In embodiments, a plurality of cells are immobilized in a 96-well microplate having a mean or median well-to-well spacing of about 8 mm to about 12 mm (e.g., about 9 mm). In embodiments, a plurality of cells are immobilized in a 384-well microplate having a mean or median well-to-well spacing of about 3 mm to about 6 mm (e.g., about 4.5 mm).

In embodiments, the cell is attached to the substrate via a bioconjugate reactive linker. In embodiments, the cell is attached to the substrate via a specific binding reagent. In embodiments, the specific binding reagent includes an antibody, single-chain Fv fragment (scFv), antibody fragment-antigen binding (Fab), or an aptamer. In embodiments, the specific binding reagent includes an antibody, or antigen binding fragment, an aptamer, affimer, or non-immunoglobulin scaffold. In embodiments, the specific binding reagent is a peptide, a cell penetrating peptide, an aptamer, a DNA aptamer, an RNA aptamer, an antibody, an antibody fragment, a light chain antibody fragment, a single-chain variable fragment (scFv), a lipid, a lipid derivative, a phospholipid, a fatty acid, a triglyceride, a glycerolipid, a glycerophospholipid, a sphingolipid, a saccharolipid, a polyketide, a polylysine, polyethyleneimine, diethylaminoethyl (DEAE)-dextran, cholesterol, or a sterol moiety. Substrates may be prepared for selective capture of particular cells. For example, a substrate containing a plurality of bioconjugate reactive moieties or a plurality of specific binding reagents, optionally in an ordered pattern, contacts a plurality of cells. Only cells containing complementary bioconjugate reactive moieties or complementary specific binding reagents are capable of reacting, and thus adhering, to the substrate.

In embodiments, the methods are performed in situ on isolated cells or in tissue sections that have been prepared according to methodologies known in the art. Methods for permeabilization and fixation of cells and tissue samples are known in the art, as exemplified by Cremer et al., The Nucleus: Volume 1: Nuclei and Subnuclear Components, R. Hancock (ed.) 2008; and Larsson et al., Nat. Methods (2010) 7:395-397, the content of each of which is incorporated herein by reference in its entirety. In embodiments, the cell is cleared (e.g., digested) of proteins, lipids, or both proteins and lipids.

In embodiments, the cell is immobilized to a substrate. The cell may have been cultured on the surface, or the cell may have been initially cultured in suspension and then fixed to the surface. Substrates can be two- or three-dimensional and can include a planar surface (e.g., a glass slide). A substrate can include glass (e.g., controlled pore glass (CPG)), quartz, plastic (such as polystyrene (low cross-linked and high cross-linked polystyrene), polycarbonate, polypropylene and poly(methylmethacrylate)), acrylic copolymer, polyamide, silicon, metal (e.g., alkanethiolate-derivatized gold), cellulose, nylon, latex, dextran, gel matrix (e.g., silica gel), polyacrolein, or composites. In embodiments, the substrate includes a polymeric coating, optionally containing bioconjugate reactive moieties capable of affixing the sample. Suitable three-dimensional substrates include, for example, spheres, microparticles, beads, membranes, slides, plates, micromachined chips, tubes (e.g., capillary tubes), microwells, microfluidic devices, channels, filters, or any other structure suitable for anchoring a sample. In embodiments, the substrate is not a flow cell. In embodiments, the substrate includes a polymer matrix material (e.g., polyacrylamide, cellulose, alginate, polyamide, cross-linked agarose, cross-linked dextran or cross-linked polyethylene glycol), which may be referred to herein as a “matrix”, “synthetic matrix”, “exogenous polymer” or “exogenous hydrogel”. In embodiments, a matrix may refer to the various components and organelles of a cell, for example, the cytoskeleton (e.g., actin and tubulin), endoplasmic reticulum, Golgi apparatus, vesicles, etc. In embodiments, the matrix is endogenous to a cell. In embodiments, the matrix is exogenous to a cell. In embodiments, the matrix includes both the intracellular and extracellular components of a cell. In embodiments, polynucleotide primers may be immobilized on a matrix including the various components and organelles of a cell. Immobilization of polynucleotide primers on a matrix of cellular components and organelles of a cell is accomplished as described herein, for example, through the interaction/reaction of complementary bioconjugate reactive moieties. In embodiments, the exogenous polymer may be a matrix or a network of extracellular components that act as a point of attachment (e.g., act as an anchor) for the cell to a substrate.

In embodiments, the cell is exposed to paraformaldehyde (i.e., by contacting the cell with paraformaldehyde). Any suitable permeabilization and fixation technologies can be used for making the cell available for the detection methods provided herein. In embodiments the method includes affixing single cells or tissues to a transparent substrate. Exemplary tissues include those from skin tissue, muscle tissue, bone tissue, organ tissue and the like. In embodiments, the method includes immobilizing the cell in situ to a substrate and permeabilized for delivering probes, enzymes, nucleotides and other components required in the reactions. In embodiments, the cell includes many cells from a tissue section in which the original spatial relationships of the cells are retained. In embodiments, the cell in situ is within a Formalin-Fixed Paraffin-Embedded (FFPE) sample. In embodiments, the cell is subjected to paraffin removal methods, such as methods involving incubation with a hydrocarbon solvent, such as xylene or hexane, followed by two or more washes with decreasing concentrations of an alcohol, such as ethanol. The cell may be rehydrated in a buffer, such as PBS, TBS or MOPs. In embodiments, the FFPE sample is incubated with xylene and washed using ethanol to remove the embedding wax, followed by treatment with Proteinase K to permeabilized the tissue. In embodiments, the cell is fixed with a chemical fixing agent. In embodiments, the chemical fixing agent is formaldehyde or glutaraldehyde. In embodiments, the chemical fixing agent is glyoxal or dioxolane. In embodiments, the chemical fixing agent includes one or more of ethanol, methanol, 2-propanol, acetone, and glyoxal. In embodiments, the chemical fixing agent includes formalin, Greenfix®, Greenfix® Plus, UPM, CyMol®, HOPE®, CytoSkelFix™, F-Solv®, FineFIX®, RCL2/KINFix, UMFIX, Glyo-Fixx®, Histochoice®, or PAXgene®. In embodiments, the cell is fixed within a synthetic three-dimensional matrix (e.g., polymeric material). In embodiments, the synthetic matrix includes polymeric-crosslinking material. In embodiments, the material includes polyacrylamide, poly-ethylene glycol (PEG), poly(acrylate-co-acrylic acid) (PAA), or Poly(N-isopropylacrylamide) (NIPAM).

In embodiments the cell is lysed to release nucleic acid or other materials from the cells. For example, the cells may be lysed using reagents (e.g., a surfactant such as Triton-X or SDS, an enzyme such as lysozyme, lysostaphin, zymolase, cellulase, mutanolysin, glycanases, proteases, mannase, proteinase K, etc.) or a physical lysing mechanism a physical condition (e.g., ultrasound, ultraviolet light, mechanical agitation, etc.). The cells may release, for instance, DNA, RNA, mRNA, proteins, or enzymes. The cells may arise from any suitable source. For instance, the cells may be any cells for which nucleic acid from the cells is desired to be studied or sequenced, etc., and may include one, or more than one, cell type. The cells may be for example, from a specific population of cells, such as from a certain organ or tissue (e.g., cardiac cells, immune cells, muscle cells, cancer cells, etc.), cells from a specific individual or species (e.g., human cells, mouse cells, bacteria, etc.), cells from different organisms, cells from a naturally-occurring sample (e.g., pond water, soil, etc.), or the like. In some cases, the cells may be dissociated from tissue. In embodiments, the method does not include lysing the cell.

In embodiments, before sequencing the barcode, the method includes subjecting the sample to expansion microscopy techniques. In embodiments, the method includes further including subjecting the sample to expansion microscopy after step i). Expansion microscopy techniques allows individual targets (e.g., mRNA, proteins, or RNA transcripts) which are densely packed within a cell, to be resolved spatially in a high-throughput manner. Expansion microscopy techniques are known in the art and can be performed as described in US 2016/0116384 and Chen et al., Science, 347, 543 (2015), each of which are incorporated herein by reference in their entirety.

In embodiments, the method does not include subjecting the cell to expansion microscopy. Typically, expansion microscopy techniques utilize a swellable polymer or hydrogel (e.g., a synthetic matrix-forming material) which can significantly slow diffusion of enzymes and nucleotides. Matrix (e.g., synthetic matrix) forming materials include polyacrylamide, cellulose, alginate, polyamide, cross-linked agarose, cross-linked dextran or cross-linked polyethylene glycol. The matrix forming materials can form a matrix by polymerization and/or crosslinking of the matrix forming materials using methods specific for the matrix forming materials and methods, reagents and conditions known to those of skill in the art. Additionally, expansion microscopy techniques may render the temperature of the cell sample difficult to modulate in a uniform, controlled manner. Modulating temperature provides a useful parameter to optimize amplification and sequencing methods. In embodiments, the method does not include an exogenous matrix.

In embodiments, the method further includes an amplification method for amplifying the circular polynucleotide. In embodiments, the method further includes amplifying the circular polynucleotide by extending an amplification primer with a polymerase (e.g., a strand-displacing polymerase), wherein the primer extension generates an extension product including multiple complements of the circular polynucleotide, which may be referred to as an amplicon. In embodiments, amplifying includes incubation with a strand-displacing polymerase for about 10 seconds to about 60 minutes. In embodiments, amplifying includes incubation with a strand-displacing polymerase for about 60 seconds to about 60 minutes. In embodiments, amplifying includes incubation with a strand-displacing polymerase for about 10 minutes to about 60 minutes. In embodiments, amplifying includes incubation with a strand-displacing polymerase for about 10 minutes to about 30 minutes. In embodiments, amplifying includes incubation with a strand-displacing polymerase at a temperature of about 20° C. to about 50° C. In embodiments, incubation with the strand-displacing polymerase is at a temperature of about 35° C. to 42° C. In embodiments, the strand-displacing polymerase is phi29 polymerase, SD polymerase, Bst large fragment polymerase, phi29 mutant polymerase, or a thermostable phi29 mutant polymerase. An amplicon typically contains multiple, tandem copies of the circularized nucleic acid molecule of the corresponding sample nucleic acid. The number of copies can be varied by appropriate modification of the reaction conditions, such as varying the number of amplification cycles, using polymerases of varying processivity in the amplification reaction, or varying the length of time that the amplification reaction is run. In embodiments, the circular polynucleotide is copied about 5-50 times (i.e., the extension product includes about 5 to 50 complements of the circular polynucleotide). In embodiments, the circular polynucleotide is copied about 100-300 times (i.e., the extension product includes about 100 to 300 complements of the circular polynucleotide). In embodiments, the method includes hybridizing an amplification primer and padlock probe in the same reaction (e.g., simultaneously). In embodiments, the method includes contacting the target with an amplification primer and padlock probe in the same reaction (e.g., simultaneously).

In embodiments, the method includes contacting the cell with a polymer including a plurality of immobilized oligonucleotide primers (e.g., primers covalently attached to components within the matrix forming polymer). In embodiments, the method includes contacting the cell with crosslinking agents (e.g., NHS-PEG-azide), wherein the crosslinking agents contact bioconjugate reactive moieties present in the cell (e.g., amine moieties), following by contacting the cell with a plurality of oligonucleotide primers, wherein the 5' end of the primers include a bioconjugate reactive moiety (e.g., DBCO) capable of interacting with the crosslinking agent. A crosslinking agent is a compound that includes two or more orthogonal bioconjugate reactive moieties capable of participating in a reaction to form a bioconjugate linker (e.g., covalent linker). In embodiments, the method includes contacting the cell with a plurality of oligonucleotide primers that are capable of forming a covalent attachment to one or more cellular components; when the oligonucleotide primers form a covalent attachment to a cellular component, they may be referred to as immobilized oligonucleotide primers. In embodiments, the covalent attachment of the oligonucleotide primers to one or more cellular components does not require cross-linking. In embodiments, the attachment of the oligonucleotide primers to one or more cellular components includes hybridization of modified oligonucleotides (e.g., LNA-containing oligonucleotides that provide increased thermal hybridization stability). Non-limiting examples of covalent attachment include amine-modified polynucleotides within the primer reacting with epoxy or isothiocyanate groups within the matrix, succinylated polynucleotides within the primer reacting with aminophenyl or aminopropyl functional groups within the matrix, dibenzocyclooctyne (DBCO)-modified polynucleotides within the primer reacting with azide functional groups within the matrix (or vice versa), trans-cyclooctyne-modified polynucleotides within the primer reacting with tetrazine or methyl tetrazine groups within the matrix (or vice versa), disulfide modified polynucleotides within the primer reacting with mercapto-functional groups within the matrix, amine-functionalized polynucleotides within the primer reacting with carboxylic acid groups within the matrix or cellular component via 1-ethyl-3-(3-dimethylaminopropyl)-carbodiimide hydrochloride (EDC) chemistry, thiol-modified polynucleotides within the primer attaching to the matrix or cellular component via a disulfide bond or maleimide linkage, alkyne-modified polynucleotides within the primer attaching to a matrix via copper-catalyzed click reactions to azide functional groups within the matrix, azide-modified polynucleotides within the primer attaching to the matrix via copper-catalyzed click reactions to alkyne functional groups within the matrix, and acrydite-modified polynucleotides within the primer polymerizing with free acrylic acid monomers within the matrix to form polyacrylamide. In embodiments, the primer is attached to the matrix through electrostatic binding. For example, the negatively charged phosphate backbone of the primer may be bound electrostatically to positively charged monomers in the matrix.

In embodiments, the plurality of oligonucleotide primers form covalent attachments (i.e., bioconjugate linkers) to one or more cellular components and/or crosslinking agents through bioconjugate reactive moieties. In embodiments, the 5' end of the primer contains a functional group that is capable of reacting with a complementary group so the primer may be tethered to a cellular component (e.g., a protein). In embodiments, the primers may be used to aid in tethering the extension product to a confined area and may not be extended. In embodiments, the immobilized oligonucleotides include blocking groups at their 3' ends that prevent polymerase extension. A blocking moiety prevents formation of a covalent bond between the 3' hydroxyl moiety of the nucleotide and the 5' phosphate of another nucleotide. In embodiments, the method includes extending the one or more immobilized oligonucleotides hybridized to an extension product with a polymerase. For example, the one or more immobilized oligonucleotides may be used to aid in tethering the extension product to a localized area and may be extended in an exponential RCA amplification reaction. In embodiments, the 5' end of the primer is covalently attached to a cellular component. In embodiments, the 5' end of the primer is covalently attached to the matrix. In embodiments, the 3' end of the primer is covalently attached to a cellular component. In embodiments, the 3' end of the primer is covalently attached to the matrix. The primers can include one or more reactive moieties. As used herein, the term reactive moiety includes any group capable of reacting with another molecule, e.g., a nucleic acid or polypeptide through covalent, non-covalent or other interactions. By way of example, the primer can include an amino acid reactive moiety that reacts with an amino acid on a protein or polypeptide through a covalent, non-covalent or other interaction.

In embodiments, the method includes contacting the cell with a plurality of specific binding reagents (e.g., antibodies), wherein each of the specific binding reagent includes an oligonucleotide primer. In embodiments, the oligonucleotide primer may be used to aid in tethering the extension product to a confined area and may not be extended. In embodiments, the oligonucleotide primer includes a blocking group at the 3' end that prevents polymerase extension. In embodiments, the method includes extending the one or more oligonucleotide primers hybridized to an extension product with a polymerase. For example, the one or more oligonucleotide primers attached to the specific binding reagent (e.g., an antibody) may be used to aid in tethering the extension product to a localized area and may be extended in an exponential RCA amplification reaction. In embodiments, the 5' end of the primer is attached to the specific binding reagent.

In embodiments, the amplifying includes rolling circle amplification (RCA) or rolling circle transcription (RCT) (see, e.g., Lizardi et al., Nat. Genet. 19:225-232 (1998), which is incorporated herein by reference in its entirety). Several suitable rolling circle amplification methods are known in the art. For example, RCA amplifies a circular polynucleotide (e.g., DNA) by polymerase extension of an amplification primer complementary to a portion of the template polynucleotide. This process generates copies of the circular polynucleotide template such that multiple complements of the template sequence arranged end to end in tandem are generated (i.e., a concatemer) locally preserved at the site of the circle formation. In embodiments, the amplifying occurs at isothermal conditions. In embodiments, the amplifying includes hybridization chain reaction (HCR). HCR uses a pair of complementary, kinetically trapped hairpin oligomers to propagate a chain reaction of hybridization events, as described in Dirks, R. M., & Pierce, N. A. (2004) PNAS USA, 101(43), 15275-15278, which is incorporated herein by reference for all purposes. In embodiments, the amplifying includes branched rolling circle amplification (BRCA); e.g., as described in Fan T, Mao Y, Sun Q, et al. Cancer Sci. 2018; 109:2897-2906, which is incorporated herein by reference in its entirety. In embodiments, the amplifying includes hyperbranched rolling circle amplification (HRCA). Hyperbranched RCA uses a second primer complementary to the first amplification product. This allows products to be replicated by a strand-displacement mechanism, which yields drastic amplification within an isothermal reaction (Lage et al., Genome Research 13:294-307 (2003), which is incorporated herein by reference in its entirety). In embodiments, amplifying includes polymerase extension of an amplification primer. In embodiments, the polymerase is T4, T7, Sequenase, Taq, Klenow, Tth polymerase, or a Pol I DNA polymerase. SD polymerase, Bst large fragment polymerase, or a phi29 polymerase or mutant thereof. In embodiments, the strand-displacing enzyme is an SD polymerase, Bst large fragment polymerase, or a phi29 polymerase or mutant thereof. In embodiments, the strand-displacing polymerase is phi29 polymerase, phi29 mutant polymerase or a thermostable phi29 mutant polymerase. A "phi polymerase" (or "(129 polymerase") is a DNA polymerase from the (D29 phage or from one of the related phages that, like (129, contain a terminal protein used in the initiation of DNA replication. For example, phi29 polymerases include the B103, GA-1, PZA, (D15, BS32, M2Y (also known as M2), Nf, G1, Cp-1, PRD1, PZE, SFS, Cp-5, Cp-7, PR4, PR5, PR722, L17, (D21, and AV-1 DNA polymerases, as well as chimeras thereof. A phi29 mutant DNA polymerase includes one or more mutations relative to naturally-occurring wild-type phi29 DNA polymerases, for example, one or more mutations that alter interaction with and/or incorporation of nucleotide analogs, increase stability, increase read length, enhance accuracy, increase photo tolerance, and/or alter another polymerase property, and can include additional alterations or modifications over the wild-type phi29 DNA polymerase, such as one or more deletions, insertions, and/or fusions of additional peptide or protein sequences. Thermostable phi29 mutant polymerases are known in the art, see for example US 2014/0322759, which is incorporated herein by reference for all purposes. For example, a thermostable phi29 mutant polymerase refers to an isolated bacteriophage phi29 DNA polymerase including at least one mutation selected from the group consisting of M8R, V51A, M97T, L123S, G197D, K209E, E221K, E239G, Q497P, K512E, E515A, and F526 (relative to wild type phi29 polymerase). In embodiments, the polymerase is a phage or bacterial RNA polymerases (RNAPs). In embodiments, the polymerase is a T7 RNA polymerase. In embodiments, the polymerase is an RNA polymerase. Useful RNA polymerases include, but are not limited to, viral RNA polymerases such as T7 RNA polymerase, T3 polymerase, SP6 polymerase, and Kll polymerase; Eukaryotic RNA polymerases such as RNA polymerase I, RNA polymerase II, RNA polymerase III, RNA polymerase IV, and RNA polymerase V; and Archaea RNA polymerase.

In embodiments, the amplification method includes a standard dNTP mixture including dATP, dCTP, dGTP and dTTP (for DNA) or dATP, dCTP, dGTP and dUTP (for RNA). In embodiments, the amplification method includes a mixture of standard dNTPs and modified nucleotides that contain functional moieties (e.g., bioconjugate reactive groups) that serve as attachment points to the matrix in which the cell is embedded (e.g. a hydrogel). In embodiments, the amplification method includes a mixture of standard dNTPs and modified nucleotides that contain functional moieties (e.g., bioconjugate reactive groups) that participate in the formation of a bioconjugate linker. The modified nucleotides may react and link the amplification product to the surrounding cell scaffold. For example, amplifying may include an extension reaction wherein the polymerase incorporates a modified nucleotide into the amplification product, wherein the modified nucleotide includes a bioconjugate reactive moiety (e.g., an alkynyl moiety) attached to the nucleobase. The bioconjugate reactive moiety of the modified nucleotide participates in the formation of a bioconjugate linker by reacting with a complementary bioconjugate reactive moiety present in the cell (e.g., a crosslinking agent, such as NHS-PEG-azide, or an amine moiety) thereby attaching the amplification product to the internal scaffold of the cell. In embodiments, the functional moiety can be covalently cross-linked, copolymerize with or otherwise non-covalently bound to the matrix. In embodiments, the functional moiety can react with a cross-linker. In embodiments, the functional moiety can be part of a ligand-ligand binding pair. Suitable exemplary functional moieties include an amine, acrydite, alkyne, biotin, azide, and thiol. In embodiments of crosslinking, the functional moiety is cross-linked to modified dNTP or dUTP or both. In embodiments, suitable exemplary cross-linker reactive groups include imidoester (DMP), succinimide ester (NHS), maleimide (Sulfo-SMCC), carbodiimide (DCC, EDC) and phenyl azide. Cross-linkers within the scope of the present disclosure may include a spacer moiety. In embodiments, such spacer moieties may be functionalized. In embodiments, such spacer moieties may be chemically stable. In embodiments, such spacer moieties may be of sufficient length to allow amplification of the nucleic acid bound to the matrix. In embodiments, suitable exemplary spacer moieties include polyethylene glycol, carbon spacers, photo-cleavable spacers and other spacers known to those of skill in the art and the like. In embodiments, amplification reactions include standard dNTPs and a modified nucleotide (e.g., amino-allyl dUTP, 5-TCO-PEG4-dUTP, C8-Alkyne-dUTP, 5-Azidomethyl-dUTP, 5-Vinyl-dUTP, or 5-Ethynyl dLTTP). For example, during amplification a mixture of standard dNTPs and aminoallyl deoxyuridine 5'-triphosphate (dUTP) nucleotides may be incorporated into the amplicon and subsequently cross-linked to the cell protein matrix by using a cross-linking reagent (e.g., an amine-reactive crosslinking agent with PEG spacers, such as (PEGylated bis(sulfosuccinimidyl)suberate) (BS(PEG)9)).

In embodiments, the amplification primer and the sequencing primer includes an oligonucleotide, either natural or synthetic, that is capable, upon forming a duplex with a polynucleotide template, of acting as a point of initiation of nucleic acid synthesis and being extended from its 3' end along the template so that an extended duplex is formed. The sequence of nucleotides added during the extension process is determined by the sequence of the template polynucleotide. Primers (e.g., amplification primer or sequencing primer) include nucleotides ranging from 17 to 30 nucleotides. In embodiments, the primer is at least 17 nucleotides, or alternatively, at least 18 nucleotides, or alternatively, at least 19 nucleotides, or alternatively, at least 20 nucleotides, or alternatively, at least 21 nucleotides, or alternatively, at least 22 nucleotides, or alternatively, at least 23 nucleotides, or alternatively, at least 24 nucleotides, or alternatively, at least 25 nucleotides, or alternatively, at least 26 nucleotides, or alternatively, at least 27 nucleotides, or alternatively, at least 28 nucleotides, or alternatively, at least 29 nucleotides, or alternatively, at least 30 nucleotides, or alternatively at least 50 nucleotides, or alternatively at least 75 nucleotides or alternatively at least 100 nucleotides.

In embodiments, one or more nucleotides within the amplification primer sequence, the sequencing primer sequence, and/or the immobilized oligonucleotide primer contains one or more functional moieties (e.g., bioconjugate reactive groups) that serve as attachment points to the matrix in which the cell is embedded (e.g. a hydrogel) or to the internal cellular scaffold. In embodiments, one or more nucleotides within the amplification primer sequence, the sequencing primer sequence, and/or the immobilized oligonucleotide primer contains one or more functional moieties (e.g., bioconjugate reactive groups) that serve as attachment points to complementary bioconjugate reactive groups within the cell (e.g., a protein). In embodiments, a plurality of oligonucleotide primers are provided to the matrix in which the cell is embedded prior to amplification. In embodiments, a plurality of oligonucleotide primers are provided to the matrix in which the cell is embedded concurrently with amplification. In embodiments, the bioconjugate reactive group is located at the 5' or 3' end of the primer. In embodiments, the bioconjugate reactive group is located at an internal position of the primer e.g., the primer contains one or more modified nucleotides, such as aminoallyl deoxyuridine 5'-triphosphate (dUTP) nucleotide(s). In embodiments, the functional moiety can be covalently cross-linked, copolymerize with or otherwise non-covalently bound to the matrix. In embodiments, the functional moiety can react with a cross-linker. In embodiments, the functional moiety can be part of a ligand-ligand binding pair. Suitable exemplary functional moieties include an amine, acrydite, alkyne, biotin, azide, and thiol. In embodiments of crosslinking, the functional moiety is cross-linked to modified dNTP or dUTP or both. In embodiments, suitable exemplary cross-linker reactive groups include imidoester (DMP), succinimide ester (NHS), maleimide (Sulfo-SMCC), carbodiimide (DCC, EDC) and phenyl azide. Cross-linkers within the scope of the present disclosure may include a spacer moiety. In embodiments, such spacer moieties may be functionalized. In embodiments, such spacer moieties may be chemically stable. In embodiments, such spacer moieties may be of sufficient length to allow amplification of the nucleic acid bound to the matrix. In embodiments, suitable exemplary spacer moieties include polyethylene glycol, carbon spacers, photo-cleavable spacers and other spacers known to those of skill in the art and the like. In embodiments, the amplification primer and/or the sequencing primer contains a modified nucleotide (e.g., amino-allyl dUTP, 5-TCO-PEG4-dUTP, C8-Alkyne-dUTP, 5-Azidomethyl-dUTP, 5-Vinyl-dUTP, or 5-Ethynyl dLTTP). For example, prior to amplification, the modified nucleotide-containing primer is attached to the cell protein matrix by using a cross-linking reagent (e.g., an amine-reactive cross-linking agent with PEG spacers, such as (PEGylated bis (sulfosuccinimidyl)suberate) (BS(PEG)9)).

In embodiments, the primer oligonucleotide is covalently attached to the matrix or to a cellular component via a bioconjugate reactive linker. In embodiments, the 5' end of the primer contains a functional group that is capable of reacting with a complementary group so the primer may be tethered to a cellular component (e.g., a protein). Non-limiting examples of covalent attachment include amine-modified polynucleotides within the primer reacting with epoxy or isothiocyanate groups within the matrix, succinylated polynucleotides within the primer reacting with aminophenyl or aminopropyl functional groups within the matrix, dibenzocyclooctyne-modified polynucleotides within the primer reacting with azide functional groups within the matrix (or vice versa), trans-cyclooctyne-modified polynucleotides within the primer reacting with tetrazine or methyl tetrazine groups within the matrix (or vice versa), disulfide modified polynucleotides within the primer reacting with mercapto-functional groups within the matrix, amine-functionalized polynucleotides within the primer reacting with carboxylic acid groups within the matrix or cellular component via 1-ethyl-3-(3-dimethylaminopropyl)-carbodiimide hydrochloride (EDC) chemistry, thiol-modified polynucleotides within the primer attaching to the matrix or cellular component via a disulfide bond or maleimide linkage, alkyne-modified polynucleotides within the primer attaching to a matrix via copper-catalyzed click reactions to azide functional groups within the matrix, azide-modified polynucleotides within the primer attaching to the matrix via copper-catalyzed click reactions to alkyne functional groups within the matrix, and acrydite-modified polynucleotides within the primer polymerizing with free acrylic acid monomers within the matrix to form polyacrylamide. In embodiments, the primer is attached to the matrix through electrostatic binding. For example, the negatively charged phosphate backbone of the primer may be bound electrostatically to positively charged monomers in the solid support.

In embodiments, the primer includes a first bioconjugate reactive group. In embodiments, the primer is attached to a cellular compartment. In embodiments, the cellular component includes a second bioconjugate reactive group. In embodiments, the first bioconjugate reactive group is attached to the second bioconjugate reactive group by covalent or non-covalent bonding. In embodiments, the primer is covalently attached to a cellular component. In embodiments, the 5' end of the primer contains a functional group that is tethered to the cellular component. In embodiments, the primer is covalently attached to a matrix within the cell. In embodiments, the 5' end of the primer contains a functional group that is tethered to the matrix within the cell. Non-limiting examples of covalent attachment include amine-modified polynucleotides reacting with epoxy or isothiocyanate groups in the cell or matrix within the cell, succinylated polynucleotides reacting with aminophenyl or aminopropyl functional groups in the cell or matrix within the cell, dibenzocyclooctyne-modified polynucleotides reacting with azide functional groups in the cell or matrix within the cell (or vice versa), trans-cyclooctyne-modified polynucleotides reacting with tetrazine or methyl tetrazine groups in the cell or matrix within the cell (or vice versa), disulfide modified polynucleotides reacting with mercapto-functional groups in the cell or matrix within the cell, amine-functionalized polynucleotides reacting with carboxylic acid groups in the cell or matrix within the cell via 1-ethyl-3-(3-dimethylaminopropyl)-carbodiimide hydrochloride (EDC) chemistry, thiol-modified polynucleotides attaching to cell or matrix within the cell via a disulphide bond or maleimide linkage, alkyne-modified polynucleotides attaching to the cell or matrix within the cell via copper-catalyzed click reactions to azide functional groups in the cell or matrix within the cell, and acrydite-modified polynucleotides polymerizing with free acrylic acid monomers in the cell or matrix within the cell to form polyacrylamide or reacting with thiol groups in the cell or matrix within the cell. In embodiments, the primer is attached to the polymer through electrostatic binding. For example, the negatively charged phosphate backbone of the primer may be bound electrostatically to positively charged monomers in the matrix.

In embodiments, the primer oligonucleotide is attached to the matrix or to a cellular component via a specific binding reagent. In embodiments, the specific binding reagent includes an antibody, single-chain Fv fragment (scFv), antibody fragment-antigen binding (Fab), or an aptamer. In embodiments, the specific binding reagent includes an antibody, or antigen binding fragment, an aptamer, affimer, or non-immunoglobulin scaffold. In embodiments, the specific binding reagent is a peptide, a cell penetrating peptide, an aptamer, a DNA aptamer, an RNA aptamer, an antibody, an antibody fragment, a light chain antibody fragment, a single-chain variable fragment (scFv), a lipid, a lipid derivative, a phospholipid, a fatty acid, a triglyceride, a glycerolipid, a glycerophospholipid, a sphingolipid, a saccharolipid, a polyketide, a polylysine, polyethyleneimine, diethylaminoethyl (DEAE)-dextran, cholesterol, or a sterol moiety. For example, the matrix or cellular component (e.g., a protein) may contain a complementary specific binding reagent to the primer containing a specific binding reagent.

In embodiments, the method includes amplifying the circular polynucleotide by extending an amplification primer with a strand-displacing polymerase, wherein the primer extension generates an extension product including multiple complements of the circular polynucleotide. In embodiments, the method of amplifying includes an isothermal amplification method. In embodiments, the method of amplifying includes rolling circle amplification (RCA) or rolling circle transcription (RCT). In embodiments, the method of amplifying is rolling circle amplification (RCA). In embodiments, amplifying includes exponential rolling circle amplification (eRCA). Exponential RCA is similar to the linear process except that it uses a second primer (e.g., one or more immobilized oligonucleotide(s)) having a sequence that is identical to at least a portion of the circular template (Lizardi et al. Nat. Genet. 19:225 (1998)). This two-primer system achieves isothermal, exponential amplification. Exponential RCA has been applied to the amplification of non-circular DNA through the use of a linear probe that binds at both of its ends to contiguous regions of a target DNA followed by circularization using DNA ligase (Nilsson et al. Science 265(5181):208 5 (1994)).

In embodiments, the method does not include ligation or amplification. For example, the method includes hybridizing a probe nucleic acid to the target (i.e., to a complementary region or gene of interest), wherein the probe nucleic acid is branched DNA or a concatemer and comprises at least one sequencing primer binding sequence and a plurality of oligonucleotide barcodes. In embodiments, the probe nucleic acid comprises a plurality of identical barcodes. In embodiments, associating an oligonucleotide barcode with each of the plurality of targets includes hybridizing a probe nucleic acid, wherein the probe nucleic acid includes branched DNA or a concatemer and includes at least one sequencing primer binding sequence and a plurality of oligonucleotide barcodes. In embodiments, the probe nucleic acid includes a plurality of identical oligonucleotide barcodes. In embodiments, the probe nucleic acid includes two or more complementary sequences to the target. In embodiments, the probe nucleic acid includes two or more different oligonucleotide barcodes.

In embodiments, the probe nucleic acid comprises a two or more complementary sequences to the target. In embodiments, the probe nucleic acid comprises two or more different oligonucleotide barcodes. In embodiments, the probe includes a primer binding sequence from a known set of primer binding sequences. In embodiments, the probe includes a sequencing primer binding sequence from a known set of sequencing primer binding sequences.

In embodiments, the method further includes proximity ligation techniques known in the art; see for example the methods, complexes, and kits described in US 2002/0064779, US 2005/0287526, and US 2014/0170654, each of which are incorporated herein by reference. With these methods, an amplified product is produced only if two specific antibodies bind to the same protein (or within approximately 5 nm from each other). One antibody provides the DNA oligonucleotide barcode that acts as a splint for a padlock probe, while the other antibody carries the primer for RCA. Thus, RCA amplification reaction only occurs if both antibodies bind to their respective epitopes on the target protein (or protein complex). Thus, in an aspect is provided a method of detecting a plurality of targets including different proteins within an optically resolved volume of a cell in situ; the method including: i) associating a different oligonucleotide barcode from a known set of barcodes with each of the plurality of targets, wherein associating an oligonucleotide barcode with each of the plurality of targets comprises contacting each of the targets with a specific binding reagent, wherein the specific binding reagent comprises an oligonucleotide barcode, and contacting each of the targets with a specific binding reagent, wherein the specific binding reagent comprises an oligonucleotide primer sequence from a known set of primer sequences; ii) hybridizing a padlock probe to two adjacent nucleic acid sequences of the barcode, wherein the padlock probe is a single-stranded polynucleotide having a 5' and a 3' end; iii) sequencing each barcode to obtain a multiplexed signal in the cell in situ; iv) demultiplexing the multiplexed signal by comparison with the known set of barcodes; and v) detecting the plurality of targets by identifying the associated barcodes detected in the cell.

In embodiments, the method includes sequencing the barcode. In embodiments, the method includes sequencing a plurality of barcodes in an optically resolved volume. A variety of sequencing methodologies can be used such as sequencing-by synthesis (SBS), pyrosequencing, sequencing by ligation (SBL), or sequencing by hybridization (SBH). Pyrosequencing detects the release of inorganic pyrophosphate (PPi) as particular nucleotides are incorporated into a nascent nucleic acid strand (Ronaghi, et al., Analytical Biochemistry 242(1), 84-9 (1996); Ronaghi, Genome Res. 11(1), 3-11 (2001); Ronaghi et al. Science 281(5375), 363 (1998); U.S. Pat. Nos. 6,210,891; 6,258,568; and. 6,274,320, each of which is incorporated herein by reference in its entirety). In pyrosequencing, released PPi can be detected by being converted to adenosine triphosphate (ATP) by ATP sulfurylase, and the level of ATP generated can be detected via light produced by luciferase. In this manner, the sequencing reaction can be monitored via a luminescence detection system. In both SBL and SBH methods, target nucleic acids, and amplicons thereof, are subjected to repeated cycles of oligonucleotide delivery and detection. SBL methods, include those described in Shendure et al. Science 309:1728-1732 (2005); U.S. Pat. Nos. 5,599,675; and 5,750,341, each of which is incorporated herein by reference in its entirety; and the SBH methodologies are as described in Bains et al., Journal of Theoretical Biology 135(3), 303-7 (1988); Drmanac et al., Nature Biotechnology 16, 54-58 (1998); Fodor et al., Science 251 (4995), 767-773 (1995); and WO 1989/10977, each of which is incorporated herein by reference in its entirety.

In SBS, extension of a nucleic acid primer along a nucleic acid template is monitored to determine the sequence of nucleotides in the template. The underlying chemical process can be catalyzed by a polymerase, wherein fluorescently labeled nucleotides are added to a primer (thereby extending the primer) in a template dependent fashion such that detection of the order and type of nucleotides added to the primer can be used to determine the sequence of the template. In embodiments, sequencing includes annealing and extending a sequencing primer to incorporate a detectable label that indicates the identity of a nucleotide in the target polynucleotide, detecting the detectable label, and repeating the extending and detecting of steps. In embodiments, the methods include sequencing one or more bases of a target nucleic acid by extending a sequencing primer hybridized to a target nucleic acid (e.g., an amplification product produced by the amplification methods described herein). In embodiments, sequencing may be accomplished by a sequencing-by-synthesis (SBS) process. In embodiments, sequencing comprises a sequencing by synthesis process, where individual nucleotides are identified iteratively, as they are polymerized to form a growing complementary strand. In embodiments, nucleotides added to a growing complementary strand include both a label and a reversible chain terminator that prevents further extension, such that the nucleotide may be identified by the label before removing the terminator to add and identify a further nucleotide. Such reversible chain terminators include removable 3' blocking groups, for example as described in U.S. Pat. Nos. 7,541,444 and 7,057,026. Once such a modified nucleotide has been incorporated into the growing polynucleotide chain complementary to the region of the template being sequenced, there is no free 3'—OH group available to direct further sequence extension and therefore the polymerase cannot add further nucleotides. Once the identity of the base incorporated into the growing chain has been determined, the 3' reversible terminator may be removed to allow addition of the next successive nucleotide. By ordering the products derived using these modified nucleotides it is possible to deduce the DNA sequence of the oligonucleotide barcode.

In embodiments, sequencing includes extending a sequencing primer to generate a sequencing read comprising the barcode sequence. In embodiments, sequencing includes extending a sequencing primer by incorporating a labeled nucleotide, or labeled nucleotide analogue and detecting the label to generate a signal for each incorporated nucleotide or nucleotide analogue. In embodiments, the labeled nucleotide or labeled nucleotide analogue further comprises a reversible terminator moiety.

In embodiments, sequencing includes extending a first sequencing primer to generate a sequencing read comprising the first barcode sequence, or a portion thereof. In embodiments, sequencing includes extending a first sequencing primer to generate a sequencing read comprising the first barcode sequence, or a portion thereof, and extending a second sequencing primer to generate a sequencing read comprising the second barcode sequence. In embodiments, sequencing includes sequentially extending a plurality of sequencing primers (e.g., sequencing a first barcode followed by sequencing a second barcode, followed by sequencing N barcodes, where N is the number of sequencing primers in the known sequencing primer set). In embodiments, sequencing includes generating a plurality of sequencing reads.

In embodiments, the methods of sequencing a nucleic acid include a extending a polynucleotide by using a polymerase. In embodiments, the polymerase is a DNA polymerase. In embodiments, the DNA polymerase is a Pol I DNA polymerase, Pol II DNA polymerase, Pol III DNA polymerase, Pol IV DNA polymerase, Pol V DNA polymerase, Pol β DNA polymerase, Pol μ DNA polymerase, Pol λ DNA polymerase, Pol σ DNA polymerase, Pol α DNA polymerase, Pol δ DNA polymerase, Pol ε DNA polymerase, Pol η DNA polymerase, Pol τ DNA polymerase, Pol κ DNA polymerase, Pol ζ DNA polymerase, Pol γ DNA polymerase, Pol θ DNA polymerase, Pol υ DNA polymerase, or a thermophilic nucleic acid polymerase (e.g., Therminator γ, 9° N polymerase (exo-), Therminator II, Therminator III, or Therminator IX). In embodiments, the DNA polymerase is a thermophilic nucleic acid polymerase. In embodiments, the DNA polymerase is a modified archaeal DNA polymerase. In embodiments, the polymerase is a mutant *P. abyssi* polymerase (e.g., such as a mutant *P. abyssi* polymerase described in WO 2018/148723 or WO 2020/056044, each of which are incorporated herein by reference for all purposes). In embodiments, the polymerase is a bacterial DNA polymerase, eukaryotic DNA polymerase, archaeal DNA polymerase, viral DNA polymerase, or phage DNA polymerases. Bacterial DNA polymerases include *E. coli* DNA polymerases I, II and III, IV and V, the Klenow fragment of *E. coli* DNA polymerase, *Clostridium stercorarium* (Cst) DNA polymerase, *Clostridium thermocellum* (Cth) DNA polymerase and *Sulfolobus solfataricus* (Sso) DNA polymerase. Eukaryotic DNA polymerases include DNA polymerases α, β, γ, γ, ϵ, η, ζ, λ, σ, μ, and κ, as well as the Revl polymerase (terminal deoxycytidyl transferase) and terminal deoxynucleotidyl transferase (TdT). Viral DNA polymerases include T4 DNA polymerase, phi-29 DNA polymerase, GA-1, phi-29-like DNA polymerases, PZA DNA polymerase, phi-15 DNA polymerase, Cpl DNA polymerase, Cpl DNA polymerase, T7 DNA polymerase, and T4 polymerase. Other useful DNA polymerases include thermostable and/or thermophilic DNA polymerases such as *Thermus aquaticus* (Taq) DNA polymerase, *Thermus filiformis* (Tfi) DNA polymerase, *Thermococcus* zilligi (Tzi) DNA polymerase, *Thermus thermophilus* (Tth) DNA polymerase, *Thermus flavus* (Tfl) DNA polymerase, *Pyrococcus woesei* (Pwo) DNA polymerase, *Pyrococcus furiosus* (Pfu) DNA polymerase and Turbo Pfu DNA polymerase, *Thermococcus litoralis* (Tli) DNA polymerase, *Pyrococcus* sp. GB-D polymerase, *Thermotoga maritima* (Tma) DNA polymerase, *Bacillus stearothermophilus* (Bst) DNA polymerase, *Pyrococcus* Kodakaraensis (KOD) DNA polymerase, Pfx DNA polymerase, *Thermococcus* sp. JDF-3 (JDF-3) DNA polymerase, *Thermococcus gorgonarius* (Tgo) DNA polymerase, *Thermococcus acidophilum* DNA polymerase; *Sulfolobus acidocaldarius* DNA polymerase; *Thermococcus* sp. go N-7 DNA polymerase; *Pyrodictium occultum* DNA polymerase; *Methanococcus voltae* DNA polymerase; *Methanococcus* thermoautotrophicum DNA polymerase; *Methanococcus jannaschii* DNA polymerase; *Desulfurococcus* strain TOK DNA polymerase (D. Tok Pol); *Pyrococcus abyssi* DNA polymerase; *Pyrococcus horikoshii* DNA polymerase; *Pyrococcus islandicum* DNA polymerase; *Thermococcus fumicolans* DNA polymerase; *Aeropyrum pernix* DNA polymerase; and the heterodimeric DNA polymerase DP1/DP2. In embodiments, the polymerase is 3PDX polymerase as disclosed in U.S. Pat. No. 8,703,461, the disclosure of which is incorporated herein by reference. In embodiments, the polymerase is a reverse transcriptase. Exemplary reverse transcriptases include, but are not limited to, HIV-1 reverse transcriptase from human immunodeficiency virus type 1 (PDB 1HMV), HIV-2 reverse transcriptase from human immunodeficiency virus type 2, M-MLV reverse transcriptase from the Moloney murine leukemia virus, AMV reverse transcriptase from the avian myeloblastosis virus, and Telomerase reverse transcriptase.

In embodiments, sequencing includes a plurality of sequencing cycles. In embodiments, sequencing includes 2, 3, 4, 5, 6, 7, 8, 9, 10, 11, 12, 13, 14, or 15 sequencing cycles. In embodiments, sequencing includes at least 10, 20, 30 40, or 50 sequencing cycles. In embodiments, sequencing includes at least 10 sequencing cycles. In embodiments, sequencing includes 10 to 20 sequencing cycles. In embodiments, sequencing includes 10, 11, 12, 13, 14, or 15 sequencing cycles. In embodiments, sequencing includes (a) extending a sequencing primer by incorporating a labeled nucleotide, or labeled nucleotide analogue and (b) detecting the label to generate a signal for each incorporated nucleotide or nucleotide analogue.

In embodiments, the labeled nucleotide or labeled nucleotide analogue further includes a reversible terminator moiety. In embodiments, the reversible terminator moiety is attached to the 3' oxygen of the nucleotide and is independently

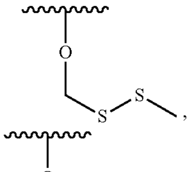, 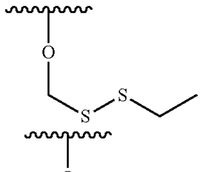,

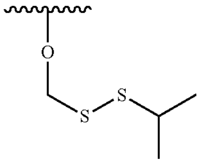, 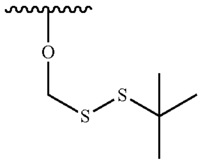,

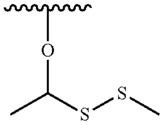, 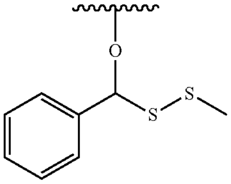,

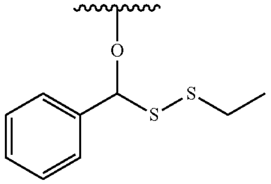, 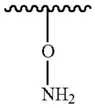,

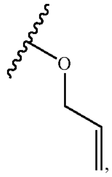, 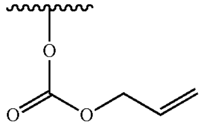, 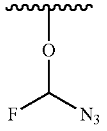,

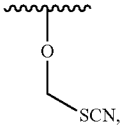, 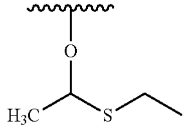,

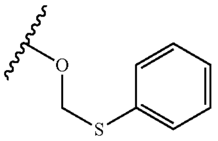, 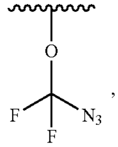,

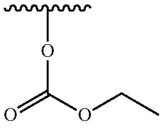, 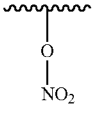, 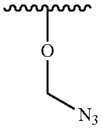, or

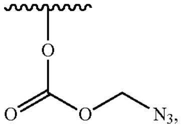, wherein the 3' oxygen is explicitly depicted in the above formulae. Additional examples of reversible terminators may be found in U.S. Pat. No. 6,664,079, Ju J. et al. (2006) *Proc Natl Acad Sci USA* 103(52):19635-19640; Ruparel H.

et al. (2005) *Proc Natl Acad Sci USA* 102(17):5932-5937; Wu J. et al. (2007) *Proc Natl Acad Sci USA* 104(104):16462-16467; Guo J. et al. (2008) *Proc Natl Acad Sci USA* 105(27): 9145-9150 Bentley D. R. et al. (2008) *Nature* 456(7218): 53-59; or Hutter D. et al. (2010) *Nucleosides Nucleotides & Nucleic Acids* 29:879-895, which are incorporated herein by reference in their entirety for all purposes. In embodiments, a polymerase-compatible cleavable moiety includes an azido moiety or a dithiol moiety.

In embodiments, detecting includes two-dimensional (2D) or three-dimensional (3D) fluorescent microscopy. Suitable imaging technologies are known in the art, as exemplified by Larsson et al., Nat. Methods (2010) 7:395-397 and associated supplemental materials, the entire content of which is incorporated by reference herein in its entirety. In embodiments of the methods provided herein, the imaging is accomplished by confocal microscopy. Confocal fluorescence microscopy involves scanning a focused laser beam across the sample and imaging the emission from the focal point through an appropriately-sized pinhole. This suppresses the unwanted fluorescence from sections at other depths in the sample. In embodiments, the imaging is accomplished by multi-photon microscopy (e.g., two-photon excited fluorescence or two-photon-pumped microscopy). Unlike conventional single-photon emission, multi-photon microscopy can utilize much longer excitation wavelength up to the red or near-infrared spectral region. This lower energy excitation requirement enables the implementation of semiconductor diode lasers as pump sources to significantly enhance the photostability of materials. Scanning a single focal point across the field of view is likely to be too slow for many sequencing applications. To speed up the image acquisition, an array of multiple focal points can be used. The emission from each of these focal points can be imaged onto a detector, and the time information from the scanning mirrors can be translated into image coordinates. Alternatively, the multiple focal points can be used just for the purpose of confining the fluorescence to a narrow axial section, and the emission can be imaged onto an imaging detector, such as a CCD, EMCCD, or s-CMOS detector. A scientific grade CMOS detector offers an optimal combination of sensitivity, readout speed, and low cost. One configuration used for confocal microscopy is spinning disk confocal microscopy. In 2-photon microscopy, the technique of using multiple focal points simultaneously to parallelize the readout has been called Multifocal Two-Photon Microscopy (MTPM). Several techniques for MTPM are available, with applications typically involving imaging in biological tissue. In embodiments of the methods provided herein, the imaging is accomplished by light sheet fluorescence microscopy (LSFM). In embodiments, detecting includes 3D structured illumination (3DSIM). In 3DSIM, patterned light is used for excitation, and fringes in the Moiré pattern generated by interference of the illumination pattern and the sample, are used to reconstruct the source of light in three dimensions. In order to illuminate the entire field, multiple spatial patterns are used to excite the same physical area, which are then digitally processed to reconstruct the final image. See York, Andrew G., et al. "Instant super-resolution imaging in live cells and embryos via analog image processing." *Nature methods* 10.11 (2013): 1122-1126 which is incorporated herein by reference. In embodiments, detecting includes selective planar illumination microscopy, light sheet microscopy, emission manipulation, pinhole confocal microscopy, aperture correlation confocal microscopy, volumetric reconstruction from slices, deconvolution microscopy, or aberration-corrected multifocus microscopy. In embodiments, detecting includes digital holographic microscopy (see for example Manoharan, V. N. Frontiers of Engineering: Reports on Leading-edge Engineering from the 2009 Symposium, 2010, 5-12, which is incorporated herein by reference). In embodiments, detecting includes confocal microscopy, light sheet microscopy, structured illumination microscopy, oblique plane microscopy, or multi-photon microscopy. Implementations of oblique plane microscopy are known, for example in Sapznik et al. eLife 2020; 9:e57681. Implementations of oblique plane microscopy are known, for example as described in Heintzmann and Huser, Chem. Rev. 2017, 117, 23, 13890-13908.

In embodiments, sequencing includes encoding the sequencing read into a codeword. Useful encoding schemes include those developed for telecommunications, coding theory and information theory such as those set forth in Hamming, *Coding and Information Theory,* $2^{nd}$ Ed. Prentice Hall, Englewood Cliffs, N.J. (1986) and Moon T K. Error Correction Coding: Mathematical Methods and Algorithms. ed. 1st Wiley: 2005, each of which are incorporated herein by reference. A useful encoding scheme uses a Hamming code. A Hamming code can provide for signal (and therefore sequencing and barcode) distinction. In this scheme, signal states detected from a series of nucleotide incorporation and detection events (i.e., while sequencing the oligonucleotide barcode) can be represented as a series of the digits to form a codeword, the codeword having a length equivalent to the number incorporation/detection events. The digits can be binary (e.g. having a value of 1 for presence of signal and a value of 0 for absence of the signal) or digits can have a higher radix (e.g., a ternary digit having a value of 1 for fluorescence at a first wavelength, a value of 2 for fluorescence at a second wavelength, and a value of 0 for no fluorescence at those wavelengths, etc.). Barcode discrimination capabilities are provided when codewords can be quantified via Hamming distances between two codewords (i.e., barcode 1 having codeword 1, and barcode 2 having codeword 2, etc.).

In embodiments, the barcodes in the known set of barcodes have a specified Hamming distance. In embodiments, the Hamming distance is 4 to 15. In embodiments, the Hamming distance is 8 to 12. In embodiments, the Hamming distance is 10. In embodiments, the Hamming distance is 0 to 100. In embodiments, the Hamming distance is 0 to 15. In embodiments, the Hamming distance is 0 to 10. In embodiments, the Hamming distance is 1 to 10. In embodiments, the Hamming distance is 5 to 10. In embodiments, the Hamming distance is 1 to 100. In embodiments, the Hamming distance between any two barcode sequences of the set is at least 2, 3, 4, or 5. In embodiments, the Hamming distance between any two barcode sequences of the set is at least 3. In embodiments, the Hamming distance between any two barcode sequences of the set is at least 4.

In embodiments, demultiplexing the multiplexed signal includes a linear decomposition of the multiplexed signal. Any of a variety of techniques may be employed for decomposition of the multiplexed signal. Examples include, but are not limited to, Zimmerman et al. Chapter 5: Clearing Up the Signal: Spectral Imaging and Linear Unmixing in Fluorescence Microscopy; Confocal Microscopy: Methods and Protocols, Methods in Molecular Biology, vol. 1075 (2014); Shirawaka H. et al.; Biophysical Journal Volume 86, Issue 3, March 2004, Pages 1739-1752; and S. Schlachter, et al, Opt. Express 17, 22747-22760 (2009); the content of each of which is incorporated herein by reference in its entirety. In embodiments, multiplexed signal includes overlap of a first signal and a second signal and is computationally resolved, for example, by imaging software.

In embodiments, the method further includes measuring an amount of one or more of the targets by counting the one or more associated barcodes. In embodiments, the method further includes counting the one or more associated barcodes in an optically resolved volume.

In embodiments, the number of unique targets detected within an optically resolved volume of a sample is about 3, 10, 30, 50, or 100. In embodiments, the number of unique targets detected within an optically resolved volume of a sample is about 1 to 10. In embodiments, the number of unique targets detected within an optically resolved volume of a sample is about 5 to 10. In embodiments, the number of unique targets detected within an optically resolved volume of a sample is about 1 to 5. In embodiments, the number of unique targets detected within an optically resolved volume of a sample is at least 3, 10, 30, 50, or 100. In embodiments, the number of unique targets detected within an optically resolved volume of a sample is less than 3, 10, 30, 50, or 100. In embodiments, the number of unique targets detected within an optically resolved volume of a sample is about 1, 2, 3, 4, 5, 6, 7, 8, 9, 10, 20, 50, 100, 500, 1,000, 5,000, 10,000, or 200,000. In embodiments, the methods allow for detection of a single target of interest. In embodiments, the methods allow for multiplex detection of a plurality of targets of interest. The use of oligonucleotide barcodes with unique identifier sequences as described herein allows for simultaneous detection of 2, 3, 4, 5, 6, 7, 8, 9, 10, 20, 30, 40, 50, 60, 70, 80, 90, 100, 200, 300, 400, 500, 600, 700, 800, 900, 1,000, 1,500, 2,000, 2,500, 3,000, 3,500, 4,000, 4,500, 5,000, 5,500, 6,000, 6,500, 7,000, 7,500, 8,000, 8,500, 9,000, 9,500, 10,000 or more than 10,000 unique targets within a single cell. In contrast to existing in situ detection methods, the methods presented herein have the advantage of virtually limitless numbers of individually detected molecules in parallel and in situ.

In embodiments, the total volume of the cell is about 1 to 25 $\mu m^3$. In embodiments, the volume of the cell is about 5 to 10 $\mu m^3$. In embodiments, the volume of the cell is about 3 to 7 $\mu m^3$.

In embodiments, the optically resolved volume has an axial resolution (i.e., depth, or z) that is greater than the lateral resolution (i.e., xy plane). In embodiments, the optically resolved volume has an axial resolution that is greater than twice the lateral resolution. In embodiments, the dimensions (i.e., the x, y, and z dimensions) of the optically resolved volume are about 0.5 μm×0.5 μm×0.5 m; 1 μm×1 μm×1 m; 2 μm×2 μm×2 m; 0.5 μm×0.5 μm×1 m; 0.5 μm×0.5 μm×2 m; 2 μm×2 μm×1 m; or 1 μm×1 μm×2 μm. In embodiments, the dimensions (i.e., the x, y, and z dimensions) of the optically resolved volume are about 1 μm×1 μm×2 m; 1 μm×1 μm×3 m; 1 μm×1 μm×4 m; or about 1 μm×1 μm×5 μm. In embodiments, the dimensions (i.e., the x, y, and z dimensions) of the optically resolved volume are about 1 μm×1 μm×5 μm. In embodiments, the dimensions (i.e., the x, y, and z dimensions) of the optically resolved volume are about 1 μm×1 μm×6 μm. In embodiments, the dimensions (i.e., the x, y, and z dimensions) of the optically resolved volume are about 1 μm×1 μm×7 μm. In embodiments, the optically resolved volume is a cubic micron. In embodiments, the optically resolved volume has a lateral resolution from about 100 to 200 nanometers, from 200 to 300 nanometers, from 300 to 400 nanometers, from 400 to 500 nanometers, from 500 to 600 nanometers, or from 600 to 1000 nanometers. In embodiments, the optically resolved volume has a axial resolution from about 100 to 200 nanometers, from 200 to 300 nanometers, from 300 to 400 nanometers, from 400 to 500 nanometers, from 500 to 600 nanometers, or from 600 to 1000 nanometers. In embodiments, the optically resolved volume has a axial resolution from about 1 to 2 μm, from 2 to 3 μm, from 3 to 4 am, from 4 to 5 am, from 5 to 6 μm, or from 6 to 10 μm.

In embodiments, the method further includes an additional imaging modality, immunofluorescence (IF), or immunohistochemistry modality (e.g., immunostaining). In embodiments, the method includes ER staining (e.g., contacting the cell with a cell-permeable dye which localizes to the endoplasmic reticula), Golgi staining (e.g., contacting the cell with a cell-permeable dye which localizes to the Golgi), F-actin staining (e.g., contacting the cell with a phalloidin-conjugated dye that binds to actin filaments), lysosomal staining (e.g., contacting the cell with a cell-permeable dye that accumulates in the lysosome via the lysosome pH gradient), mitochondrial staining (e.g., contacting the cell with a cell-permeable dye which localizes to the mitochondria), nucleolar staining, or plasma membrane staining. For example, the method includes live cell imaging (e.g., obtaining images of the cell) prior to or during fixing, immobilizing, and permeabilizing the cell. Immunohistochemistry (IHC) is a powerful technique that exploits the specific binding between an antibody and antigen to detect and localize specific antigens in cells and tissue, commonly detected and examined with the light microscope. Known IHC modalities may be used, such as the protocols described in Magaki, S., Hojat, S. A., Wei, B., So, A., & Yong, W. H. (2019). *Methods in molecular biology* (Clifton, N.J.), 1897, 289-298, which is incorporated herein by reference. In embodiments, the additional imaging modality includes bright field microscopy, phase contrast microscopy, Nomarski differential-interference-contrast microscopy, or dark field microscopy. In embodiments, the method further includes determining the cell morphology (e.g., the cell boundary or cell shape) using known methods in the art. For example, determining the cell boundary includes comparing the pixel values of an image to a single intensity threshold, which may be determined quickly using histogram-based approaches as described in Carpenter, A. et al Genome Biology 7, R100 (2006) and Arce, S., Sci Rep 3, 2266 (2013)).

In aspects and embodiments described herein, the methods are useful in the field of predictive medicine in which diagnostic assays, prognostic assays, pharmacogenomics, and monitoring clinical trials are used for prognostic (i.e., predictive) purposes to thereby treat an individual prophylactically. Accordingly, in embodiments the methods of diagnosing and/or prognosing one or more diseases and/or disorders using one or more of expression profiling methods described herein are provided.

In an aspect is provided a method of detecting a disorder (e.g., cancer) or a disease-causing mutation or allele in a cell. In embodiments, the cell includes an oncogene (e.g., HER2, BRAF, EGFR, KRAS) and utilizing the methods described herein the oncogene is identified, thereby detecting a disorder when the presence of the oncogene is identified. In embodiments, the sample includes a nucleic acid molecule which includes a disease-causing mutation or allele. In embodiments, the method includes hybridizing an oligonucleotide barcode which is correlated with the disease-causing mutation or allele. In embodiments, the method includes ligating a mutation-specific padlock probe only when the disease-causing mutation or allele is present in the nucleic acid target. In embodiments, the disease-causing mutation or allele is a base substitution, an insertion mutation, a deletion mutation, a gene amplification, a gene deletion, a gene fusion event, or a gene inversion event.

In embodiments, the mutation or allele is associated with an increased predisposition for one or more diseases, disorders, or other phenotypes. In embodiments, the mutation or allele is associated with a decreased predisposition for one or more diseases, disorders, or other phenotypes. For example, some mutations or alleles are associated with a cancer phenotype, such as decreased growth inhibition, evasion of immune detection, or dedifferentiation. Mutations that can be detected using the method provided herein include for example, mutations to BRAF, EGFR, Her2/ERBB2, and other somatic mutations as exemplified by Greenman et al., Nature (2007) 446:153-158, hereby incorporated by reference in its entirety.

In an aspect, provided herein are kits for use in accordance with any of the compounds, compositions, or methods disclosed herein, and including one or more elements thereof. In embodiments, a kit includes labeled nucleotides including differently labeled nucleotides (e.g., compounds described herein). In embodiments, the kit further includes instructions for use thereof. In embodiments, kits described herein include a polymerase. In embodiments, the polymerase is a DNA polymerase. In embodiments, the DNA polymerase is a thermophilic nucleic acid polymerase. In embodiments, the DNA polymerase is a modified archaeal DNA polymerase. In embodiments, the kit includes a sequencing solution. In embodiments, the sequencing solution include labeled nucleotides including differently labeled nucleotides, wherein the label (or lack thereof) identifies the type of nucleotide. For example, each adenine nucleotide, or analog thereof; a thymine nucleotide; a cytosine nucleotide, or analog thereof; and a guanine nucleotide, or analog thereof may be labeled with a different fluorescent label.

In an aspect is provided a method of identifying a cell that responds to a genetically modifying agent. In embodiments, the method includes administering a genetically modifying agent to the cell, detecting whether an agent-mediated nucleic acid sequence is present in the cell by detecting a plurality of different targets within an optically resolved volume of a cell in situ, according to the methods described herein, including embodiments, and identifying a cell that responds to a genetically modifying agent when the presence of the agent-mediated nucleic acid is detected in the cell. In embodiments, the method of detecting a plurality of targets within an optically resolved volume of a cell in situ includes i) associating a different oligonucleotide barcode from a known set of barcodes with each of the plurality of targets; ii) sequencing each barcode to obtain a multiplexed signal in the cell in situ; iii) demultiplexing the multiplexed signal by comparison with the known set of barcodes; and detecting the plurality of targets by identifying the associated barcodes detected in the cell.

In embodiments, the genetically modifying agent is a pathogen. In embodiments, the genetically modifying agent is a virus. In embodiments, the genetically modifying agent is a DNA virus (e.g., pox virus, herpesvirus, adenovirus, parvovirus, or warts virus). In embodiments, the genetically modifying agent is an RNA virus (e.g., influenza virus, rotavirus, mumps virus, rabies virus, eastern equine encephalitis virus, corona virus, LCM virus, polio virus, or HIV virus). In embodiments, the genetically modifying agent is a toxin. In embodiments, the genetically modifying agent is a small molecule (e.g., a pharmaceutical agent). In embodiments, the genetically modifying agent is a peptide. In embodiments, the genetically modifying agent is a prion.

In an aspect is provided a method of identifying an agent as a genetically modifying agent, the method including administering an agent to a cell, detecting whether an agent-mediated nucleic acid sequence is present in the cell by detecting a plurality of different targets within an optically resolved volume of a cell in situ, according to the methods described herein, including embodiments, and identifying the genetically modifying agent when the presence of the agent-mediated nucleic acid is detected in the cell. In embodiments, the method of detecting a plurality of targets within an optically resolved volume of a cell in situ includes i) associating a different oligonucleotide barcode from a known set of barcodes with each of the plurality of targets; ii) sequencing each barcode to obtain a multiplexed signal in the cell in situ; iii) demultiplexing the multiplexed signal by comparison with the known set of barcodes; and detecting the plurality of targets by identifying the associated barcodes detected in the cell.

In an aspect is provided a method of identifying a cell that includes a synthetic target. In embodiments, the method includes detecting whether a synthetic target is present in the cell by detecting a plurality of different targets within an optically resolved volume of a cell in situ, according to the methods described herein, including embodiments, and identifying a cell that includes a synthetic target when the presence of the synthetic target is detected in the cell. In embodiments, the method of detecting a plurality of targets within an optically resolved volume of a cell in situ includes i) associating a different oligonucleotide barcode from a known set of barcodes with each of the plurality of targets; ii) sequencing each barcode to obtain a multiplexed signal in the cell in situ; iii) demultiplexing the multiplexed signal by comparison with the known set of barcodes; and detecting the plurality of targets by identifying the associated barcodes detected in the cell.

In embodiments the synthetic target is a chimeric antigen receptor (CAR) or a gene that encodes a chimeric antigen receptor (CAR). In embodiments the synthetic target is a target introduced to the cell by genetic engineering methods (e.g., transcription activator-like effector nucleases (TALENs) or clustered regularly interspaced short palindromic repeats (CRISPR) methods).

EXAMPLES

Example 1. In Situ Transcriptomics

A wealth of information is reflected in the temporal and spatial variation of gene and protein expression among cells. Cellular macromolecules such as nucleic acids and proteins, occupy precise positions in cells and tissues, and a great deal of information is lost when these molecules are extracted. The methods available today for RNA sequence analysis (RNA-Seq) have the capacity to quantify the abundance of RNA molecules in a population of cells with great sensitivity. Current methods for single-cell RNA and protein analysis typically involve some method for "barcoding" the content of individual cells, followed by pooling the content and sequencing on a commercial DNA sequencing device (e.g., Illumina NextSeq™ 500/550, MiSeq™, HiSeq™ 2500/3000/4000, or NovaSeq™). The barcoding can be done in individual wells on a microplate (e.g., a microplate with 96, 384, or 1536 wells), and more recently droplet-based methods are emerging as an essential tool for single-cell genomics research (see for example, Klein A. and Macosko E. Lab Chip. 2017; 17(15):2540-2541; and Zheng, G. X., et al. Nature communications, 2017; 8, 14049).

Briefly, droplet-based methods begin with isolating a cell from a sample (e.g., a tissue) and encapsulating the cell in a droplet where unique identifying oligonucleotides (i.e., barcodes) are incorporated into the genomic sequence, often while converting RNAs to cDNAs during reverse transcription. These barcodes uniquely label the cDNA and identify the cellular origin. The cDNAs are then extracted and undergo standard library preparation for sequencing before being sequenced on a commercial sequencer. mRNA expression is then quantified by counting the number of barcodes that mapped to each cell.

These methods have found wide application dissecting transcriptomic heterogeneity, and can handle upwards of 10,000 cells in an automated format, however they have several limitations and drawbacks. For example, if the cells of interest originate from a tissue sample, all information about the spatial distribution of the cells within the tissue is lost in the process of dissociating and isolating the cells prior to barcoding them. Often information about the intracellular distribution of analytes within the cellular microenvironment is also lost. This information can be vital to designing therapeutic approaches to cancers, for example, where the tumor microenvironment often creates spatial gradients of nutrients and metabolic byproducts. Droplet-based techniques are capable of barcoding and sequencing tens of thousands of cells (e.g., 10-50 thousand cells) in a single experiment but current approaches require generation of custom microfluidic devices, reagents, and sample preparation techniques (e.g., as found in the disclosures RE41,780 and US 2015/0225778). Additionally, due to the digital "counting" nature of the sequencing readout, hundreds of sequencing reads/cell are required to get information about the expression of less abundant genes. For example, if a particular abundant gene is transcribed into 500 copies of RNA, the abundant gene will dominate the sequencing run resulting in relatively inefficient use of sequencing capacity. However, cells can associate with multiple barcodes which significantly impacts single-cell analyses and rare cell events (Lareau, C. A., et al. (2020) *Nature communications,* 11(1), 866).

A different barcoding approach has been applied to spatial profiling of RNA & proteins in tissue. An example of this is the method developed by Spatial Transcriptomics, a Stockholm-based company purchased by 10× Genomics in 2018 and recently commercialized as "Visium Spatial" platform. This approach involves attaching a section of a frozen tissue of interest to patterned microarrays carrying spatially barcoded oligo-dT primers that capture the entire polyadenylated transcriptome contained in the tissue section. Each spot on the microarray contains a capture probe with a spatial barcode unique to that spot allowing the individual sequencing reads to be mapped to the originating spot. After cDNA synthesis on the surface via reverse transcription, the tissue is removed and the mRNA-cDNA hybrids are released from the array to be prepared for sequencing; see Vickovic, S., et al. Nat. Methods 16, 987-990 (2019) for greater detail on the approach. The current implementation of this technology includes a microarray with 100 m spots spaced equidistant from each other, approximately 200 m apart. The spatial resolution of this method is approximately 100 μm, which is sufficient for a coarse mapping of a pathology sample, but is insufficient to resolve individual cells, which are approximately 10-20 μm, or subcellular features (i.e., features less than 10 μm, such as the mitochondria). Wide adoption of this approach has been limited by the lack of scalability and accessible ways to automate and/or parallelize sequencing library preparation.

A number of new techniques have been described for reading out RNA transcription levels in tissue sections directly (i.e., in-situ), without requiring spatial barcoding, based on single molecule fluorescence in situ hybridization. These include MERFISH (Multiplexed Error-Robust Fluorescence In Situ Hybridization), STARmap (Spatially-resolved Transcript Amplicon Readout mapping), DART-FISH, seq-FISH (Sequential Fluorescence In Situ Hybridization) and others (see for example Chen, K. H., et al. (2015). Science, 348(6233), aaa6090; Wang, G., Moffitt, J. R. & Zhuang, X. Sci Rep. 2018; 8, 4847; Wang X. et al; Science, 2018; 27, Vol 361, Issue 6400, eaat5691; Cai, M. *Dissertation*, (2019) UC San Diego. ProQuest ID: Cai_ucsd_0033D_18822; and Sansone, A. Nat Methods 16, 458; 2019). In all of these techniques, individual RNA transcripts are individually resolved, typically with pre-amplification or requiring multiple instances of labeled probes. Some of these techniques have been combined with super-resolution microscopy, expansion microscopy, or both, to increase the resolution and allow more transcripts to be resolved and thus counted. This increases the complexity and costs of detection, and can require laborious sample preparation and time consuming wash protocols.

Figure 3:
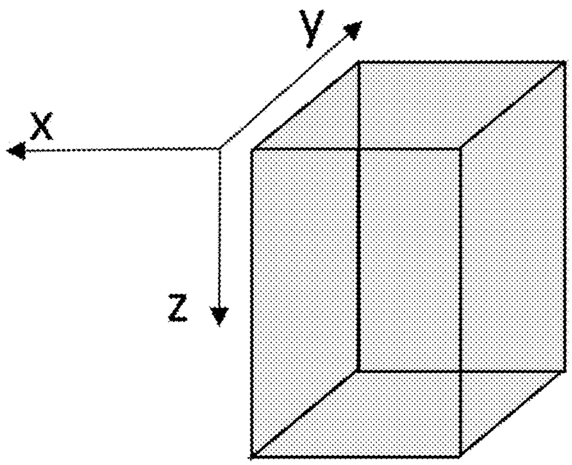
FIG. 3. A cartoon depiction of a voxel with the primary coordinate system in Cartesian coordinates. The optically resolved volume has a lateral resolution corresponding to the xy plane, and an axial resolution, corresponding to the z axis as observed in FIG. 3. In embodiments, the dimensions (i.e., the x, y, and z dimensions) of the optically resolved volume are given as (x-dimension)×(y-dimension)×(z-dimension); for example 0.5 μm×0.5 μm×2 m.

Described herein are methods for addressing these and other problems in the art. An aspect of the invention is to allow the readout of multiple RNA transcripts within one optically resolved volume (a voxel, see, e.g., FIG. 3). The method includes targeting specific RNA sequences, and "translating" them to a DNA barcode, with a means for local amplification. The method includes selecting barcodes that are widely spaced in the combinatorial space of possible barcodes (large Hamming distance). The method includes sequencing the barcodes. The methods described herein (for example within the aspects and embodiments) reveal the distribution of specific RNA molecules in cells and tissues. In this way, patterns of differential gene expression may be observed which aids in the understanding of a particular gene's function, and ultimately the phenotype of the cell.

The method includes demultiplexing the observed signal in each voxel into the set of barcodes that includes the set of barcodes being used (e.g., by linear decomposition).

Figure 1B:
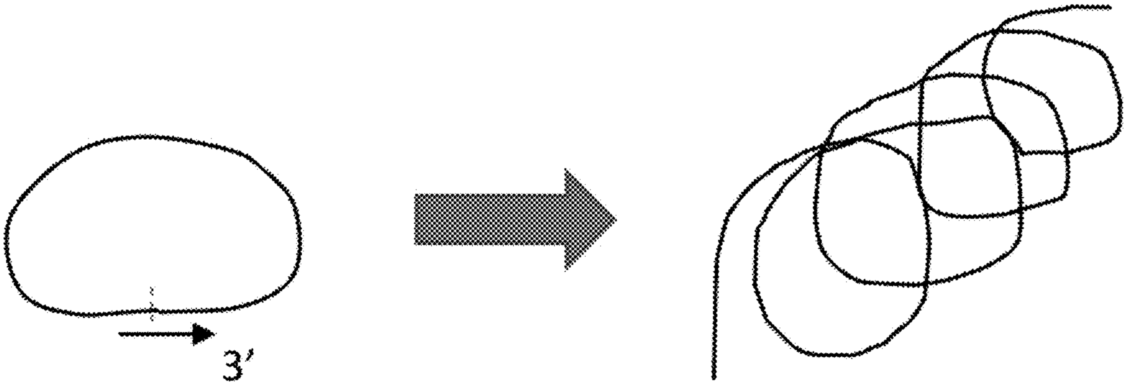
Figure 1C:
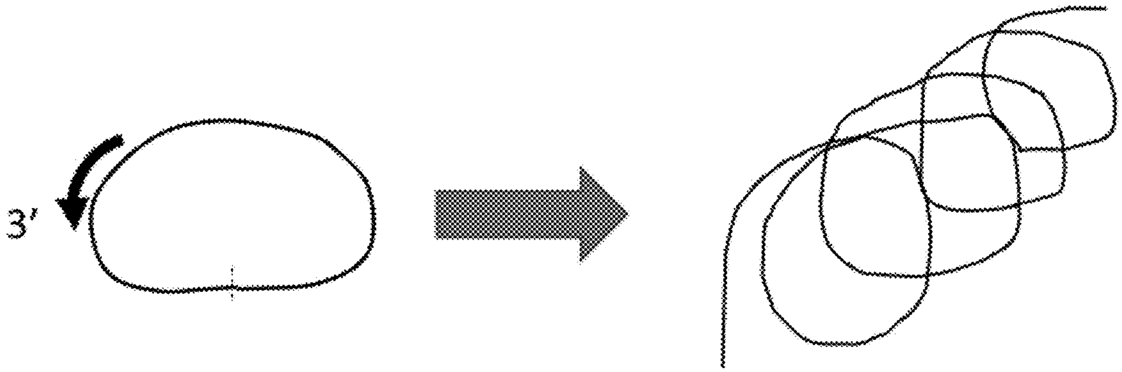

A method for "translating" RNA into a DNA barcode is to use a padlock probe, consisting of linear ssDNA, which is designed to have sequences complementary to 2 adjacent sequences on the target RNA. Once the padlock probes bind, the excess is washed away, and the linear strand of DNA is ligated to form a circle, using the RNA as a "splint". This only occurs if the two ends of the padlock probe are adjacent to each other (see, e.g., FIG. 1A). (The 5' end of the probe also has to be phosphorylated to enable ligation.) The padlock probe (and the resulting circle) contains several additional elements: a barcode for reading out the identity of the probe and its target; a complementary sequence for binding a sequencing primer. Optionally, the circle can contain multiple repeated barcodes and priming sites. The circle also needs to contain a site for RCA priming (Rolling Circle Amplification, see, e.g., FIGS. 1B-1C). In one embodiment, the priming site for RCA could have the same sequence as the sequencing primer, or have some degree of overlap.

Optionally, the RCA reaction can be done with modified nucleotides that contain chemical groups that serve as attachment points to the cell or the matrix in which the cell is embedded (e.g. a hydrogel). The attachment of the amplified product to the matrix can help confine & fix the amplicon to a small volume. In embodiments, amplification reactions include standard dNTPs and a modified nucleotide (e.g., amino-allyl dUTP, 5-TCO-PEG4-dUTP, C8-Alkyne-dUTP, 5-Azidomethyl-dUTP, 5-Vinyl-dUTP, or 5-Ethynyl dLTTP). For example, during amplification a mixture of standard dNTPs and aminoallyl deoxyuridine 5'-triphosphate (dUTP) nucleotides may be incorporated into the amplicon and subsequently cross-linked to the cell protein matrix by using a cross-linking reagent (e.g., an amine-reactive crosslinking agent with PEG spacers, such as (PEGylated bis(sulfosuccinimidyl)suberate) (BS(PEG)9)).

Optionally, one or more nucleotides within the amplification primer sequence, the sequencing primer sequence, and/or the immobilized oligonucleotide primer contains one or more functional moieties (e.g., bioconjugate reactive groups) that serve as attachment points to the cell or the matrix in which the cell is embedded (e.g., a hydrogel). In embodiments, one or more nucleotides within the amplification primer sequence, the sequencing primer sequence, and/or the immobilized oligonucleotide primer contains one or more functional moieties (e.g., bioconjugate reactive groups) that serve as attachment points to complementary bioconjugate reactive groups within the cell (e.g., a protein). In embodiments, a plurality of oligonucleotide primers are provided to the matrix in which the cell is embedded prior to amplification, wherein each of the primer oligonucleotides are attached to a specific binding reagent. In embodiments, a plurality of oligonucleotide primers are provided to the matrix in which the cell is embedded prior to amplification. In embodiments, a plurality of oligonucleotide primers is provided to the matrix in which the cell is embedded concurrently with amplification. In embodiments, the bioconjugate reactive group is located at the 5' or 3' end of the primer. In embodiments, the bioconjugate reactive group is located at an internal position of the primer e.g., the primer contains one or more modified nucleotides, such as amino-allyl deoxyuridine 5'-triphosphate (dUTP) nucleotide(s). In embodiments, the immobilized oligonucleotide primers may be used to aid in tethering the extension product to a confined area and may not be extended. In embodiments, the immobilized oligonucleotide primers may be used to aid in tethering the extension product to a confined area and may also be capable of being extended. For example, one or more immobilized oligonucleotides may be used to aid in tethering the extension product to a localized area and may be extended in an exponential RCA amplification reaction.

An alternate method is to start with a reverse transcription step to convert the RNA to cDNA. The cDNA would then act as the target for the padlock probe. In embodiments, the cDNA could serve as a splint for ligation. Yet another method would be to simply bind a large probe directly to the RNA, without doing ligation or RCA. The large probe (e.g., branched DNA or a long concatemer) would carry multiple sites for binding sequencing primers & reading identical barcodes. The drawbacks to this method include higher non-specific background and less efficient binding kinetics of a large probe. An alternate method is to start with RNA and hybridize the padlock probes directly to the RNA.

Probes can be designed to target multiple regions on the RNA of interest. This could be done to enhance the signal, and/or to provide a level of redundancy of targeting in case of mutations in a particular region. The probes that target 2 or more regions of the same RNA transcript could carry identical barcodes (for redundancy), or could carry distinct barcodes (to independently identify the region that is being detected).

Figure 1D:
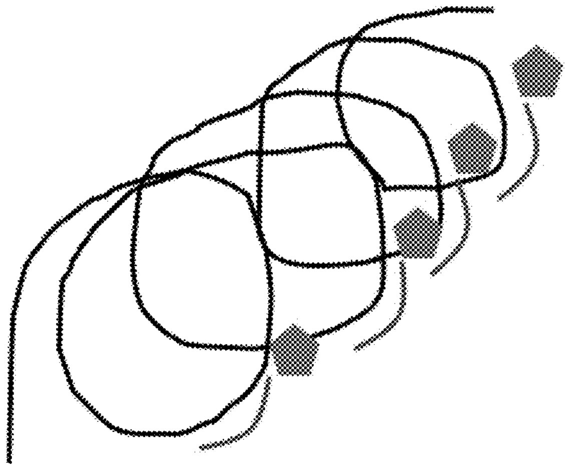
Figure 1E:
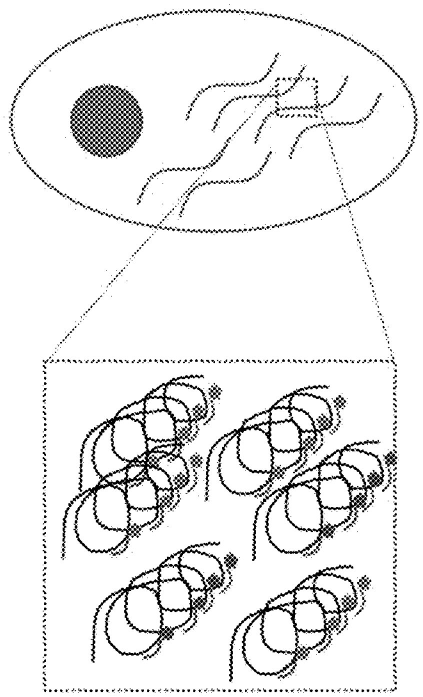

Imaging. To read out the barcoded probes, a sequencing primer is introduced, and the barcode is read out (see, e.g., FIGS. 1D-1E). Preferably, the readout is done by SBS (Sequencing-By-Synthesis), with labeled and reversibly terminated nucleotides. Similar to the amplification primer sequence, and the immobilized oligonucleotide primer described supra, the sequencing primer sequence may contain one or more nucleotides containing functional moieties (e.g., bioconjugate reactive groups) that serve as attachment points to the cell or the matrix in which the cell is embedded (e.g. a hydrogel) or to a cellular component, and the SBS reactions are performed with labeled and reversibly terminated nucleotides. In embodiments, the modified sequencing primer is provided to the matrix in which the cell is embedded following amplification or concurrently with the SBS mixture. The attachment of the SBS product to the matrix via the sequencing primer can help confine and fix the amplicon to a small, localized volume.

Figure 2:
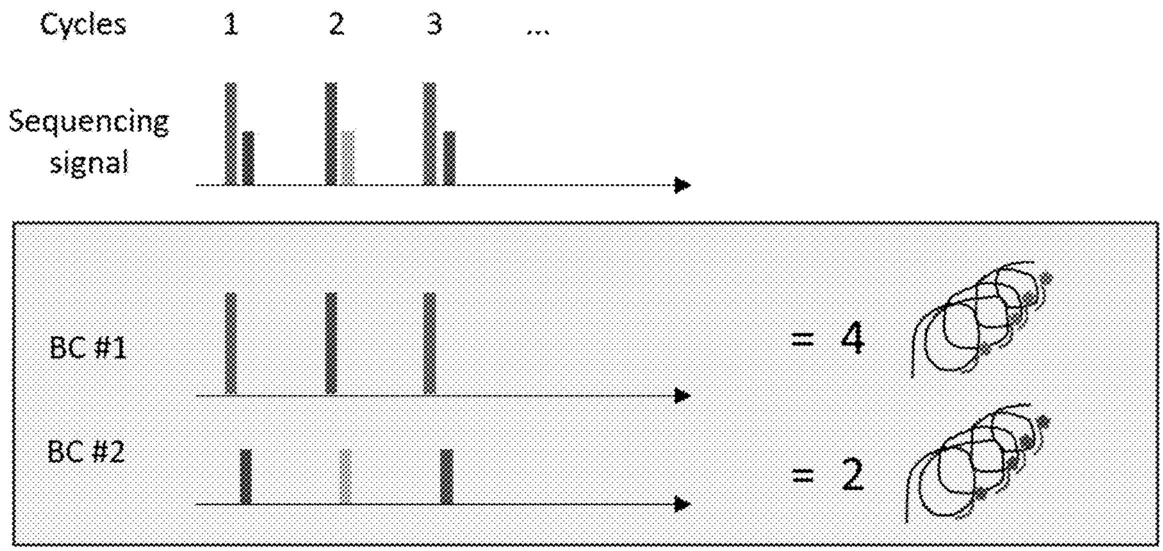
FIG. 2. Resolving one pixel of the cell as depicted in FIGS. 1A-1E, which includes the detection of a plurality of sequencing signals (i.e., fluorescent signals in this example) arising from the barcoded RNA as described according to the methods disclosed herein. Crowding within cells leads to spatial overlap of fluorescence signals within the optically resolved volume when visualized simultaneously. A linear decomposition of the sequencing signal (i.e., the multiplexed signal) into the oligonucleotide barcode basis set allows for the detection and quantitative measurement of multiple RNA in each resolved volume.

Because the identity of all the barcodes is known a priori, the resulting signal can be deconstructed (demultiplexed) into the constituent components (see, e.g., FIG. 2). Each sequencing cycle produces information about the magnitude of the signal in all 4 channels (a subset of 3 or 2 could also be used). The magnitude of the signal in all 4 channels can, for example, be represented by a signal matrix as:

Cycle 1: $C_1$, T1, $G_1$, $A_1$
Cycle 2: $C_2$, $T_2$, $G_2$, $A_2$
Cycle 3: $C_3$, $T_3$, $G_3$, $A_3$
Cycle 4: $C_4$, $T_4$, $G_4$, $A_4$
Cycle 5: $C_5$, $T_5$, $G_5$, $A_5$
Cycle 6: $C_6$, $T_6$, $G_6$, $A_6$ Each barcode can also be represented by a similar matrix. For example, a 6-base barcode such as GTCATA could be represented as:

0, 0, 1, 0
0, 1, 0, 0
1, 0, 0, 0
0, 0, 0, 1
0, 1, 0, 0
0, 0, 0, 1

The signal is then fit to a linear combination of component barcodes. For example, in embodiments when using 4-color detection (i.e., one color per nucleotides) a set of 10 sequencing cycles provides information in 40 dimensions (4 channels per cycle×10 cycles). Any of the up to $4^{10}$ possible barcodes would point to a unique position in this 40-dimensional space. Linear combinations of barcodes are thus easily resolvable, limited only by the accuracy of the sequencing signals. A typical example might be a set of 1,000-10,000 RNA targets, each encoded by a barcode selected from $4^N$ combinations, where N is the number of sequencing cycles or "digits" in the barcode. With 10 cycles, up to $4^{10}$, or approximately one million barcodes are available. This allows for the ability to select barcodes that are as far apart as possible in the available space (maximizing the Hamming distance), for more robust demultiplexing.

As illustrated in FIG. 2, each barcode can also be assigned a color (e.g., colors that are visually distinguishable) for the purpose of visualizing the spatial location of the barcode in a cell. Each sequencing cycle produces varying signal intensities in a voxel for each of the 4 channels. The brightness of the representative pixel corresponds to the local concentration of the barcode and is proportional to the product of the signal and barcode matrices (e.g., the product of the signal and barcode matrices results in a value of 4 for barcode #1 in FIG. 2, which can also be assigned a color such as green). Subsequent barcodes would also be assigned colors with pixel intensities proportional to the sequencing signal (e.g., the product of the signal and barcode matrices results in a value of 2 for barcode #2 in FIG. 2, which can also be assigned a color such as red).

Practical limitations, such as noise in the sequencing signal, will limit the total number of RNA transcripts that can be accurately detected in a single resolved volume (voxel). Reasonable upper limits might be 3, 10, 30, or >100 targets per voxel, depending on the performance of the sequencing system.

Imaging. Either 2D or 3D fluorescent imaging modalities can be used. An advantage of 3D imaging is that a larger number of individual volumes can be resolved. 3D fluorescent imaging methods include confocal microscopy, light sheet microscopy, and multi-photon microscopy. For example, if the imaging system has a lateral resolution of 0.5 um, and a depth resolution of 1.0 um, a 10×10×10 um volume would contain 20×20×10=4,000 voxels. If each voxel can resolve 10 barcodes, then this would correspond to a capacity of 40,000 reads in a 10-um cube without pushing the limits of optical resolution.

Further information can be gained by including expansion microscopy if subcellular resolution is required beyond the limits of diffraction, or if an even larger number of reads is desired.

The described methods can be applied to single cells affixed to a transparent substrate, as well as to sections of tissue on a similar substrate. In both cases (individual cells or cells in tissue), the cells are fixed and permeabilized for delivering probes, enzymes, nucleotides and other components required in the reactions.

Example 2. In Situ Proteomics

The human genome contains on the order of 25,000 genes which work in concert to produce on the order of 1,000,000 distinct proteins. A single mass spectrometry experiment can identify about 2,000 proteins or 0.2% of the total (Mirza, S. P., & Olivier, M. (2008). Physiological genomics, 33(1), 3-11), highlighting the need for novel approaches to identify more proteins. Certainly, when one considers the levels of mRNA are not proportional to the expression level of the proteins they code for, it is beneficial to determine the proteome of a sample (e.g., a cell).

The methods described in Example 1, for spatial RNA transcriptomics can also be applied to spatial proteomics. For example, the proteins of interest are targeted by specific binding reagents, such as antibodies, fragments thereof (e.g., Fabs), aptamers, and the like, which carry a barcoded nucleic acid strand. That barcode can be used as splint for a padlock probe, as described above.

If higher specificity is required, RCA-PLA (proximity ligation) methods can be used; see for example the methods, complexes, and kits described in US 2002/0064779, US 2005/0287526, and US 2014/0170654, each of which are incorporated herein by reference. With these methods, an amplified product is produced only if two specific antibodies bind to the same protein (or within ~5 nm distance). One antibody provides the DNA oligo that acts as a splint for a padlock probe, while the other antibody carries the primer for RCA. Thus, RCA reaction only occurs if both antibodies bind to their respective epitopes on the target protein (or protein complex).

Example 3. In Situ Multiplexed Sequencing of Overlapping Signals

Super-resolution microscopy in combination with expansion microscopy has been incorporated into techniques such as MERFISH and ExSeq (Expansion Sequencing) (Alon S. et al. Biorxiv, 2020, 2020.05.13.094268) to increase the resolving power of in situ sequencing. Such methods come with potential disadvantages, are expensive, burdensome and time-consuming to implement, requiring specialized optics, such as the use of high numerical aperture (NA) lenses and immersion objectives (e.g., objectives immersed in oil or water), which may limit their applications and adoption.

One constraint of such in situ transcriptomic techniques is that the resolving power becomes limited when the RNA transcript (or protein) density is too high in each voxel. For example, an imaging system with a 0.8 NA objective, the maximum resolving power is 0.5 μm×0.5 μm×1.33 μm. Recent measurements determined that typical RNA transcript density is about 100 RNA transcripts/$m^3$. Using the imaging system with an 0.8 NA objective results in an about 30 RNA molecules (or proteins) detected in a voxel. According to recent studies on its reported resolution, the MERFISH method can detect about 11 RNA transcripts in a diffraction limited spot. With MERFISH, the individual Poisson probability of detecting only one RNA transcript in a voxel is 0.18%, significantly limiting the encoding capacity for in situ transcriptomics with existing barcode technology.

The methods described herein allow for a higher in situ coding capacity by enlarging the coding space from 2D (space×barcode, e.g. MERFISH) to 3D (space×barcode×primer) through the incorporation of multiplexed sequencing primers (MSPs). MSPs enable the sequencing of a sub-set of RNAs (or proteins) per voxel, increasing the number of transcripts that can be accurately detected by controlling when the barcodes are sequenced. In an embodiment, the padlock probes contain multiple different sequencing primer binding sites, and using the methods described herein (e.g., the methods described in Example 1) multiple sequencing primers are sequentially introduced, and the barcode is read out using the sequencing methods described herein. In embodiments, the sequence method is SBS (Sequencing-by-Synthesis), with labeled and reversibly terminated nucleotides.

Different Primers, Different Barcodes, Different Transcripts

Figure 4A:
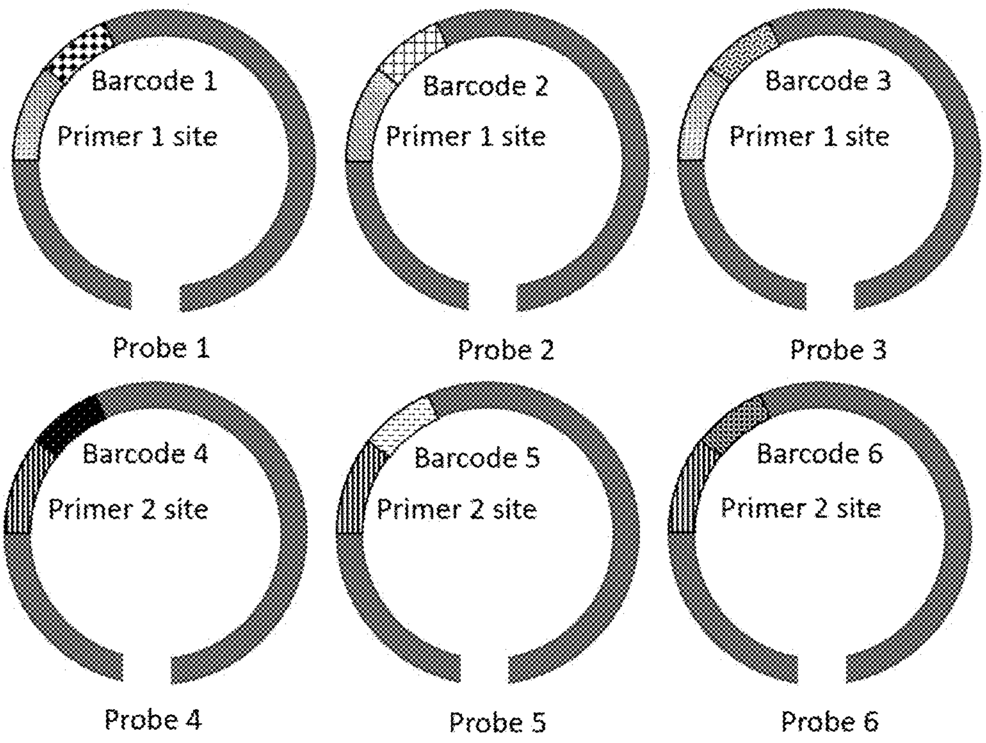
FIGS. 4A-4B. A cartoon depiction of a scheme using at least two different primers to reduce spectral overlap. A first, second, and third probe (e.g., a padlock probe as described herein) molecule in a cell, in situ, labeled as Probe 1, Probe 2, and Probe 3 in FIG. 4A, include a first primer binding sequence, labeled as Primer 1 site. Each padlock probe DNA molecule also includes a unique barcode, labeled as Barcode 1, Barcode 2, and Barcode 3 for Probe 1, Probe 2, and Probe 3, respectively. Similarly, a fourth, fifth, and sixth probe are labeled as Probe 4, Probe 5, and Probe 6 in FIG. 4A, include a second, different, primer binding sequence, labeled as Primer 2 site. Each padlock probe DNA molecule also includes a unique barcode, labeled as Barcode 4, Barcode 5, and Barcode 6 for Probe 4, Probe 5, and Probe 6, respectively. Applying the methods herein, such multiplexing of sequencing primers can be scaled to further reduce the effects of overlapping RNA density on resolving power. For example, the barcodes associated with Probe 1, Probe 2, and Probe 3 will be sequenced when a first complementary sequencing primer (i.e., complementary to Primer 1 site) is extended and the barcodes associated with Probe 4, Probe 5, and Probe 6 will be sequenced when a second complementary sequencing primer (i.e., complementary to Primer 2 site) is extended. Though the barcodes depicted in FIG. 4A are unique for each RNA molecule, the flexibility of the multiplex priming method allows that Barcode 1, Barcode 2, and Barcode 3 may be reused in conjunction with the second sequencing primer, as depicted in FIG. 4B. In other words, the primers and barcodes may be non-unique individually, but can be used in combinations that uniquely identify a particular target.
Figure 4B:
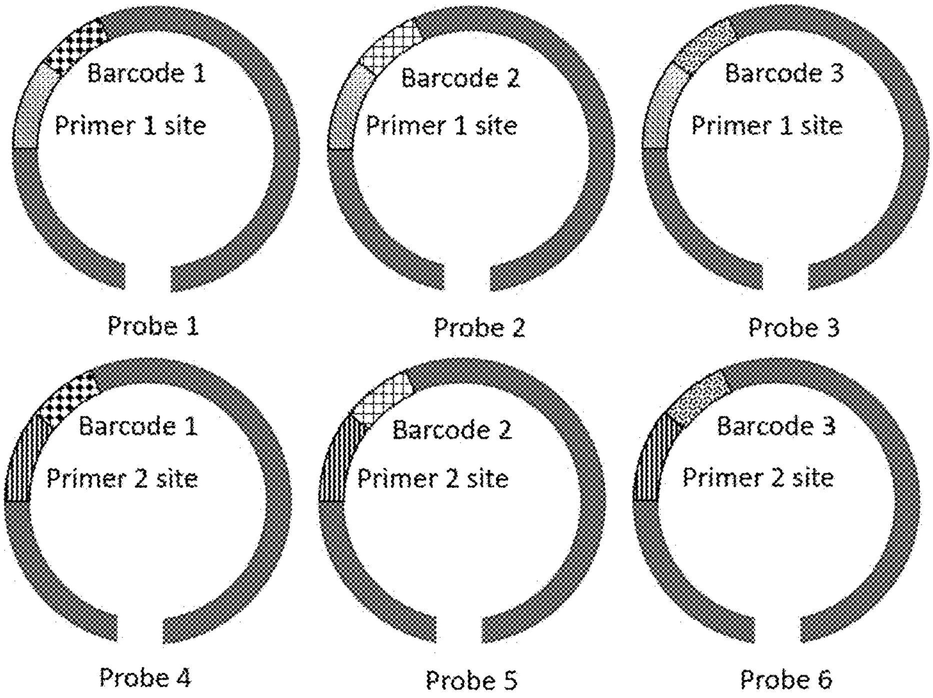

As a non-limiting example showing an embodiment of sequencing a plurality of targets within an optically resolved volume, depicted in FIGS. 4A-4B are six probes labeled as Probe 1, Probe 2, etc. Each probe contains either primer binding site 1 or primer binding site 2, as well as its own respective barcode. Primer binding site 1 and primer binding site 2 form a known primer set (i.e., a primer set of 2), and are the complementary regions for a first sequencing primer and a second sequencing primer, respectively. If all six targets are present in an optically resolved volume, only half will be detected when initiating sequencing from a primer binding site, thereby increasing detection efficiency, while still allowing for overlapping target detection. If this is scaled up to a known primer set of 8 (i.e., 8 different sequencing primer binding sites and 8 corresponding sequencing primers), the individual Poisson probability of detecting one target (e.g., one RNA transcript) in a voxel increases to 42%.

Different Combinations of Primers, Different Transcripts

Figure 5A:
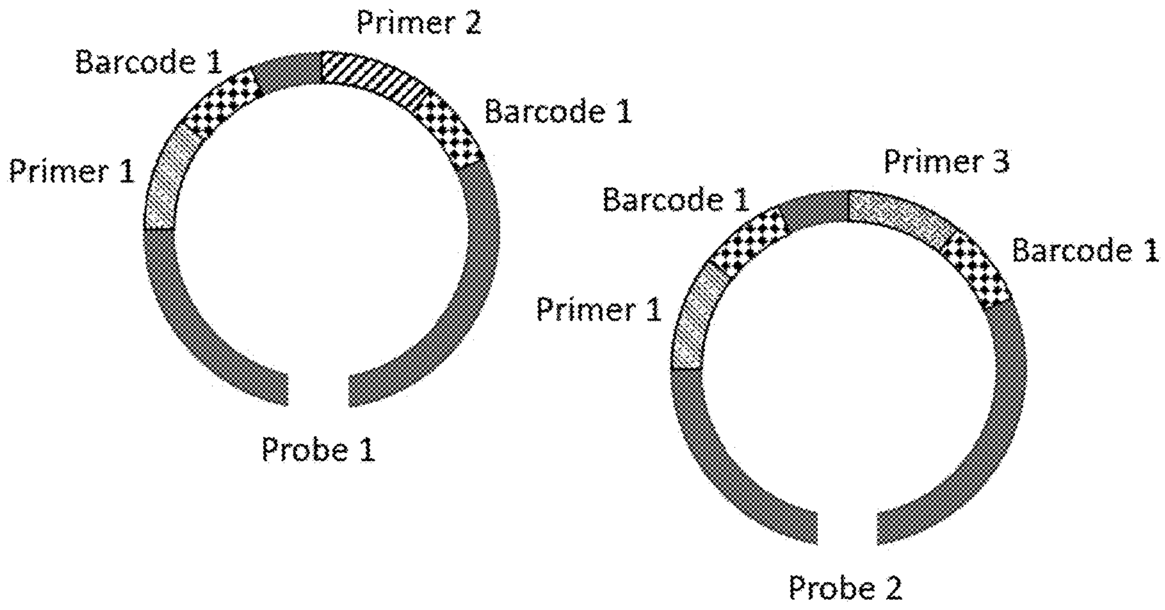
FIGS. 5A-5B.
Figure 11A:
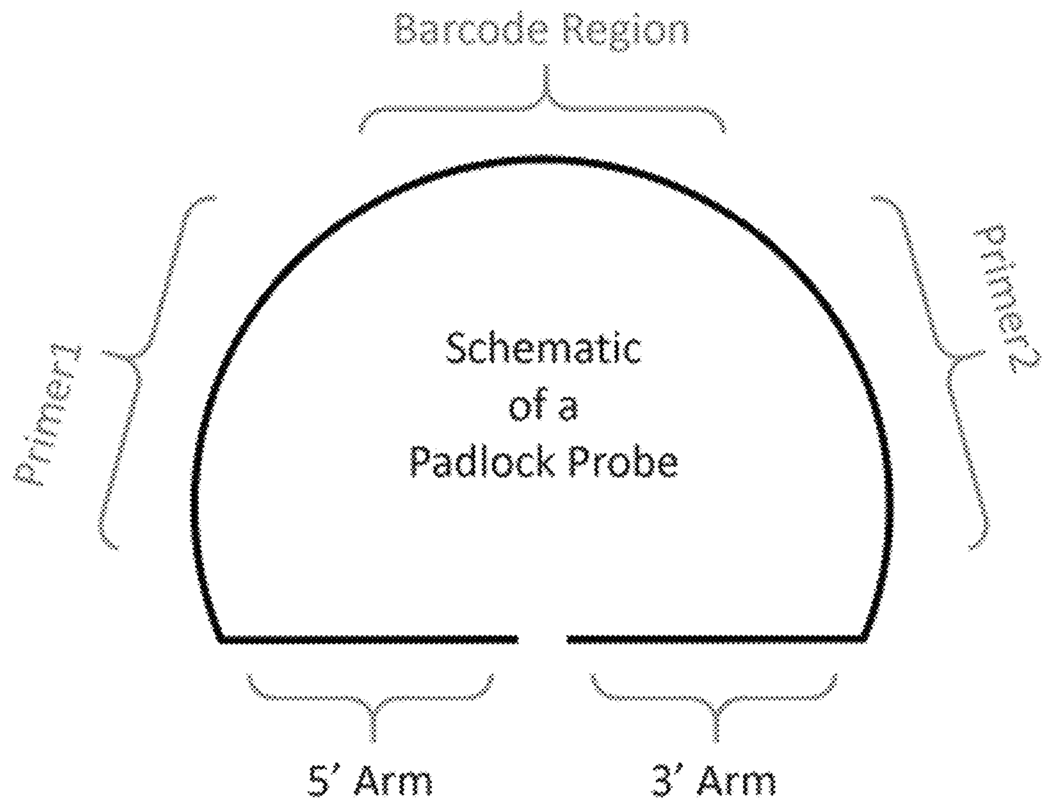
FIGS. 11A-11B depicts an embodiment of a padlock probe (FIG. 11A) and an illustration of two padlock probes hybridizing to the V and J regions flanking a CDR3 sequence of an immunoglobulin coding mRNA (FIG. 11B). In embodiments, the 5' arm and the 3' arm are about 15-20 nucleotides; the Primer1 and Primer2 regions are about 20 to 35 nucleotides; and the barcode region is about 8 to 12 nucleotides. The total length of the padlock probe is about 80 to 125 nucleotides in length (e.g., 100 nucleotides in total). While depicted as equal lengths in FIG. 11A, it is understood that the 5' arm (e.g., a first domain) and the 3' arm (e.g., a second domain) are not necessarily the same length. In embodiments, it may be favorable to have one arm (e.g., the 3' arm) be a shorter sequence than the other arm (e.g., the 5' arm). For example, the 3' arm may hybridize to a sequence containing 10 nucleotides, whereas the 5' are hybridizes to a sequence containing 20 nucleotides.
Figure 11B:
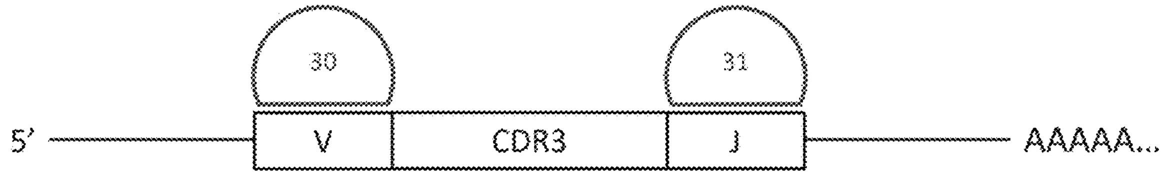

Alternatively, different combinations of primer binding sites are introduced into the padlock probes while keeping the barcodes the same, see for example FIG. 5A or FIG. 11A. A first circular polynucleotide, labeled Transcript 1 in FIG. 5A, includes a first primer binding site (a nucleic acid sequence complementary to a first sequencing primer, labeled Primer 1) before a barcode (labeled as Barcode 1), and a second primer binding site (a nucleic acid sequence complementary to a second sequencing primer, labeled Primer 2) before another instance of the same barcode. The primer binding sites (i.e., Primer 1 and Primer 2) are different from each other such that the first primer will not hybridize to the second primer binding site, and vice versa. A second circular polynucleotide, labeled Transcript 2 in FIG. 5A, includes a first primer binding site (a nucleic acid sequence complementary to a first sequencing primer, labeled Primer 1) before a barcode (labeled as Barcode 1), and a third primer binding site (a nucleic acid sequence complementary to a third sequencing primer, labeled Primer 3) before another instance of the same barcode (labeled as Barcode 1). Though the barcodes depicted in FIG. 5A are the same for each primer binding site, the flexibility of the multiplex priming method allows different barcodes to be used (e.g., Primer 1-Barcode 1 and Primer 2-Barcode 2 on Transcript 1 without modifying Transcript 2). The primer binding sites (i.e., primer 1, primer 2, and primer 3) are different from each other such that the first primer will not hybridize to the second primer binding site or the third primer binding site, the second primer will not hybridize to the first primer binding site or the third primer binding site, and the third primer will not hybridize to the first primer binding site or the second primer binding site. In this example, two overlapping transcripts in a voxel are targeted by a set of 3 primers (i.e., a primer set of 3). During the first round of sequencing, using primer 1, the two transcripts are unresolvable. However, in the second round of sequencing, primer 2 can hybridize and sequence the barcodes of the first RNA. Similarly, in the third round of sequencing primer 3 hybridizes and sequence the barcodes of the third RNA. By such iterative means, two otherwise overlapping RNA transcripts are resolved.

Figure 5B:
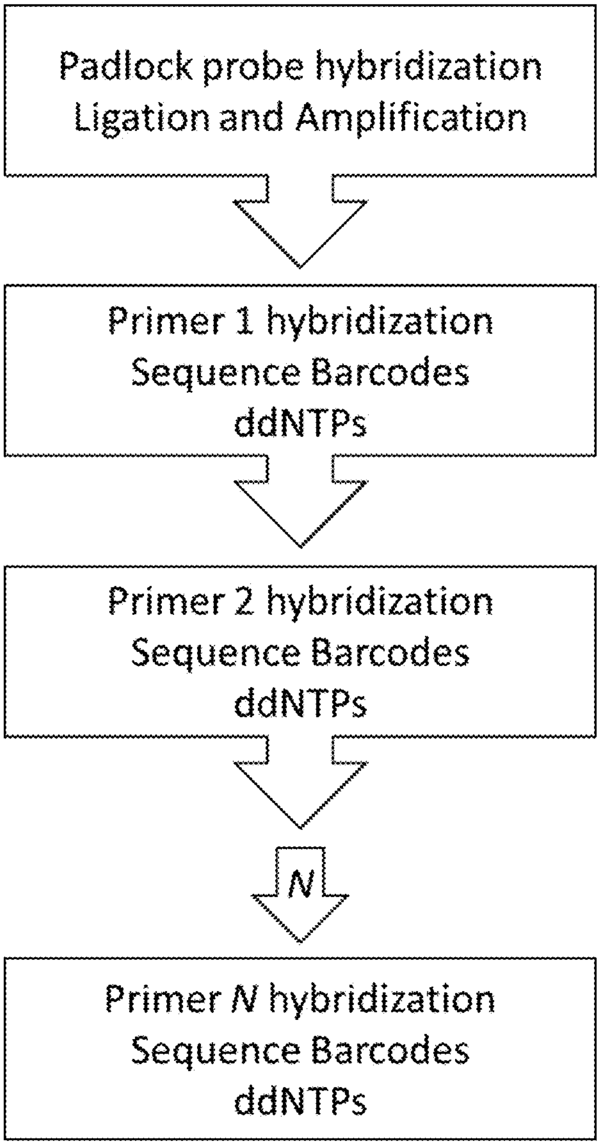

In embodiments, following sequencing of the first barcode to a sufficient read length (e.g., the entirety of the barcode), the sequencing cycle is terminated. A sequencing cycle may be terminated by incorporated dideoxynucleotides triphosphates (ddNTPs) such that no additional nucleotides may be incorporated into an extension strand complementary to the first barcode. This process is repeated for the second and third barcodes, up to N number of primers in the set of primers, see the flowchart described in FIG. 5B. When combined with iterative sequencing, this further reduces the effects of RNA overlapping and increase detection efficiency.

Different Primers, Same Barcode, Same Transcript

An alternative implementation of these methods includes targeting the same barcode with multiple primers. For example, MSPs that target each barcode are used to resolve a plurality of overlapping RNAs (see FIG. 6). In an embodiment, three different sequencing primers are designed to target three probes containing the same barcode. During a first set of sequencing reads (i.e., a first plurality of sequencing cycles), the first primer will sequence the barcoded probes containing the first primer binding site (referred to as probe 1 in FIG. 6). The barcode probes containing a second different primer binding site (referred to as probe 2 in FIG. 6) are sequenced during the second set of sequencing reads (i.e., a second plurality of sequencing cycles). Similarly, the barcode probes containing a third different primer binding site (referred to as probe 3 in FIG. 6) are sequenced during the third set of sequencing reads (i.e., a second plurality of sequencing cycles). Each barcoded probe contains a unique primer binding site. In this example, the plurality of targets in a voxel are targeted by a set of 3 primers (i.e., a primer set of 3). During the first round of barcode sequencing, using primer 1, the first region of the RNA is detected. In the second round of sequencing, primer 2 can hybridize and sequence the barcodes of the second region of the RNA. Similarly, in the third round of sequencing, primer 3 hybridizes and sequence the barcodes of the third region of the RNA. The combination of iterative sequencing that the distinct primers helps to further deconvolute the signals.

Figure 6:
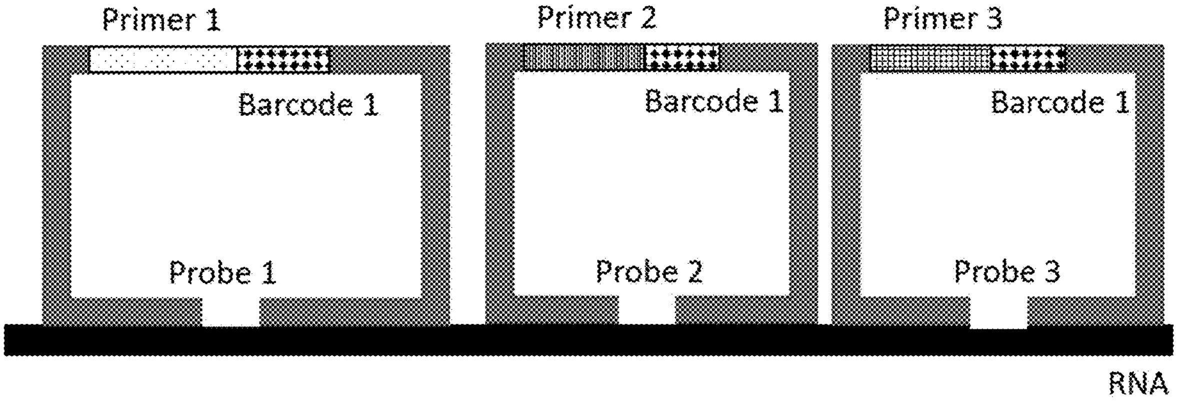
FIG. 6. A cartoon representation of a plurality of padlock probes hybridized to the same RNA molecule, albeit at different regions. A first padlock probe (labeled as Probe 1) includes a first primer binding site (a nucleic acid sequence complementary to a first sequencing primer, labeled Primer 1) before a barcode (labeled as Barcode 1). In a similar manner, a second and third padlock probe include a second primer binding site (a nucleic acid sequence complementary to a second, different, sequencing primer, labeled Primer 2) and a third primer binding site (a nucleic acid sequence complementary to a third, different from both Primer 1 and Primer 2, sequencing primer, labeled Primer 3), respectively, before a barcode of the same sequence (also labeled as Barcode 1). During the first round of barcode sequencing (following probe circularization and amplification), using primer 1, the padlock probe hybridized to the first region of the RNA is detected. In the second round of sequencing, primer 2 can hybridize and sequence the barcode of the padlock probe hybridized to the second region of the RNA. Similarly, in the third round of sequencing, primer 3 can hybridize and sequence the barcode of the padlock probe hybridized to the third region of the RNA.

While FIG. 6 depicts the regions as non-overlapping, in embodiments the regions overlap. Using padlock probes that target different regions of the same type of RNA (e.g., a 16S rRNA gene), it is possible overlap with variable and conserved regions of different RNA molecules, but the same RNA type.

In embodiments, following sequencing of the first barcode to a sufficient read length (e.g., the entirety of the barcode), the sequencing cycle is terminated. A sequencing cycle may be terminated by incorporated dideoxynucleotides triphosphates (ddNTPs) such that no additional nucleotides may be incorporated into an extension strand complementary to the first barcode. This process is repeated for the second and third barcodes, up to N number of primers in the set of primers, see the flowchart described in FIG. 5B. When combined with iterative sequencing, this further reduces the effects of RNA overlapping and increase detection efficiency.

The methods described herein include techniques amenable to simplistic implementation and instrument design while still capturing valuable information from a complex sample. The numerical aperture (NA) of an objective is related to the image resolution, i.e., the ability of the objective to distinguish features in the in situ sample. In general, objectives with a high NA value produce an image which is highly resolved compared to objectives which have lower NA. Due to the NA's dependence on the refractive index of the medium between the sample and the front lens (e.g., air, water, oil), it is difficult to achieve NA values above 0.95 with dry objectives (i.e., a sample and a lens, which are separated by air). Higher NAs can be obtained by increasing the imaging medium refractive index, for example using water (refractive index=1.33), glycerin (refractive index=1.47), or immersion oil (refractive index=1.51), however this limits the compatibility of the image acquisition device. If using a 'wet' setup, where the imaging lens and sample is submerged in water, glycerin, or oil for example, it is exceedingly complex to modulate the temperature of the sample, a parameter often tuned during various amplification and sequencing cycles. Moreover, objectives with a high NA generally have a very shallow depth of field thereby complicating image acquisition of a plurality of targets in a cell in situ, where the sample (i.e., the cell and surrounding milieu) provides for a complex topology, thus making it difficult resolve sample detail.

The ability of MSPs to resolve a significantly higher proportion of targets (e.g., RNAs) in a sample also obviates the need for expansion microscopy techniques, e.g., thick hydrogels that slow the diffusion of sequencing reagents to a target nucleic acid, and additionally make the sample amenable to heating and cooling protocols.

As discussed throughout the application, and for example within Example 1, because the identity of all the barcodes is known a priori, the resulting signal can be deconstructed (demultiplexed) into the constituent components. The sequencing cycles produces information about the magnitude of the signals in all channels used (e.g., 4-channel-4-color; 3-channel-3-color; or 2-channel-2-color). The multiplexed signal is then fit to a linear combination of component barcodes. For example, in embodiments when using 4-color detection (i.e., one color per nucleotide type, such as for example dATP-red; dCTP-blue; dGTP-green; and dTTP-yellow) a set of 10 sequencing cycles provides information in 40 dimensions (4 channels per cycle×10 cycles). Any of the $4^{10}$ possible barcodes would point to a unique position in this 40-dimensional space. Linear combinations of barcodes are thus easily resolvable, limited only by the accuracy of the measured sequencing signals. A typical example might be a set of 1,000-10,000 RNA targets, each encoded by a barcode selected from $4^N$ combinations, where N is the number of sequencing cycles or "digits" in the barcode. With 10 cycles, $4^{10}$, or approximately one million barcodes, are available. This allows for the ability to select barcodes that are as far apart as possible in the available space (maximizing the Hamming distance), for more robust demultiplexing and error-correcting coding.

The described methods can be applied to single cells affixed to a transparent substrate, as well as to sections of tissue on a similar substrate. In both cases (individual cells or cells in tissue), the cells are fixed and permeabilized for delivering probes, enzymes, nucleotides and other components used in the reactions. This example recites RNA transcripts, however the methods are also applicable to proteins using the methods described herein (e.g., associating an oligonucleotide barcode with each of the plurality of targets by contacting each of the targets with a specific binding reagent, such as an antibody). Thus, the methods of the present example may be applied, mutatis mutandis, to detecting a plurality of different proteins within an optically resolved volume of a cell in situ.

Example 4: Clinical Profiling of Innate Immune Cell Factors

The innate immune system employs germline-encoded pattern-recognition receptors (PRRs) for the initial detection of microbes. PRRs recognize microbe-specific molecular signatures known as pathogen-associated molecular patterns (PAMPs). PRRs activate downstream signaling pathways that lead to the induction of innate immune responses by producing inflammatory cytokines, type I interferon (IFN), and other mediators. These processes trigger immediate host defensive responses such as inflammation and adaptive immune responses critical for the clearance of infecting microbes (Kawasaki and Kawai, 2014, and Akira et al., 2006).

Toll-like receptors (TLRs) are a family of PRRs and part of the first line of defense against invading microbes. Ten different TLRs are expressed to varying degrees in human immune cell subsets, including NK cells, macrophages, B cells, and dendritic cells (DCs) (Nie et al., 2018). TLR activation leads to the production of pro-inflammatory cytokines, triggering an innate immune response and initiating the adaptive immune response (Altfeld and Gale, 2015). Single-cell systems-level analysis of TLR activation has highlighted the cell-to-cell diversity in monocyte responses to TLR ligands, with distinct cytokine patterns correlating to TLR ligand specificity (O'Gorman et al., 2015).

The severe acute respiratory syndrome coronavirus 2 (SARS-CoV-2) resulted in a pandemic in late 2019 and early 2020 with millions of infections of coronavirus disease 2019 (COVID-19). Single-stranded RNA sequences recognized by TLR 7/8 have been identified as PAMPs in the SARS-CoV-2 genome (Moreno-Eutimio et al., 2020). Rare loss-of-function variants of the X-chromosomal TLR7 were recently identified in 4 young male patients with severe COVID-19, indicating a potential genetic predisposition to contract coronavirus infections (van der Made et al., 2020). Utilizing the methods described herein, comprehensive interrogation of innate immune response genes, for example TLR genes in DCs, may be realized and provide insight into the predisposition of an individual to severe pathogen-associated disease and guide clinical decision making.

In situ sequencing involves tissue and/or cellular extraction, combined with the fixation and permeabilization of cells, followed by amplification of the target nucleic acid fragments for sequencing. Briefly, cells and their surrounding milieu are attached to a substrate surface, fixed, and permeabilized using known methods. The TLR-targeted padlock probes are then hybridized to TLR target nucleic acid sequence of interest or a portion thereof, followed by ligation to complete circularization oligonucleotide. The circularized oligonucleotide is then amplified with a strand-displacing polymerase, generating an extension product with multiple copies of the circular template. This extension product is then primed with a sequencing primer and subjected to sequencing processes as described herein, providing a view of TLR mutations present in a cell.

REFERENCES FOR EXAMPLE 4: Kawasaki T. and Kawai T. Front. Immunol., 2014, 5:461; Akira S. et al. Cell, 2006, 124, 783-801; Nie L. et al. Front. Immunol., 2018, 9:1523; O'Gorman et al. J. Allergy Clin. Immunol., 2015, 136, 1326-1336; Altfeld M. and Gale, Jr. M. Nature Immunol., 2015, 16, 554-562; Moreno-Eutimio M. et al. Microbes Infect., 2020, 22, 226-229; and Van der Made C. et al. JAMA, 2020, 324:7.

Example 5: Monitoring Transcriptional Response to Pharmacological Agents

Large projects such as the Cancer Cell Line Encyclopedia (CCLE, Barretina et al., 2012) and Genomics of Drug Sensitivity in Cancer (GDSC, Garnett et al., 2012) have analyzed hundreds of cancer cell lines and generated data on the genotypes and cellular responses to pharmacological treatment. Additional work has combined multi-omics approaches (e.g., RNA-seq and ATAC-seq) from drug-treated lung cancer cell lines to profile cellular responses and identify novel drug targets (Suzuki et al., 2019). Similar approaches using bulk and single-cell transcriptomics in fibroblasts and mononuclear phagocytes, challenged with immune stimuli such as a genetically modifying agent, revealed that transcriptionally diverging genes like cytokines and chemokines varied in expression across cells (Hagai et al., 2018). Studies such as these have taken an initial step at mapping the cellular response to therapeutic agents but lack resolution into the dynamic cellular and subcellular heterogeneity of the cellular programs governing downstream physiological effects.

In gastric cancer (GC), genomic profiling is used to define clinical subtypes based on mutational status of oncogenes such as ERBB2, KRAS, TP53, and PIK3CA (Ho and Tan, 2019). Tumor heterogeneity has profound implications for therapy selection. In a clinical trial testing FGFR2 inhibition in GC, durable responses were observed only in high-level FGFR2 clonally amplified tumors, as assessed by FISH-based in situ heterogeneity mapping (Pearson et al., 2016). A comparison of paired FGFR2 expression at baseline and 15 days post-treatment further showed significant decreases in FGFR2 mRNA only in the sub-clonal, heterogeneously amplified tumor, possibly reflecting clonal selection of non-amplified compartments as a result of therapeutic pressure. The sequencing methods described herein can be applied to the molecular profiling of a GC tumor to monitor whether FGFR2 expression is perturbed during therapy.

Briefly, tumor cells obtained from a GC patient before, during, and/or after pharmacological treatment are attached to a substrate surface, fixed, and permeabilized according to known methods in the art. Targeted padlock probes for FGFR are then annealed to the nucleic acid of interest and ligated. The resulting circularized oligonucleotide is primed with an amplification primer and extended with a strand-displacing polymerase to generate a concatemer containing multiple copies of the target nucleic acid sequence. This extension product is then primed with a sequencing primer and subjected to sequencing processes as described herein.

Such methods may be applied to assess whether a patient being treated for any physiological or psychological condition that requires a pharmacological agent has a transcriptional response in a target cell type that may be indicative of the clinical efficacy of the treatment. These can also provide temporal information for patients under short- or long-term drug treatment to provide relevant clinical information, for instance, gene signatures indicative of drug resistance. Non-invasive options for such a diagnostic tool include isolation of circulating tumor cells (Rossi and Zamarchi, 2019), or isolation of immune cells from whole blood or bodily fluids.

REFERENCES FOR EXAMPLE 5: 1. McGranahan N. and Swanton C. Cell, 2017, 168, 613-628; 2. Nik-Zainal S. et al. Nature, 2016, 534, 47-54; 3. Barretina J. et al. Nature, 2012, 483, 603-607; 4. Wang Y. et al. Lancet, 2005, 365, 671-679; 5. Paik S. et al. New Engl. J. Med., 2004, 351, 2817-2826; 6. Parker J. et al. J. Clin. Oncol., 2009, 27, 1160-1167; 7. Svedlund J. et al. EBioMedicine, 2019, 48, 212-223; 8. Montemurro F. and Scaltriti M. J. Pathology, 2014, 232, 219-229; 9. Asif H. et al. Asian Pac. J. Cancer P., 2016, 17, 1609-1615; 10. Gaibar M. et al. J. Oncol., 2020, 2020, 1-13; 11. Garnett M. et al. Nature, 2012, 483, 570-575; 12. Suzuki A. et al. Sci. Rep., 2019, 9, 19529; 13. Hagai T. et al. Nature, 2018, 563, 197-202; 14. Ho S. and Tan P. Cancer Sci., 2019, 110, 3405-3414; 15. Pearson A. et al. Cancer Discov., 2016, 6, 838-851; 16. Rossi E. and Zamarchi R. Frontiers Genetics, 2019, 10, 958; and 17. Robichaux J. et al. Nat. Med., 2018, 24, 638-646.

Example 6: Profiling Genome Editing Efficiency

The evolution of gene editing towards clinical practice has developed through recent advancements in programmable nucleases, such as zinc-finger nucleases (ZFNs), transcription activator-like effector nucleases (TALENs), and clustered regularly interspaced short palindromic repeat (CRISPR)-Cas-associated nucleases. Targeted DNA alterations begin with the generation of nuclease-induced double-stranded breaks (DSBs), which lead to the stimulation of DNA recombination mechanisms in mammalian cells (Kosicki et al., 2018). Nuclease-induced DNA DSBs can be repaired by one of the two major mechanisms present in eukaryotic cells: non-homologous end joining (NHEJ) and homologous recombination (HR), resulting in gene disruptions or targeted integration, respectively (Kass and Jasin, 2010).

The CRISPR-Cas systems are divided into two classes based on the structural variation of the Cas genes and their organization style. Specifically, class 1 CRISPR-Cas systems consist of multiprotein effector complexes, where class 2 systems comprise only a single effector protein; at least six CRISPR-Cas types and 29 subtypes have been reported (Makarova et al., 2015). At present, the most frequently used subtype of CRISPR system is the type 2 CRISPR/Cas9 system, which depends on a single Cas protein from *Streptococcus pyogenes* (SpCas9) targeting DNA sequences (Jiang et al., 2013). A single-stranded guide RNA (sgRNA) and a Cas9 endonuclease form a targeting complex, wherein the sgRNA binds to the target sequence and Cas9 precisely cleaves the DNA to generate a DSB and subsequently activate cellular repair programs. Conveniently, changing the sgRNA sequence allows the targeting of new sites, without requiring changes to the Cas9 protein (Li et al., 2020).

Specific delivery methods have been developed for targeting both Cas9 and sgRNAs directly to the organ of interest in vivo, including direct transfection, lentiviral and adeno-associated virus (AAV)-based transduction, and nanoparticle delivery (Tschaharganeh et al., 2016). Cells may also be isolated from a patient to be treated, edited, and then re-engrafted back to the patient. Such an approach is used in the preparation of chimeric antigen receptor (CAR) T cells for cancer immunotherapy, wherein the patient's T cells are isolated, reengineered and modified with tumor-antigen-specific receptors and costimulating molecules, transduced with a CAR viral vector, amplified, and then infused back into the patient (Li et al., 2020). Furthermore, the development of allogeneic universal "off-the-shelf" CAR T cells has been demonstrated effectively using a one-shot CRISPR protocol to knockout endogenous TCR and HLA class 1 molecules (Ren et al., 2017).

Determining whether the cell of interest has been successfully targeted by a genome editing endonuclease is traditionally performed via bulk harvesting of cell lysate and analysis of total genomic material (Cromer et al., 2018). Some of the current challenges in therapeutic targeting involve increasing the specificity of gene correction, improving the efficiency of nuclease editing, and optimizing the delivery systems (Li et al., 2020). By using the in situ sequencing methods described herein, high-resolution information is obtained to decipher the effectiveness of a genome editing treatment, for example, the production of allogeneic CAR T cells.

Briefly, a population of T cells is subjected to a genome editing technique, for example CRISPR/Cas9, to knockout the TCR and HLA class 1 loci. The cells are then attached to a substrate surface, fixed, and permeabilized according to known methods in the art. Targeted oligonucleotide probes for the TCR and HLA class 1 loci are then annealed to the nucleic acid of interest, followed by ligation. The resulting circularized oligonucleotide is primed with an amplification primer and extended with a strand-displacing polymerase to generate a concatemer containing multiple copies of the target nucleic acid sequence. This extension product is then primed with a sequencing primer and subjected to sequencing processes as described herein.

Example 7: Profiling Tumor Infiltrating Lymphocytes in a Biopsy

The assessment of tumor infiltrating lymphocytes (TILs) in histopathological specimens can provide important prognostic information in diverse solid tumor types and may also be of value in predicting response to treatments. The altered protein products in cancer cells can function as neoantigens and elicit an immune response (Hendry et al., 2017). This immune response can lead to perturbations in the tumor microenvironment that may play a role in cancer progression and outcome (Coussens et al., 2013). Specifically, the inflammatory tumor microenvironment may pose an obstacle to the efficacy of novel cancer immunotherapies, such as engineered chimeric antigen receptor (CAR) NK and T cells. The infiltration of CAR NK and CAR T cells into a tumor is a critical step in exerting anti-tumor effects that can be inhibited by various features of the tumor microenvironment, including concentrated blood vessels and extracellular matrix (Ma et al., 2019).

CAR cells that target the B-cell antigen CD19 are being investigated in various clinical trials for the treatment of advanced B-cell lymphoma, among other hematological cancers. Next-generation CARs, such as FT596 universal NK immunotherapy, have various engineered anti-tumor functional modalities to overcome the tumor microenvironment and synergistically exert anti-tumor activity (Nayyar et al, 2019). In the case of FT596, one such feature is a CAR optimized for NK cell biology with a NKG2D transmembrane domain, a 2B4 co-stimulatory domain, and a CD3-zeta signaling domain for targeting CD19. In a clinical setting, assessing the extent of TILs would be a significant barometer of treatment efficacy and provide insight into the progression of oncolytic activity, allowing clinicians to learn which antigens are being recognized or what T cell types are capable of infiltrating a tumor, presenting unique opportunities for immunotherapies.

The methods described herein provide a novel in situ sequencing approach for profiling the tumor microenvironment at a transcriptional level, for example, to determine the presence, magnitude, and identity of TILs (e.g., native or allogenic TILs). Briefly, a tumor tissue section is attached to a substrate surface, fixed, and permeabilized according to known methods in the art. The targeted padlock probes are then hybridized to target nucleic acid sequence of interest or a portion thereof, followed by ligation to complete circularization oligonucleotide. Alternatively, a specific binding reagent comprising an oligonucleotide barcode contacts the TIL. A padlock probe is then allowed to contact and hybridize to two adjacent nucleic acid sequences of the barcode, followed by ligation to complete circularization of the oligonucleotide. The circularized oligonucleotide is then amplified with a strand-displacing polymerase, generating an extension product with multiple copies of the circular template. This extension product is then primed with a sequencing primer and subjected to sequencing processes as described herein, thereby providing a high-resolution view of infiltrating CAR NK and/or CAR T cell molecular features that can be combined with additional histological and immunohistochemistry modalities to guide clinical decision-making.

REFERENCES FOR EXAMPLE 7: Hendry et al. Adv. Anat. Pathol., 2017, 24, 235-251; Coussens et al. Science, 2013, 339, 286-291; Ma et al. Int. J. Biol. Sci., 2019, 15, 2548-2560; and Nayyar et al. Frontiers Oncol., 2019, 9, 51.

Example 8: Profiling the States of the Tuberculosis Granuloma

Tuberculosis (TB) is one of the top ten causes of death worldwide and the leading cause of death from a single infectious agent (Chakaya J et al. Int. J. Infect. Dis. 2021; S1201-9712(21): 00193-4). TB is caused by the pathogenic bacteria species *Mycobacterium tuberculosis* (MTb), which infects cells of the upper airway of an organism. Macrophages internalize invading MTb cells by phagocytosis, which are then believed to reside within the endosomes of the macrophage. The immune system attempts to isolate the infection and aggregates infected macrophages into a granuloma. In a minority of cases, the integrity of the granuloma is compromised and MTb cells infect other parts of the lung and/or enter the lymph system and reach other organs or systems, rapidly deteriorating patient outcomes. Existing clinical diagnostics, such as Cepheid's Xpert® MTB/RIF, focus on differentiating whether a patient presenting with symptoms of TB is infected with a multi-drug resistant and rifampicin resistant strain, which simultaneously detects both. Such diagnostic tests provide key decision metrics for the type of isolation and treatment that would be most efficacious for a patient. Tests such as these, though useful for point-of-case diagnostic purposes, do not provide information on the factors regulating the development of the granuloma. Rifampicin resistance may occur alone or in association with resistance to isoniazid and other drugs (Steingart K R et al. Cochrane Database Syst. Rev. 2014; 2014 (1): C009593). Rifampicin inhibits bacterial DNA-dependent RNA polymerase, encoded by the RNA polymerase gene rpoB, and resistance has mainly been associated with mutations in an 81-base pair region of the rpoB gene, including the mutations Q513P, Q513K, H256R, S531L, or S531W (Al-Mutairi N M et al. BMC Infect. Dis. 2019; 19: 3). Resistance to ethambutol (EMB), isoniazid (INH), and pyrazinamide (PZA) include mutations in the embB, inhA, and pncA genes, respectively. Mutations in one or more of these genes are frequently found in multi-drug resistant MTb strains.

It is known that cytokines such as IFNγ, TGF-beta and other signaling systems are involved in the establishment and maintenance of the TB granuloma (Gern B H et al. Cell Host Microbe. 2021; 29(4): 594-606). In situ sequencing of TB granulomas in lungs from mice at different times after infection have shown that the necrotic centers of encapsulated granulomas express transcripts associated with immunosuppression (Foxp3, IL10), whereas those transcripts in the granuloma periphery associate with activated T cells and macrophages (Carow B et al. Nature Comm. 2019; 10: 1823). Considering these recent discoveries, there is still a need for improved models of the factors that control granuloma integrity, maintenance, and evolution over time. Developing an improved understanding of the factors regulating an individual patient's infection and the mechanisms driving disease progression may aid earlier intervention and lead to targeted therapeutics and improved patient outcomes.

The methods described herein provide a novel in situ sequencing approach for profiling the TB granuloma at a transcriptional level enabling scientists and clinicians to monitor the disease state, for example, to determine how its regulation, integrity, and function evolve over time. Briefly, a TB granuloma sample (e.g., from a subject biopsy or an in situ TB model) is attached to a substrate surface, fixed, and permeabilized according to known methods in the art. Optionally, the sample is cleared (e.g., digested) of proteins, lipids, or proteins and lipids. The granuloma sample is obtained from one or more regions of the granuloma, for example, the necrotic center and the granuloma rim. Samples are obtained from the subject at various time points of TB infection, for example, before symptoms appear, early in disease progression (about 3 weeks post-infection), and late in disease progression (about 8 to 12 weeks post-infection). The targeted padlock probes are then hybridized to target nucleic acid sequence or a portion thereof (e.g., rpoB, IFNγ, TGF-beta, FOX3P and/or IL10 genes), followed by ligation to complete circularization oligonucleotide. Alternatively, a specific binding reagent comprising an oligonucleotide barcode contacts a target within the granuloma. For example, a specific binding reagent may specifically bind to a nucleic acid, a protein, a lipid, a lipid derivative, a phospholipid, a fatty acid, a triglyceride, a peptidoglycan, a glycerolipid, a glycerophospholipid, a sphingolipid, a polysaccharide, or a saccharolipid. A specific binding reagent may specifically bind to a MTb cell wall component, e.g., mycolyl-arabinogalactan, arabinogalactan, trehalose monomycolate, or trehalose dimycolate (Thanna S and Sucheck S J. Medchemcomm. 2016; 7(1): 69-85). A padlock probe is then allowed to contact and hybridize to two adjacent nucleic acid sequences of the barcode, followed by ligation to complete circularization of the oligonucleotide. The circularized oligonucleotide is then amplified with a strand-displacing polymerase, generating an extension product with multiple copies of the circular template. This extension product is then primed with a sequencing primer and subjected to sequencing processes as described herein, thereby providing a high-resolution view of granuloma molecular features that can be combined with additional histological and immunohistochemistry modalities to guide clinical decision-making.

Example 9: Differentiation of Triple Negative Breast Cancer States

Triple negative breast cancer (TNBC) is a subtype of breast cancer that accounts for 15-20% of all breast cancers and is characterized by loss of progesterone receptor, estrogen receptor, and epidermal growth factor receptor (HER2). Patients diagnosed with TNBC have the highest risk of metastasis of any breast cancer and have a 40-80% risk of recurrence after therapy. TNBCs are highly heterogeneous and there is evidence that suggests this heterogeneity contributes to resistance to chemotherapy and relapse (Garrido-Castro A C et al. Cancer Discov. 2019; 9(2): 176-198). Development of resistance to chemotherapy appears to occur through epigenetic changes that modify the activity of key regulators of cell state and produce "persister" cells that can survive prolonged treatment with chemotherapy (Risom T et al. Nat. Commun. 2018; 9(1): 3815 and Echeverria G V et al. Sci. Transl. Med. 2019; 11 (488): eaav0936). There is a lack of understanding regarding the cellular factors that lead to the production and maintenance of these persister cells. Specifically, there is a clinical need to differentiate TNBC states and state transitions in response to chemotherapeutic treatment (e.g., doxorubicin combined with cyclophosphamide).

The methods described herein provide a novel in situ sequencing approach for profiling TNBC tumors at a transcriptional level and monitor the disease state, for example, to determine how different tumors evolve over time and in response to pharmacological treatment. Briefly, tumor cells obtained from a TNBC patient (or from a patient-derived xenograft model) before, during, and/or after pharmacological treatment (e.g., chemotherapy) and are attached to a substrate surface, fixed, and permeabilized according to known methods in the art. Optionally, the sample is cleared (e.g., digested) of proteins, lipids, or proteins and lipids. Targeted padlock probes are then annealed to the nucleic acid of interest (e.g., genes characteristic in a chemotherapeutic resistance signature such as TNF, VEGFA, IL-6, TNFSF10, CLU, ABCC6, EGR1, SNAI1, ABCC3, EPHX1, FASN, CXCL1, IL24, JUNB, and/or TP53I11 (see, e.g., Ciocan-Cartita C A et al. J. Exp. Clin. Cancer Res. 2020; 39(1): 241, and Nedeljkovic M et al. Cells. 2019; 8(9): 957)) and ligated. The resulting circularized oligonucleotide is primed with an amplification primer and extended with a strand-displacing polymerase to generate a concatemer containing multiple copies of the target nucleic acid sequence. This extension product is then primed with a sequencing primer and subjected to sequencing processes as described herein. This methodology also provides temporal information for patients under short- or long-term drug treatment to provide relevant clinical information, for instance, gene signatures indicative of drug resistance.

Example 10: Profiling the Glioblastoma Multiforme Tumor Microenvironment

Glioblastoma multiforme (GBM) is an extremely aggressive brain tumor and one of the deadliest forms of cancer, with a two-year survival rate of less than 1 in 3 (Aldape K et al. Nat. Rev. Clin. Oncol. 2019; 16(8): 509-520). Classification of GBM based on specific gene mutations (isocitrate dehydrogenase-1) or DNA methylation (promoter region of the MGMT DNA repair enzyme) provides an accurate prognosis but has yielded limited clinical improvement in patient outcomes. Defining features of GBM include infiltration of activated microglia and an abundant variety of immune cells not normally found in the brain, e.g., monocyte-derived macrophages, neutrophils, and T-cells (Klemm F et al. Cell. 2020; 181(7): 1643-1660). Understanding the complex cellular milieu of the GBM tumor microenvironment will shed crucial insight into the development of targeted therapeutics.

Single cell profiling of RNA and protein in patient biopsies have recently revealed as many as 14 distinct transcriptional states of microglia within the tissue and tumor microenvironment (Sankowski R et al. Nat. Neurosci. 2019; 22(12): 2098-2110). The fact that intratumor cell heterogeneity is strongly correlated with patient survival underscores the need to determine how tumor and healthy cell functions are coordinated at the tissue level, and how the tumor microenvironment responds to therapeutic intervention (Patel A P et al. Science. 2014; 344(6190): 1396-401). A major obstacle to treating GBM is recurrence after tumor resection. The ability to accurately define and predict tissue state transitions after removal of the tumor would pave the way for novel therapeutics with greater efficacy and reduced toxicity. Defining tissue states based on the properties of tissue resident and infiltrating leukocytes may also provide complementary information regarding the tissue microenvironment.

The methods described herein provide a novel in situ sequencing approach for profiling the GBM tumor microenvironment at a transcriptional level and monitor the disease state, for example, to accurately define and predict tissue state transitions after removal of the tumor and/or in response to pharmacological treatment. Briefly, tumor and/or surrounding cell sample is obtained from a GBM patient (or from a patient-derived xenograft model) before, during, and/or after tumor resection/pharmacological treatment (e.g., chemotherapy) and are attached to a substrate surface, fixed, and permeabilized according to known methods in the art. Optionally, the sample is cleared (e.g., digested) of proteins, lipids, or proteins and lipids. Targeted padlock probes are then annealed to the nucleic acid of interest (e.g., cell-specific factors to identify infiltrating lymphocyte, microglia, neutrophils, macrophages, etc. (see, e.g., Huang S et al. Front. Immunol. 2020; 11: 585034); or, a microglial homeostatic gene, e.g., CX3CR1, TMEM119, CSF1R, P2RY12, P2RY13, SELPLG, GLUT5, CD64, HLA-DR, TREM2, APOE, GPR56 and/or MARCKS) and ligated. The resulting circularized oligonucleotide is primed with an amplification primer and extended with a strand-displacing polymerase to generate a concatemer containing multiple copies of the target nucleic acid sequence. This extension product is then primed with a sequencing primer and subjected to sequencing processes as described herein. This methodology also provides temporal information for patients under short- or long-term drug treatment to provide relevant clinical information, for instance, gene signatures indicative of drug resistance.

Example 11: Pharmacodynamic and Biomarker Analysis of a T Cell Immunomodulatory Molecule A wealth of information is reflected in the temporal and spatial variation of gene and protein expression among cells. Cellular macromolecules such as nucleic acids and proteins, occupy precise positions in cells and tissues, and a great deal of information is lost when these molecules are extracted. The methods available today for RNA sequence analysis (RNA-Seq) have the capacity to quantify the abundance of RNA molecules in a population of cells with great sensitivity. Current methods for single-cell RNA and protein analysis typically involve some method for "barcoding" the content of individual cells, followed by pooling the content and sequencing on a commercial DNA sequencing device (e.g., Illumina NextSeq™ 500/550, MiSeq™, HiSeq™ 2500/3000/4000, or NovaSeq™). These methods have found wide application dissecting transcriptomic heterogeneity, and can handle upwards of 10,000 cells in an automated format, however they have several limitations and drawbacks. For example, if the cells of interest originate from a tissue sample, all information about the spatial distribution of the cells within the tissue is lost in the process of dissociating and isolating the cells prior to barcoding them. Often information about the intracellular distribution of analytes within the cellular microenvironment is also lost. This information can be vital to designing therapeutic approaches to cancers, for example, where the tumor microenvironment often creates spatial gradients of nutrients and metabolic byproducts.

In situ sequencing typically involves tissue and/or cellular extraction, combined with the fixation and permeabilization of cells, followed by amplification of the target nucleic acid fragments for sequencing. Briefly, cells and their surrounding milieu are attached to a substrate surface, fixed, and permeabilized. Targeted oligonucleotide probes designed for C—V-D-J sequencing are then annealed to complementary regions which flank the nucleic acid of interest or a portion thereof and ligated. The resulting circularized oligonucleotide is primed with an amplification primer and extended with a strand-displacing polymerase to generate a concatemer containing multiple copies of the target nucleic acid sequence. This extension product is then primed with a sequencing primer and subjected to sequencing processes as described herein.

In embodiments, the methods described herein may be utilized for B cell heavy and light chain in situ sequencing by targeting the combination of variable and constant gene segments that make up a given heavy and light chain. These methods provide unique insight into the spatial localization and recombination efforts of a cell's heavy and light chain genes. Likewise, the methods can be applied for T-cell receptor (TCR) alpha and beta chain in situ sequencing. The genes encoding alpha (TCRA) and beta (TCRB) chains are composed of multiple non-contiguous gene segments which include V, D, and J segments for TCRB and V and J for TCRA. As with B cell receptor diversity, the enormous diversity of TCR repertoires is generated by random combinatorial gene events. The methods described here can be used to provide a comprehensive in situ view of TCR diversity in intact T cells.

Non-adherent cells may also serve as an important source of information for assessing the activity of candidate therapeutic agents. Immunomodulatory agents, for example, (alternatively referred to herein as cell modifying agents) have wide utility to the treatment of cancer, infectious and autoimmune disease, and may act upon adherent and non-adherent cell types. In the context of cancer immunotherapy, immunomodulatory agents may function by directly altering the activity of relevant immune cells (e.g., repression of immune suppressive cells or activation of anti-tumor cells), or indirectly eliciting immune cell responses by altering the immunogenicity of the cancer. For each modality there are numerous agents in active development or approved for clinical use. The number of potential treatment strategies is further increased by combinatorial immunotherapy strategies, where two or more agents are contemporaneously applied to enhance efficacy through complementary modes of action. Each immunomodulatory agent may give rise to one or more unique signatures that are detectable through the analysis of single cell gene expression, protein expression, and cell morphology. Here we describe methods for identifying agent-specific activity signatures. The methods have utility for the assessment of the pharmacodynamic activity of a therapeutic agent and as a means to identify predictive and prognostic biomarkers of response following a therapeutic intervention.

Checkpoint blockade immunotherapy may elicit durable anti-tumor responses that may be mediated in part by modulation of T cell activity. Methods to quantify the activity of a therapeutic agent are useful for understanding dose/exposure-response relationships and may reveal predictive and prognostic biomarkers of response (Agrawal, S., Feng, Y., Roy, A. et al. j. immunotherapy cancer 4, 72 (2016)). FIG. 8 provides an overview of a workflow using the methods as described herein to evaluate pharmacodynamics and identify biomarkers of response for a candidate T cell immunomodulating agent (e.g., a checkpoint blockade inhibitor) as part of a human dose escalation study (FIG. 8). Peripheral blood leukocytes are obtained from individuals receiving from 0.1-10 mg/kg of the agent over timepoints ranging from time of administration (day 0) to 30 days post administration. In parallel, peripheral blood leukocytes are obtained from matched controls. Cells are analyzed for expression of one or more marker genes (e.g., CD3, CD4, CD8, FOXP3, TIM-3, PD-1, CTLA-4, Ki67, IFNG, IL-10, IL-17, LAG-3, TIGIT, CD40, GITR, ICOS, OX40, CD25, KLRG1, CD27, CCR7, CXCR5, CD127, CD39) and cell images are acquired for analysis of cell morphology. In some embodiments, morphology analysis is performed in conjunction with application of cell staining or other contrast enhancing approaches known in the art (e.g., H & E staining, etc). Data from CD4 or CD8 positive T cells (cells expressing CD3 in combination with either CD4 or CD8; referred to herein as "core" markers) is retained for training of a model to discriminate treatment cells from control cells.

Following training, model performance is assessed using methods known in the art (e.g., cross-validation) to produce an area under the receiver-operator characteristic curve (AUC) summarizing the model performance for each dose and timepoint. An example of the results is presented in FIG. 9. Higher AUC values indicate the model can better discriminate treatment from control. AUC thus serves as a proxy for agent-mediated modulation of T cells. In FIG. 9, based on AUC analysis, a dose of 3 mg/kg or higher and a sampling timepoint of 10 days post administration appears to be the optimal combination for detecting an effect of the agent.

Figure 10:
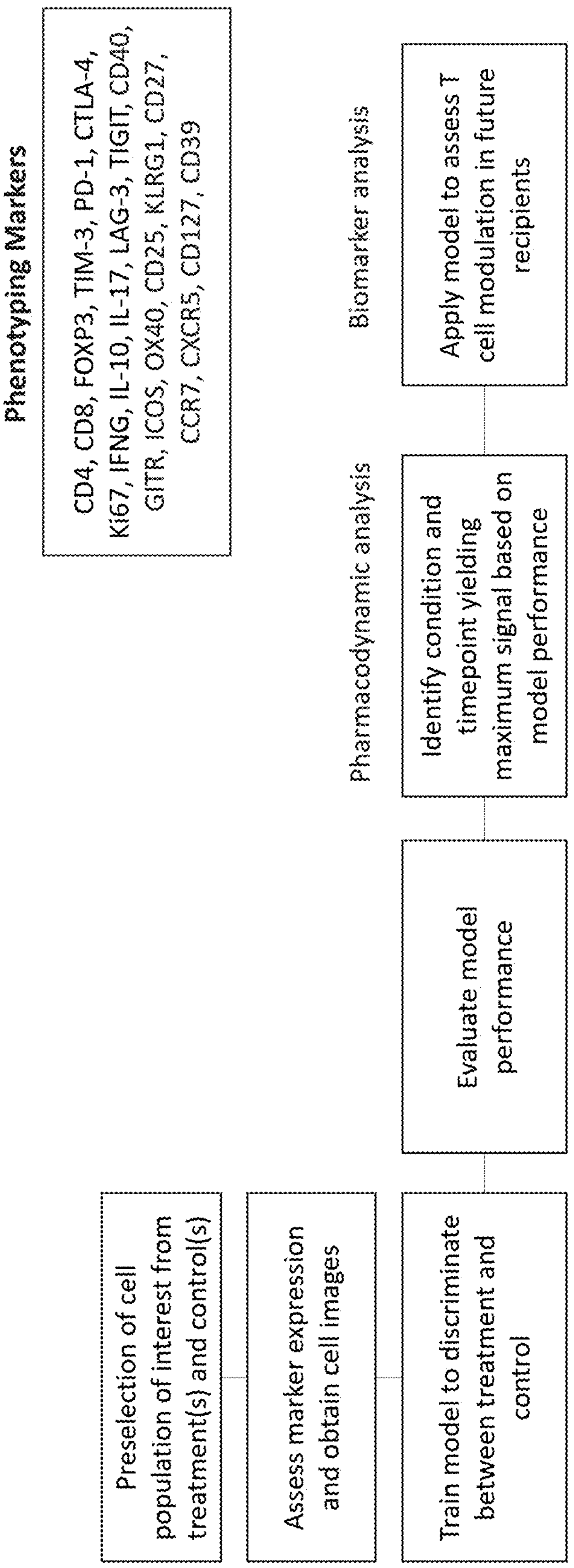
FIG. 10 provides an embodiment of a method for pharmacodynamic and biomarker analysis of a T cell modulating immunotherapy using presorted cells.

Following pharmacodynamic analysis, the model may be applied to evaluate response in individuals receiving the therapy. In a hypothetical example, a group of individuals receives the agent at 3 mg/kg. Peripheral blood lymphocytes (PBLs) are extracted at day 10 post-administration and analyzed via the methods described herein, then T cell modulation is quantified using the corresponding dose-timepoint model trained as part of pharmacodynamic analysis. The magnitude of T cell modulation is then correlated with clinical endpoints (e.g., progression free survival, objective response rate, etc.) to validate the predictive or prognostic utility of the metric. Finally, the validated metric is applied to predict outcomes for future recipients of the agent. FIG. 10 illustrates a variation of the above workflow where T cells of interest are preselected. Preselection eliminates the need to identify the relevant cell subpopulation by core marker analysis and minimizes analysis of irrelevant cell types.

Example 12: Measurable Residual Disease Monitoring of Acute Myeloid Leukemia

Measurable residual disease (MRD) is an important prognostic indicator with relevance to treatment planning and risk stratification for Acute Myeloid Leukemia (AML) (Wilson C S, Davidson G S, Martin S B, et al. Blood. 2006; 108(2):685-696; Bullinger et al. N Engl J Med 2004; 350: 1605-1616). Flow cytometric based detection of AML is an established method for detection and phenotyping of AML. The limit of detection for flow cytometry-based MRD assessment for AML is typically between 0.1-0.01% and is limited in part by the specificity of markers used for identification of the malignant cells (Peters J M, Ansari M Q. Multiparameter flow cytometry in the diagnosis and management of acute leukemia. Arch Pathol Lab Med. 2011 January; 135(1):44-54).

There is an urgent need for methods to assess residual disease for precision medicine. Technical challenges of residual disease detection include the need for a high sensitivity and specificity at a low limit of detection. Personalized cancer monitoring strategies aim to improve sensitivity and specificity by identifying and tracking patient-specific cancer mutations. Such methods require custom reagents, increasing testing complexity, cost, and turnaround time, ultimately reducing clinical utility. Herein we present methods for personalized cancer monitoring, for example, where the personalization is at the level of patient specific cancer cell image analysis morphology and is achieved through machine learning based image analysis. A patient specific neural network optimized to detect the patient's cancer obviates the need for custom reagents. The methods enable high sensitivity and specificity at a low limit of detection, while reducing the need for custom reagents. Utilizing the methods described herein, that is, combining cell morphology information with marker-based assessment, provides improved specificity of detection, thereby enabling a lower limit of detection.

A non-limiting example of a workflow for MRD monitoring of AML using the device described herein is presented in FIG. 7. The workflow begins by selection of a set of 'core' markers for identification of the malignant AML cells from a donor peripheral blood leukocyte (PBL) sample (FIG. 7). Relevant markers are known to those in the art and may include one or more of the following genes: CD7, CD11b, CD13, CD14, CD15, CD16, CD33, CD34, CD45, CD56, CD 117, HLA Dr (Agrawal, S., Feng, Y., Roy, A. et al. j. immunotherapy cancer 4, 72 (2016)). Additional gene expression or mutation hotspot markers (e.g., determining the presence of one or more recurrent mutations from RNA/cDNA) may be included to aid in phenotyping of malignant cells. Phenotyping markers may include one or more of the following CD2, cCD3, CD4, cCD22, CD25, CD36, CD38, CD41, CD61, cCD61, CD64, CD71, cCD79a, cMPO, CD123, CD163, CD235a, TdT, GPHA, cIgM, WT1, EVI1, LTBP1, VASP3, FTO, FOXC1, CEBPA, FLT3, among others.

PBL cells from the donor are isolated, then analyzed using the methods described herein to determine the nucleic acid (e.g., RNA or cDNA) and/or protein expression of each selected marker (i.e., core and phenotyping markers), assess mutations, and obtain cell images for analysis of cell morphology. In some embodiments, morphology analysis is performed in conjunction with application of cell staining or other contrast enhancing approaches known in the art (e.g., H & E staining, etc). In some embodiments, more than about 1000 cells are analyzed in a single experiment. The expression status of the core markers is used to categorize each cell dataset as belonging to a malignant or non-malignant cell. Optionally, the set of identified malignant cells may be assigned to an AML subtype (e.g., AML-MO, AML-M1, AML-M2, etc.) by evaluating the status of the phenotyping markers and comparing malignant cell images to an image database of classified AML subtypes.

Next, labeled data is used to train a machine learning model to identify cell image features that distinguish malignant cells from non-malignant cells. Optionally, the model is trained using both the status of the phenotyping markers and the cell images. Training is performed using methods known in the art. Following training, model performance and validation is assessed using methods known in the art (e.g., cross-validation). This may include application of the model to additional labeled cell datasets, or applying the model to a control, such as a negative control dataset (e.g., data derived from the analysis of healthy donor PBL). Finally, the validated model is applied in conjunction with the analysis of the core marker set to determine the presence of malignant cells in future samples derived from the same donor.

Example 13: Padlock Probe Specificity

Detecting differential expression of multiple transcripts in heterogeneous cell populations is an important application of in situ transcriptomics, and is directly correlated, for example, to the specificity of the padlock probes (PLPs) being used to target the transcripts. To show that the approach described herein has the specificity to resolve multiple transcripts, we selected two target genes (MEIS2 and ERBB2) in two cell lines (SK-BR-3 and U-138MG). Based on RNAseq data reported on The Human Protein Atlas, the SK-BR-3 human breast cancer cell line (ATCC HTB-30™) has high expression of the ERBB2 gene product, while the U-138MG glioblastoma cell line (ATCC HTB-16™) has high expression of the MEIS2 gene product, relative to each other (see, e.g., Table 1; data for ERBB2 acquired from www.proteinatlas.org/ENSG00000141736-ERBB2/cell #rna, and data for MEIS2 acquired from www.proteinatlas.org/ENSG00000134138-MEIS2/cell #rna).

Plating and Fixation: All steps were performed in 96-well plate format. Cell suspensions were centrifuged for 5 min at 0.3 rcf and resuspended in 1×PBS prior to plating. Cells were plated at a density of 100,000 live cells/well and allowed to settle at the bottom of the plate for at least 30 min at 4° C. Cells were then fixed with 4% formaldehyde in 1×PBS for 15 min at room temperature (RT), and washed 3 times with 1×PBS to remove the formaldehyde. Cells were then permeabilized with 0.5% Triton X-100 in 1×PBS for 20 min at RT, then washed 1× with 1×PBS and 2× with hybridization buffer (20% formamide and 2×SSC in water).

Hybridization and Probe Ligation: Padlock probes (PLPs) were added at a final concentration of 100 nM each with 10 mM ribonucleoside vanadyl complex (RVC) in hybridization buffer. PLPs were then allowed to hybridize overnight at 37° C. The cells were then washed 1× with hybridization buffer for 5 min at 37° C. and 2× with 1×PBS for 5 min each at 37° C. Following the washes, SplintR® ligase (New England Biolabs Catalog #M0375S) was added at a final concentration of 2.5 U/uL with 0.2 U/uL SUPERase-In™ RNase inhibitor (Thermo Fisher Catalog #AM2694) in 1× Splint® ligase buffer and incubated for 30-60 min at 37° C. Cells were then washed 1× with 1×PBS and 2× with hybridization buffer.

Rolling Circle Amplification: Phosphorothioated amplification primer was added at a final concentration of 0.5 uM in hybridization buffer and incubated for 1 hr at 37° C. Cells were then washed 1× with hybridization buffer and 2× with 1×PBS. A mutant version of phi29 DNA polymerase was then added at a final concentration of 0.45 uM with 1 M betaine, dNTPs (0.5 mM each), 0.125 mM aminoallyl-dUTP, 0.2 mg/mL BSA, 4 mM DTT, and 0.2 U/uL SUPERase-In™ RNase inhibitor in DEPC-treated water and incubated for 1 hr at 37° C. Cells were then washed 3× with 1×PBS.

Crosslinking: BS(PEG)9 was then added at a final concentration of 5 mM in 1×PBS and incubated for 30 min at RT. Cells were then washed 1× with 1×PBS, and 1 M Tris (pH 8.0) added and incubated for 15 min at RT. Cells were then washed 3× with flow cell wash buffer (20 mM Tris, 0.025% Triton X-100, 0.1 mM EDTA, 100 mM NaCl, pH 8.04) and detection was performed.

Detection: TetraSpeck™ microspheres were added to crosslinked cells at a final concentration of 0.1 nM in PBST (0.1% Tween-20 in 1×PBS) and allowed to settle for at least 30 min at RT, or centrifuged for 3 min at 2,000 RPM. Sequencing primer was then added at a final concentration of 0.5 uM in hybridization buffer and incubated for 30 min at 37° C. The cells were then washed 3× with flow cell wash buffer, and sequencing-by-synthesis with detectable nucleotides was performed for 5 cycles.

Using the methods described herein and in Example 1, we observed in situ the expected high expression of ERBB2 and low expression of MEIS2 in the SK-BR-3 cells (FIG. 12, top panel), whereas the U-138MG had relatively high expression of MEIS2 and low expression of ERBB2 (FIG. 12, middle panel), wherein detection of the base A was indicative of a padlock probe specific for ERBB2, and detection of the base T was indicative of a padlock probe specific for MEIS2.

TABLE 1

Relative expression of MEIS2 and ERBB2 in two SK-BR-3 and U-138MG cells

| Gene | SK-BR-3 | U-138MG |
|---|---|---|
| MEIS2 | 2.7 | 14.2 |
| ERBB2 | 179.8 | 1.7 |

Figure 12:
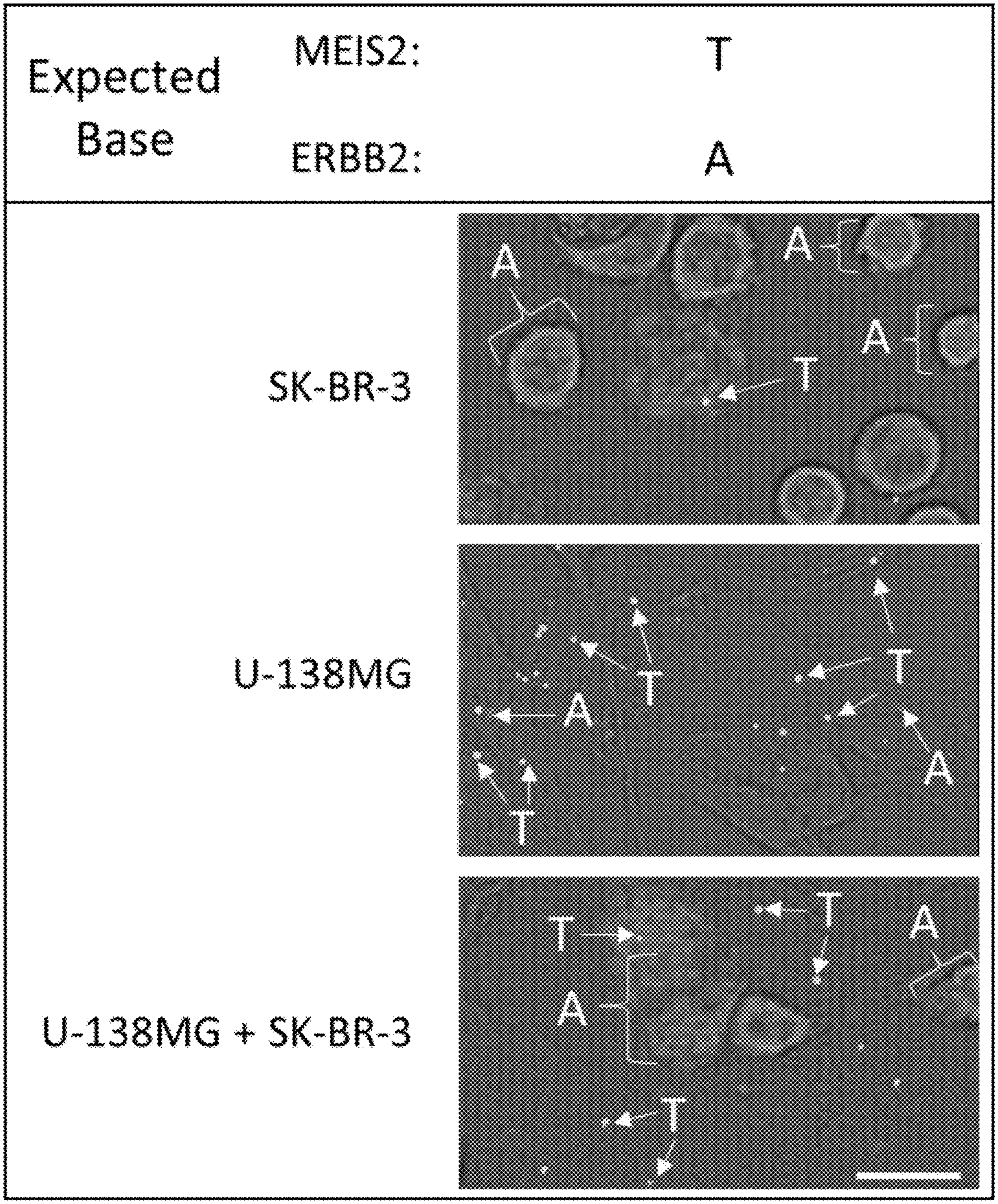
FIG. 12 is a set of fluorescence microscopy images of two cell types (SK-BR-3 and U-138MG) probed with padlock probes (PLP) specific for the gene product of either MEIS2 or ERBB2. Each fluorescent image is overlayed with a transmitted light microscopy image of the probed cells. SK-BR-3 cells alone (top panel), U-138MG cells alone (middle panel), and co-cultured U-138MG and SK-BR-3 cells (bottom panel) were probed. The PLPs were applied using the methods described herein, and following amplification, each PLP barcode was sequenced in situ. The areas of cells containing detectable fluorescence for the base A are indicated by arrows and brackets and represent the PLP specific for the ERBB2 gene product. The areas of cells containing detectable fluorescence for the base T are indicated by arrows and represent the PLP specific for the MEIS2 gene product.

The two cell lines also have distinct morphology discernable by transmitted light imaging: SK-BR-3 cells (FIG. 12, top panel) have a compact round morphology, whereas U-138MG are spread more broadly with protrusions extending from the main cell bodies (FIG. 12, middle panel). Thus, the two cell types are readily identifiable in co-culture, as is seen in the bottom panel of FIG. 12. In the co-culture the regions of MEIS2 and ERBB2 expression are spatially segregated to regions identifiable as U-138MG or SK-BR-3 (respectively) by morphology. These spatially distinct profiles show that our approach has high specificity across cell types and targets.

Example 14: Transcript Counting by In Situ Sequencing

To demonstrate the ability of our approach to detect occurrences of transcripts from multiple genes simultaneously, we probed in a multiplex fashion for 20 genes. The transcript for each gene was targeted by 3 padlock probe (PLP) designs, each targeting different regions of the same transcript. Each of the 3 PLPs for the same transcript had different feet (complementary to the target sequence), but the same 20 base barcode in the backbone of the PLP. All PLPs had the same structure from 5' to 3': a first domain (also known as a "foot" or "pad") capable of hybridizing to a first target sequence, a sequencing primer binding sequence, an oligonucleotide barcode from a known set of barcodes, an amplification primer sequence, and a second foot capable of hybridizing to a second target sequence adjacent to the first target sequence. Sequences for the first domain complementary to the first target sequence and second domain complementary to the second target sequence used in the 3 PLP designs for each of the 20 genes described in FIG. 13 and FIG. 14 were found in, for example, Gyllborg D et al. Nucleic Acids Research. 2020; 48 (19): e112 and Alon S et al. Science. 2021; 371 (6528): eaax2656, each of which is incorporated herein by reference in their entirety.

Figure 13:
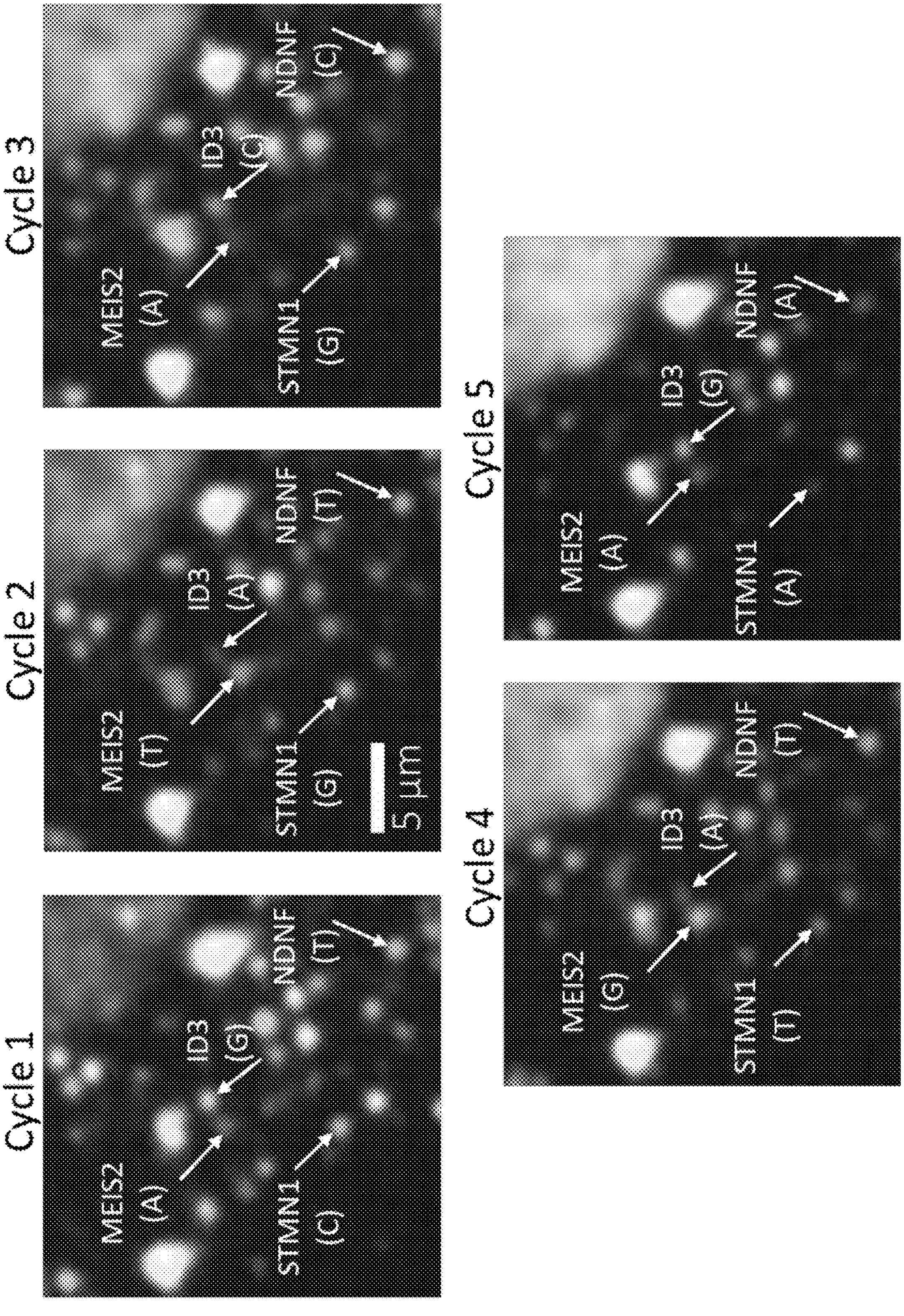
FIG. 13 presents a set of fluorescence microscopy images of cells probed in a multiplex fashion (i.e., simultaneous detection) for 20 genes across 5 in situ sequencing cycles. Each tile has four genes highlighted for PLP barcode sequencing: MEIS2, ID3, STMN1, and NDNF. The transcript for each gene was targeted by 3 PLP designs, each targeting different regions of the same transcript. Each of the 3 PLPs for the same transcript had different feet (i.e., sequences complementary to the target sequence) but the same 20 base barcode in the backbone of the PLP. The changing color (color not shown) of each dot per cycle is mapped to an appropriate base (A, T, C or G) and the change in color of a dot across the 5 cycles reveals the barcode, which can be used to identify which gene the transcript is copy of (see, Table 2).

Using the methods described herein and in Examples 1 and 13, it is apparent that across the 5 cycles dots remain in the same spatial pattern, but the color of each dot changes (FIG. 13), indicating differential nucleotide incorporation from cycle to cycle. Note, FIG. 13 is in grayscale and therefore the bases called in each cycle are explicitly denoted in each tile with the base corresponding to the detectable signal. The colors can be mapped to an appropriate base (A, T, C or G) and the change in color of a dot across the 5 cycles reveals its barcode sequence, which can be used to identify which gene the transcript is copy of (see, Table 2).

TABLE 2

In situ gene-specific barcode sequencing across 5 cycles

| Gene | Cycle 1 | Cycle 2 | Cycle 3 | Cycle 4 | Cycle 5 |
|---|---|---|---|---|---|
| MEIS2 | A | T | A | G | A |
| ID3 | G | A | C | A | G |
| STMN1 | C | G | G | T | A |
| NDNF | T | T | C | T | A |

Figure 14:
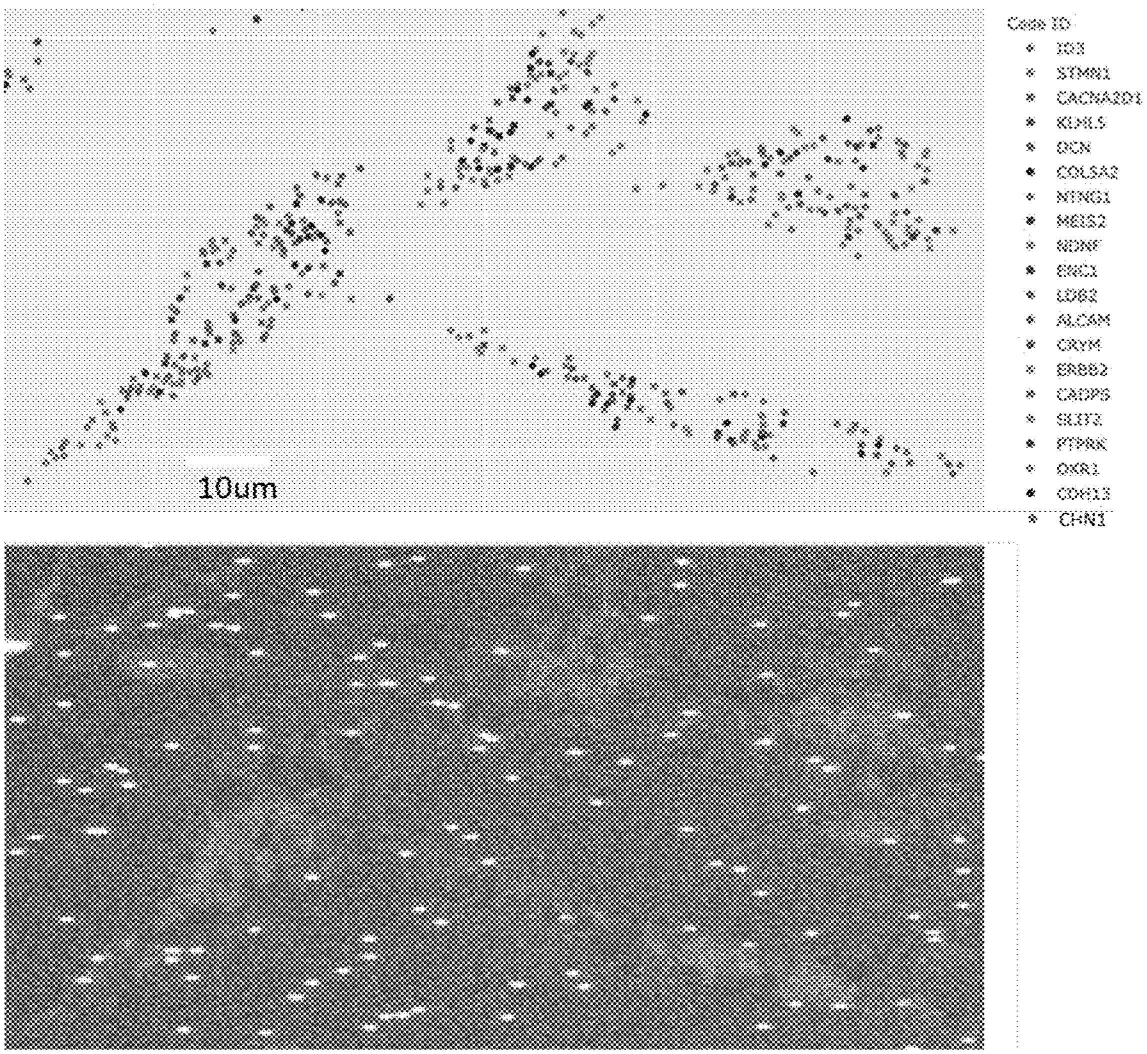
FIG. 14 is a computer illustration depicting the spatial location of transcripts for all 20 genes targeted simultaneously as described in FIG. 13. The results are demonstrated in the top panel of FIG. 14, in which the location for the transcripts identified are denoted by a dot with a color associated with which of the multiplexed genes that transcript is associated with. The overlay of all the dots reveals the structure of the cell body. An overlay of all called dots (red circles) on an auto fluorescence gray scale image is also presented (FIG. 14, bottom panel). In this image, the bright white dots are focusing beads, the dark gray regions are extra-cellular space and the light gray regions are the cell body. We note that all identified transcripts (red dots) fall within the cell body (light grey region).

Reading the sequences as described in FIG. 13, our approach can count and determine the spatial location of transcripts for all genes targeted simultaneously. The results are demonstrated in the top panel of FIG. 14, in which the location for the transcripts identified are denoted by a dot with a color associated with which of the multiplexed genes that transcript is associated with. The overlay of all the dots reveals the structure of the cell body. As a sanity check, we can overlay all called dots (red circles) on an auto fluorescence gray scale image (FIG. 14, bottom panel). In this image, the bright white dots are focusing beads, the dark gray regions are extra-cellular space and the light gray regions are the cell body. We note that all identified transcripts (red dots) fall within the cell body (light grey region).

What is claimed is:

1. A method of detecting targets of a cell, said method comprising:

(i) binding a first polynucleotide probe to a first nucleic acid molecule in the cell;

forming a first amplification product comprising multiple complements the first polynucleotide probe; and binding a first fluorescently labeled nucleotide to the first amplification product;

(ii) binding a second polynucleotide probe to an oligonucleotide of an antibody-oligonucleotide conjugate, wherein the antibody-oligonucleotide conjugate is attached to a protein in or on said cell; forming a second amplification product comprising multiple complements of the second polynucleotide probe; and binding a second fluorescently labeled nucleotide to the second amplification product;

(iii) binding a fluorescent stain to an organelle of the cell; and (iv) detecting the targets by detecting the first fluorescently labeled nucleotide, the second fluorescently labeled nucleotide, and the fluorescent stain.

2. The method of claim 1, wherein forming a first amplification product and forming a second amplification product comprises rolling circle amplification or exponential rolling circle amplification.

3. The method of claim 1, wherein (iv) comprises:

a) detecting the second fluorescently labeled nucleotide;

b) followed by detecting the first fluorescently labeled nucleotide;

c) followed by detecting the fluorescent stain.

4. The method of claim 1, wherein the fluorescent stain comprises an ER stain, Golgi stain, F-actin stain, lysosomal stain, mitochondrial stain, nucleolar stain, or plasma membrane stain.

5. The method of claim 1, wherein the fluorescent stain is eosin.

6. The method of claim 1, wherein binding the first fluorescently labeled nucleotide comprises hybridizing a primer to the first amplification product and incorporating the first fluorescently labeled nucleotide.

7. The method of claim 6, wherein the first fluorescently labeled nucleotide comprises a reversible terminator.

8. The method of claim 7, further comprising incorporating a plurality of fluorescently labeled nucleotides into the primer, wherein the fluorescent label is detected and the reversible terminator is removed prior to the incorporation of a next nucleotide.

9. The method of claim 1, wherein the fluorescently labeled nucleotide forms part of a detection oligonucleotide, and binding a fluorescently labeled nucleotide comprises hybridizing the detection oligonucleotide to the first amplification product.

10. The method of claim 1, wherein the cell forms part of a tissue, and said tissue comprises liver tissue, kidney tissue, bone tissue, lung tissue, thymus tissue, adrenal tissue, skin tissue, bladder tissue, colon tissue, spleen tissue, or brain tissue.

11. The method of claim 10, wherein said tissue comprises breast tissue, lung tissue, colon tissue, lymph tissue, kidney tissue, bone tissue, or brain tissue.

12. The method of claim 1, wherein the first nucleic acid molecule is an RNA molecule.

13. The method of claim 1, wherein the first nucleic acid molecule is a DNA molecule.

14. The method of claim 1, further comprising identifying the cell based on the detected targets.

15. The method of claim 1, wherein (iv) comprises:

a) detecting the first fluorescently labeled nucleotide;

b) followed by detecting the second fluorescently labeled nucleotide;

c) followed by detecting the fluorescent stain.

16. The method of claim 1, wherein (iv) comprises:

a) detecting the first fluorescently labeled nucleotide;

b) followed by detecting the fluorescent stain;

c) followed by detecting the second fluorescently labeled nucleotide.

17. The method of claim 1, wherein (iv) comprises:

a) detecting the second fluorescently labeled nucleotide;

b) followed by detecting the fluorescent stain;

c) followed by detecting the first fluorescently labeled nucleotide.

18. The method of claim 1, wherein (iv) comprises:

a) detecting the fluorescent stain;

b) followed by detecting the first fluorescently labeled nucleotide;

c) followed by detecting the second fluorescently labeled nucleotide.

19. The method of claim 1, wherein (iv) comprises:

a) detecting the fluorescent stain;

b) followed by detecting the second fluorescently labeled nucleotide;

c) followed by detecting the first fluorescently labeled nucleotide.

20. The method of claim 1, wherein the antibody-oligonucleotide conjugate is bound to CD3, CD4, CD8, FOXP3, TIM-3, PD-1, CTLA-4, Ki67, IFNG, IL-10, IL-17, LAG-3, TIGIT, CD40, GITR, ICOS, OX40, CD25, KLRG1, CD27, CCR7, CXCR5, CD127, or CD39.

* * * * *